United States Patent [19]

Bonadio et al.

[11] Patent Number: 5,763,416
[45] Date of Patent: Jun. 9, 1998

[54] GENE TRANSFER INTO BONE CELLS AND TISSUES

[75] Inventors: Jeffrey Bonadio; Steven A. Goldstein, both of Ann Arbor, Mich.

[73] Assignee: The Regent of the University of Michigan, Ann Arbor, Mich.

[21] Appl. No.: 199,780

[22] Filed: Feb. 18, 1994

[51] Int. Cl.⁶ .......................... C12N 15/00; C07H 21/02; C07H 21/04; A61K 48/00
[52] U.S. Cl. ............... 514/44; 435/172.3; 435/320.1; 536/23.1; 536/23.5; 536/23.51; 514/801; 424/600; 424/423; 424/422; 424/484; 424/486
[58] Field of Search .......................... 435/172.3, 69.1; 514/44, 74; 536/23.5

[56] References Cited

U.S. PATENT DOCUMENTS

| | | | |
|---|---|---|---|
| 4,137,921 | 2/1979 | Okuzumi et al. | 128/335.5 |
| 4,166,800 | 9/1979 | Fong | 252/316 |
| 4,181,983 | 1/1980 | Kulkarni | 3/1 |
| 4,243,775 | 1/1981 | Rosensaft et al. | 525/415 |
| 4,279,249 | 7/1981 | Vert et al. | 1287/92 D |
| 4,300,565 | 11/1981 | Rosensaft et al. | 128/335.5 |
| 4,347,234 | 8/1982 | Wahlig et al. | 424/15 |
| 4,384,975 | 5/1983 | Fong | 427/213.36 |
| 4,390,519 | 6/1983 | Sawyer | 424/28 |
| 4,409,332 | 10/1983 | Jefferies et al. | 435/188 |
| 4,455,256 | 6/1984 | Urist | 260/112 R |
| 4,472,840 | 9/1984 | Jefferies | 3/1.9 |
| 4,530,449 | 11/1985 | Tunc | 623/16 |
| 4,538,603 | 9/1985 | Pawelchak et al. | 128/156 |
| 4,539,981 | 9/1985 | Tunc | 128/92 B |
| 4,563,350 | 1/1986 | Nathan et al. | 424/95 |
| 4,563,489 | 1/1986 | Urist | 524/21 |
| 4,568,559 | 2/1986 | Nuwayser et al. | 427/3 |
| 4,578,384 | 3/1986 | Hollinger | 514/8 |
| 4,585,797 | 4/1986 | Cioca | 514/773 |
| 4,591,501 | 5/1986 | Cioca | 424/28 |
| 4,596,574 | 6/1986 | Urist | 623/16 |
| 4,619,989 | 10/1986 | Urist | 530/417 |
| 4,623,588 | 11/1986 | Nuwayser et al. | 428/402.24 |
| 4,703,108 | 10/1987 | Silver et al. | 530/356 |
| 4,711,783 | 12/1987 | Huc et al. | 424/460 |
| 4,741,337 | 5/1988 | Smith et al. | 128/334 R |
| 4,744,365 | 5/1988 | Kaplan et al. | 128/335.5 |
| 4,761,471 | 8/1988 | Urist | 530/350 |
| 4,776,890 | 10/1988 | Chu | 106/161 |
| 4,789,663 | 12/1988 | Wallace et al. | 514/21 |
| 4,789,732 | 12/1988 | Urtist | 530/350 |
| 4,795,804 | 1/1989 | Urist | 530/350 |

(List continued on next page.)

FOREIGN PATENT DOCUMENTS

| | | |
|---|---|---|
| 0 614 974 A2 | 9/1994 | European Pat. Off. |
| 42 19 626 A1 | 12/1993 | Germany |
| WO 90/03733 | 4/1990 | WIPO |
| 9011092 | 10/1990 | WIPO |
| WO 90/11092 | 10/1990 | WIPO |
| WO 90/14074 | 11/1990 | WIPO |
| WO 91/17424 | 11/1991 | WIPO |
| WO 92/05199 | 4/1992 | WIPO |
| WO 92/07573 | 5/1992 | WIPO |
| WO 93/05751 | 4/1993 | WIPO |
| WO 93/09229 | 5/1993 | WIPO |
| 93/15109 | 8/1993 | WIPO |
| WO 93/14778 | 8/1993 | WIPO |
| WO 93/16739 | 9/1993 | WIPO |
| WO 94/01139 | 1/1994 | WIPO |
| 94/20615 | 9/1994 | WIPO |

OTHER PUBLICATIONS

Tarume et al Orch Otolaryngel Mead Nech Surg 117: 1101, 1991.
Chen et al. J. Bore & Minor Research 6(12): 1387, 1991.
Wilson et al Endocrinology 130(5): 2947, 1992.
Alper, "Boning Up: Newly Isolated Proteins Heal Bad Breaks", Science, 263:324–325, 1994.
Bandara, G., et al., "Gene Transfer to Synoviocytes: Prospects for Gene Treatment of Arthritis", DNA and Cell Biology, 11(3):227–231, 1992.
Beck, L. Steven, et al., "Rapid Publication TGF-$\beta_1$ Induces Bone Closure of Skull Defects", J. Bone Miner. Res., 6(11):1257–1265, 1991.
Boden, S.D., et al., "Estrogen Receptor mRNA Expression in Callus During Fracture Healing in the Rat", Calcif Tissue Int, 45:324–325, 1989.
Bonnarens and Einhorn, "Production of a Standad Closed Fracture in Laboratory Animal Bone", J. Orthop. Res., 2:97–101, 1984.
Carrington, Jill L., et al., "Accumulation, Localization, and Compartmentation of Transforming Growth Factor $\beta$ During Endochondral Bone Development", J. Cell Biol., 107:1969–1975, 1988.
Centrella, Michael et al., "Skeletal Tissue and Transforming Growth Factor $\beta$", FASEB J., 2:3066–3073, 1988.
Chen, Theresa L., et al., "Bone Morphogenetic Protein-2b Stimulation of Growth and Osteogenic Phenotypes in Rat Osteoblast–like Cells: COmparison with TGF-$\beta_1$", J. Bone Miner. Res., 6(12):1387–1393, 1991.
Cunningham, Noreen s., et al., "Osteogenin and Recombinant Bone Morphogenetic Protein 2B are Chemotactic for Human Monocytes and Stimulate Transforming Growth Factor $\beta_1$ mRNA Expression", Proc. Natl. Acad. Sci. USA, 89:11740–11744, 1992.

(List continued on next page.)

Primary Examiner—Suzanne E. Ziska
Attorney, Agent, or Firm—Arnold, White & Durkee

[57] ABSTRACT

Disclosed are methods, compositions and devices for use in transferring nucleic acids into bone cells in situ. The transfer of an osteotropic gene into bone progenitor cells is described, which event is shown to stimulate the progenitor cells and to promote bone growth, repair and regeneration in vivo. These gene transfer protocols are suitable for use in transferring various nucleic acid materials into bone, and have many uses, for example, in treating various bone-related diseases and defects, such as, in promoting fracture repair, use in connection with implants, and in treating osteoporosis and osteogenesis imperfecta.

77 Claims, 14 Drawing Sheets

U.S. PATENT DOCUMENTS

| | | | |
|---|---|---|---|
| 4,798,786 | 1/1989 | Tice et al. | 435/177 |
| 4,806,523 | 2/1989 | Bentz et al. | 514/2 |
| 4,818,542 | 4/1989 | DeLuca et al. | 424/491 |
| 4,833,125 | 5/1989 | Neer et al. | 514/12 |
| 4,837,285 | 6/1989 | Berg et al. | 530/356 |
| 4,839,130 | 6/1989 | Kaplan et al. | 264/235 |
| 4,844,854 | 7/1989 | Kaplan et al. | 264/235 |
| 4,865,846 | 9/1989 | Kaufman | 424/428 |
| 4,877,864 | 10/1989 | Wang et al. | 530/324 |
| 4,882,150 | 11/1989 | Kaufman | 424/428 |
| 4,889,119 | 12/1989 | Jamiolkowski et al. | 606/220 |
| 4,898,186 | 2/1990 | Ikada et al. | 606/62 |
| 4,898,734 | 2/1990 | Mathiowitz et al. | 424/426 |
| 4,902,508 | 2/1990 | Badylak et al. | 424/95 |
| 4,916,193 | 4/1990 | Tang et al. | 525/413 |
| 4,938,763 | 7/1990 | Dunn et al. | 604/891.1 |
| 4,946,450 | 8/1990 | Erwin | 604/294 |
| 4,952,402 | 8/1990 | Sparks et al. | 424/419 |
| 4,956,178 | 9/1990 | Badylak et al. | 424/551 |
| 4,957,902 | 9/1990 | Grinnell | 514/17 |
| 4,961,707 | 10/1990 | Magnusson et al. | 433/215 |
| 4,968,590 | 11/1990 | Kuberasampath et al. | 530/326 |
| 4,975,526 | 12/1990 | Kuberasampath et al. | 530/350 |
| 4,975,527 | 12/1990 | Koezuka et al. | 530/356 |
| 4,988,358 | 1/1991 | Eppley et al. | 623/16 |
| 5,001,169 | 3/1991 | Nathan et al. | 523/113 |
| 5,004,602 | 4/1991 | Hutchinson | 424/78 |
| 5,007,939 | 4/1991 | Delcommune et al. | 623/66 |
| 5,011,691 | 4/1991 | Oppermann et al. | 424/423 |
| 5,011,692 | 4/1991 | Fujioka et al. | 424/426 |
| 5,013,649 | 5/1991 | Wang et al. | 435/69.1 |
| 5,035,893 | 7/1991 | Shioya et al. | 424/447 |
| 5,037,749 | 8/1991 | Findlay | 435/176 |
| 5,039,660 | 8/1991 | Leonard et al. | 514/8 |
| 5,051,272 | 9/1991 | Hermes et al. | 427/2 |
| 5,059,123 | 10/1991 | Jernberg | 433/215 |
| 5,077,049 | 12/1991 | Dunn et al. | 424/426 |
| 5,080,665 | 1/1992 | Jarrett et al. | 606/219 |
| 5,081,106 | 1/1992 | Bentley et al. | 514/5 |
| 5,084,051 | 1/1992 | Törmälä et al. | 606/77 |
| 5,103,840 | 4/1992 | Kavoussi | 128/899 |
| 5,106,626 | 4/1992 | Parsons et al. | 424/423 |
| 5,106,748 | 4/1992 | Wozney et al. | 435/252.3 |
| 5,108,753 | 4/1992 | Kuberasampath et al. | 424/422 |
| 5,108,755 | 4/1992 | Daniels et al. | 424/426 |
| 5,108,922 | 4/1992 | Wang et al. | 435/240.2 |
| 5,110,604 | 5/1992 | Chu et al. | 424/484 |
| 5,116,738 | 5/1992 | Wang et al. | 435/69.1 |
| 5,118,667 | 6/1992 | Adam et al. | 514/12 |
| 5,120,322 | 6/1992 | Davis et al. | 604/265 |
| 5,124,155 | 6/1992 | Reich | 424/428 |
| 5,128,136 | 7/1992 | Bentley et al. | 424/443 |
| 5,128,326 | 7/1992 | Balazs et al. | 514/54 |
| 5,133,755 | 7/1992 | Brekke | 623/16 |
| 5,137,669 | 8/1992 | Leonard et al. | 264/120 |
| 5,141,905 | 8/1992 | Rosen et al. | 435/69.1 |
| 5,143,730 | 9/1992 | Fues et al. | 424/426 |
| 5,162,114 | 11/1992 | Kuberasampath et al. | 424/423 |
| 5,162,430 | 11/1992 | Rhee et al. | 525/54.1 |
| 5,164,368 | 11/1992 | Recker | 514/12 |
| 5,166,058 | 11/1992 | Wang et al. | 435/69.1 |
| 5,168,050 | 12/1992 | Hammonds, Jr. et al. | 435/69.1 |
| 5,171,217 | 12/1992 | March et al. | 604/53 |
| 5,171,574 | 12/1992 | Kuberasampath et al. | 424/423 |
| 5,171,579 | 12/1992 | Ron et al. | 424/486 |
| 5,171,670 | 12/1992 | Kronenberg et al. | 435/68.1 |
| 5,182,365 | 1/1993 | Kuberasmpath et al. | |
| 5,185,152 | 2/1993 | Peyman | 424/427 |
| 5,187,076 | 2/1993 | Wozney et al. | 435/69.1 |
| 5,192,741 | 3/1993 | Orsolini et al. | 514/4 |
| 5,196,185 | 3/1993 | Silver et al. | 424/45 |
| 5,197,977 | 3/1993 | Hoffman, Jr. et al. | 623/1 |
| 5,206,028 | 4/1993 | Li | 424/484 |
| 5,208,041 | 5/1993 | Sindrey | 424/562 |
| 5,208,219 | 5/1993 | Ogawa et al. | 514/12 |
| 5,223,263 | 6/1993 | Hostetler et al. | 424/450 |
| 5,227,157 | 7/1993 | McGinity et al. | 3424/78.02 |
| 5,250,302 | 10/1993 | Oppermann et al. | 424/422 |
| 5,250,584 | 10/1993 | Ikada et al. | 523/114 |
| 5,258,494 | 11/1993 | Oppermann et al. | 530/326 |
| 5,263,985 | 11/1993 | Bao et al. | 623/16 |
| 5,264,618 | 11/1993 | Felgner et al. | 560/224 |
| 5,266,683 | 11/1993 | Oppermann et al. | 530/326 |
| 5,268,178 | 12/1993 | Calhoun et al. | 424/426 |
| 5,270,300 | 12/1993 | Hunziker | 514/12 |
| 5,271,961 | 12/1993 | Mathiowitz et al. | 427/213.31 |
| 5,273,964 | 12/1993 | Lemons | 514/2 |
| 5,275,826 | 1/1994 | Badylak et al. | 424/551 |
| 5,278,201 | 1/1994 | Dunn et al. | 523/113 |
| 5,278,202 | 1/1994 | Dunn et al. | 523/113 |
| 5,281,419 | 1/1994 | Tuan et al. | 424/426 |
| 5,281,422 | 1/1994 | Badylak | 424/551 |
| 5,286,634 | 2/1994 | Stadler et al. | 435/172.3 |
| 5,288,496 | 2/1994 | Lewis | 424/426 |
| 5,292,802 | 3/1994 | Rhee et al. | 525/54.1 |
| 5,306,303 | 4/1994 | Lynch | 623/16 |
| 5,308,623 | 5/1994 | Fues et al. | 424/426 |
| 5,308,889 | 5/1994 | Rhee et al. | |
| 5,317,010 | 5/1994 | Pang et al. | 514/12 |
| 5,320,624 | 6/1994 | Kaplan et al. | 606/77 |
| 5,324,307 | 6/1994 | Jarrett et al. | 6065/219 |
| 5,324,519 | 6/1994 | Dunn et al. | 3424/426 |
| 5,324,520 | 6/1994 | Dunn et al. | 424/435 |
| 5,324,775 | 6/1994 | Rhee et al. | 525/54.2 |
| 5,324,819 | 6/1994 | Oppermann et al. | 530/350 |
| 5,326,350 | 7/1994 | Li | 523/11 |
| 5,326,357 | 7/1994 | Kandel | 623/16 |
| 5,328,955 | 7/1994 | Rhee et al. | 525/54.1 |
| 5,344,654 | 9/1994 | Rueger et al. | 424/423 |
| 5,350,580 | 9/1994 | Muchow et al. | 424/437 |
| 5,352,463 | 10/1994 | Badylak et al. | 424/551 |
| 5,354,557 | 10/1994 | Oppermann et al. | 424/423 |
| 5,360,610 | 11/1994 | Tice et al. | 424/426 |
| 5,366,508 | 11/1994 | Brekke | 623/16 |
| 5,366,733 | 11/1994 | Brizzolara et al. | 424/426 |
| 5,366,734 | 11/1994 | Hutchinson | 424/426 |
| 5,366,875 | 11/1994 | Wozney et al. | 435/69.1 |
| 5,372,821 | 12/1994 | Badylak et al. | 424/551 |
| 5,445,833 | 8/1995 | Badylak et al. | 424/551 |

OTHER PUBLICATIONS

Gunasekaran, S. et al., "Mineralized Collagen as a Substitute for Autograft Bone that Can Deliver Bone Morphogenic Protein", *The 19th Annual Meeting of the Society for Biomaterials*, p. 253, 1993.

Rosen and Thies, "The BMP proteins in bone formation and repair," *Trends in Genetics*, 8(3):97–102, Mar., 1992.

International Search Report dated Sep. 15, 1995.

Agarwala, Neena, et al., "Specific Binding of Parathyroid Hormone to Living Osteoclasts", *Journal of Bone and Mineral Research*, 7:531–539, 1992.

Bonadio et al., "Transgenic mouse model of the mild dominant form of osteogenesis imperfecta," *Proc. Natl. Acad. Sci. USA*, 87:7145–7149, 1990.

Davidson et al., "A model system for in vivo gene transfer into the central nervous system using as adenoviral vector," *Nature Genetics*, 3:219–233, 1993.

Falcone et al., "Macrophage and Foam Cell Release of Matrix–bound Growth factors," *The Journal of Biological Chemistry*, 268:11951–11958, 1993.

Flaumenhaft et al., "Role of the Latent TGF-β Binding Protein in the Activation of Latent TGF-β by Co–Cultures of Endothelial and Smooth Muscle Cells," *The Journal of Cell Biology*, 120(4):995–1002, 1993.

Majmudar et al., "Bone Cell Culture in a Three–Dimensional Polymer Bead Stabilizes the Differentiated Phenotype and Provides Evidence That Osteoblastic Cells Synthesize Type III Collagen and Fibronectin," *Journal of Bone and Mineral Research*, 6(8):869–881, 1991.

Miyazono et al., "Retention of the Transforming Growth Factor–β1 Precursor in the Golgi Complex in a Latent Endoglycosidase H–sensitive Form," *The Journal of Biological Chemistry*, 267(8):5668–5675, 1992.

Pereira et al., "Genomic organization of the sequence coding for fibrillin, the defective gene product in Marfan syndrome," *Human Molecular Genetics*, 2(7):961–968, 1993.

Seitz et al., "Effect of Transforming Growth Factor β on Parathyroid Hormone Receptor Binding and cAMP Formation in Rat Osteosarcoma Cells", *Journal of Bone and Mineral Research*, 7:541–546, 1992.

Selander–Sunnerhagen et al., "How an Epidermal Growth Factor (EGF)–like Domain Binds Calcium," *The Journal of Biological Chemistry*, 267(27):19642–19649, 1992.

Steiner et al., "The New Enzymology of Precursor Processing Endoproteases," *The Journal of Biological Chemistry*, 267(33):23435–23438, 1992.

Stratford–Perricaudet et al., "Widespread Long–term Gene Transfer to Mouse Skeletal Muscles and Heart," *J. Clin. Invest.*, 90:626–630, 1992.

Gunasekaran, S., et al., "Role of Mineralized Collagen as an Osteoconductive Biomaterial", *The 19th Annual Meeting of the Society for Biomaterials*, p. 161, 1993.

Gunasekaran, S., et al., "Mineralization of Collagen Without Nucleating Proteins", 11:30 A.M. V7.5, p. 426.

Horowitz, Mark C., et al., "Functional and Molecular Changes in Colony Stimulating Factor Secretion by Osteoblasts", *Connective Tissue Research*, 20:159–168, 1989.

Huggins, C.B., et al., "Experiments on the Theory of Osteogensis", *Arch. Surg.*, 32(6):915–931, 1936.

Izumi, Toshihiro, et al., "Transforming Growth Factor β1 Stimulates Type II Collagen Expression in Cultured Periosteum–Derived Cells", *J. Bone Miner. Res.*, 7(1):115–121, 1992.

Jingushi, Seiya, et al., "Genetic Expression of Extracellular Matrix Proteins Correlates with Histologic Changes During Fracture Repair", *J. Bone Miner. Res.*, 7(9):1045–1055, 1992.

Jingushi, S., et al., "Acidic Fibroblast Growth Factor (aFGF) Injection Stimulates Cartilage Enlargement and Inhibits Cartilage Gene Expression in Rat Fracture Healing", *J. Ortho. Res.*, 8:364–371, 1990.

Joyce, Michael E., et al., "Role of Growth Factors in Fracture Healing", *Clinical and experimental Approaches to Dermal and Epidermal Repair: Normal and Chronic Wounds*, 391–416, 1991.

Joyce, Michael E., et al., "Transforming Growth Factor–β and the Initiation of Chondrogenesis and Osteogenesis in the Rat Femur", *The J. Cell Biol.*, 110:2195–2207, 1990.

Luyten, Frank P., et al., "Purification and Partial amino Acid Sequence of Osteogenin, a Protein Initiating Bone Differentiation", *J. Biol Chem.*, 264(23):13377–13380, 1989.

O'Malley, Jr. and Ledley "Somatic Gene Therapy in Otolaryngology–Head and Neck Surgery", *Arch Otolaryngol Head Neck Surg*, 119:1191–1197, 1993.

Ozkaynak, Engin, et al., "OP–1 cDNA Encodes as Osteogenic Protein in the TGF–β Family", *EMBO J.*, 9(7):2085–2093, 1990.

Paralkar, Vishwas M., et al., "Identification and Characterization of Cellular Binding Proteins (Receptors) for Recombinant Human Bone Morphogenetic Protein 2B, an Initiator of Bone Differentiation Cascade", *Proc. Natl. Acad. Sci. USA*, 88:3397–3401, 1991.

Roessier, Blake J., et al., "Adenoviral–mediated Gene Transfer to Rabbit Synovium In Vivo", *J. Clin. Invest.*, 92:1085–1092, 1993.

Rosen, Vicki, et al., "Purification and Molecular Cloning of a Novel Group of BMPS and Localization of BMP MRNA in Developing Bone".*Connect. Tissue Res.*, 20:313–319, 1989.

Sampath, T.K., et al., "In Vitro Transformation of Mesenchymal Cells Derived From Embryonic Muscle into Cartilage in Response to Extracellular Matrix Components of Bone", *Proc. Natl. Acad. Sci USA*, 81:3419–3423, 1984.

Sampath and Reddi, "Dissociative Extraction and Reconstitution of Extracellular Matrix Components Involved in Local Bone Differentiation", *Proc. Natl. Acad. Sci. USA*, 78(12):7599–7603, 1981.

Sandusky, G.E., Jr. et al., "Histologic Findings After In Vivo Placement of Small Intestine Submucosal Vacsular Grafts and Saphenous Vein Grafts in the Caroltid Artery in Dogs", *American Journal of Pathology*, 140(2):317–324, 1992.

Shimell, Mary Jane, et al., "The Drosophila Dorsal–Ventral Patterning Gene tolloid is Related to Human Bone Morphogenetic Protein 1", *Cell*, 67:469–481, 1991.

Srivastava, Carolyn H., et al., "Construction of a Recombinant Human Parvovirus B19: Adenoasociated Virus 2(AAV) DNA Inverted Terminal Repeats are Functional in an AAV–B19 Hybrid Virus", *Proc. Natl. Acad. Sci. USA*, 86:8078–8082, 1989.

Toriumi, Dean M., et al., "Mandibular Reconstruction With a Recombinant Bone–Inducing Factor", *Arch Otolaryngol Head Neck Surg*, 117:1101–1112, 1991.

Ulmer, Jeffrey B., et al., "Heterologous Protection Against Influenza by Injection of DNA Encoding a Viral Protein", *Science*, 259:1745–1749, 1993.

Urist, Marshall R., et al., "Bone Cell Differentiation Growth Factors", *Science*, 220:680–220, 1983.

Urist, Marshall R., "Bone: Formation by Autoinduction", *Science*, 150:893–899, 1965.

Wang, Elizabeth A., et al., "Recombinant Human Bone Morphogenetic Protein Induces Bone Formation", *Proc. Natl. Acad. Sci. USA*, 87:2220–2224, 1990.

Wilson, James M., et al., "Somatic Gene Transfer in the Development of an Animal Model for Primary Hyperparathyroidism", *Endocrinology*, 130(5):2947–2954, 1992.

Wolff, Jon A., et al., "Direct Gene Transfer into Mouse Muscle In Vivo", *Science*, 247:1465–1468, 1990.

Wozney, John M., et al., "Novel Regulators of Bone Formation: Molecular Clones and Activities", *Science*, 242:1528–1534, 1988.

Yasko, Alan., et al., "The Healing of Segmental Bone Defects, Induced by Recombinant Human Bone Morphogenetic Protein (rhBMP–2)", *The Journal of Bone and Joint Surgery*, 74–A(5):659–670, 1992.

Badylak et al., "Directed Connective Tissue Remodeling Upon a Biologic Collagen Substrate," *J. Cell Biochem. Supplement* 16F, p. 124, Apr. 3–16, 1992.

Benevisty and Reshef, "Direct introduction of genes into rats and expression of the genes," *Proc. Natl. Acad. Sci. USA*, 83:9551–9555, Dec. 1986.

Bonadio and Goldstein, "Direct Gene Transfer into Skeletal Tissues In Vivo," *Gene Therapy Meeting: Cold Spring Harbor*, Conference Abstract, Sep. 21–25, 1994.

Edelman et al., "c–myc in Vasculoproliferative Disease," *Circulation Research*, 76(2):1.2–1.8, Feb. 1995.

Evans and Robbins, "Possible Orthopaedic Applications of Gene Therapy," *The Journal of Bone and Joint Surgery*, 77–A(7):1103–1114, Jul., 1995.

Indolfi et al., "Inhibition of cellular *ras* prevents smooth muscle cell proliferation after vascular injury *in vivo*," *Nature Medicine*, 1(6):541–545, Jun., 1995.

Invention Disclosure entitled "Small Intenstinal Submucosa as Biomaterial to Promote Gene Therapy," Stephen G. Badylak, Jeffrey Bonadio and Sherry L. Voytik, Sep. 4, 1992.

Kaneda et al., "Increased Expression of DNA Cointroduced with Nuclear Protein in Adult Rat Liver," *Science*, 243:375–378, Jan., 1989.

Mannino and Gould–Fogerite, "Liposome Mediated Gene Transfer," *BioTechniques*, 6(7):682–690, 1988.

Mumper et al., "Interactive Polymeric Gene Delivery Systems for Enhanced Muscle Expression," *Abstract*, American Assoc. of Pharmaceutical Science, Miami Beach, FL, Nov. 6–9, 1995.

Nicolau et al., "*In vivo* expression of rat insulin after intravenous administration of the liposome–entrapped gene for rat insulin," *Proc. Natl. Acad. Sci. USA*, 80:1068–1072, Feb., 1983.

Simons et al., "Antisense c–myb oligonucleotides inhibit intimal arterial smooth muscle cell accumulation *in vivo*," *Nature*, 359:67–70, Sep., 1992.

Sumner et al., "Enhancement of Bone Ingrowth by Transforming Growth Factor–$\beta$," *The Journal of Bone and Joint Surgery*, 77–A(8):1135–1147, Aug., 1995.

Wolff et al., "Conditions Affecting Direct Gene Transfer into Rodent Muscle *In Vivo*," *BioTechniques*, 11(4): 474–485, 1991.

Wolff et al., "Expression of naked plasmids by cultured myotubes and entry of plasmids into T tubules and caveolae of mammalian skeletal muscle," *Journal of Cell Science*, 103:1249–1259, 1992.

Wu and Wu, "Receptor–mediated Gene Delivery and Expression *in Vivo*," *The Journal of Biological Chemistry*, 263(29):14621–14624, 1988.

Yin et al., "Molecular Cloning of a Novel Fibrillin–Like cDNA: Expression in Callus Tissue as Alternatively Spliced Transcripts," *40th Annual Meeting, Orthopaedic Research Society*, Conference Abstract, Feb. 21–24, 1994.

Zhu et al., "Directed Gene Transfer into Regenerating Achilles' Tendon," *40th Annual Meeting, Orthopaedic Research Society*, Conference Abstract, Feb. 21–24, 1994.

U.S. Patent Application Serial No. 08/176,565; filed Jan. 3, 1994; entitled "Fluidized Intestinal Submucosa and its Use as an Injectable Tissue Graft".

U.S. Patent Application Serial No. 08/343,204; filed Nov. 22, 1994; entitled "Fluidized Intestinal Submucosa and its Use as an Injectable Tissue Graft".

U.S. Patent Application Serial No. 08/390,700; filed Feb. 17, 1995; entitled "Compositions and Method for Production of Transformed Cells".

U.S. Patent Application Serial No. 08/386,432; filed Feb. 10, 1995; entitled "Bone Graft Composition".

U.S. Patent Application Serial No. 08/386,452; filed Feb. 10, 1995; entitled "Submucosa as a Growth Substrate for Cells".

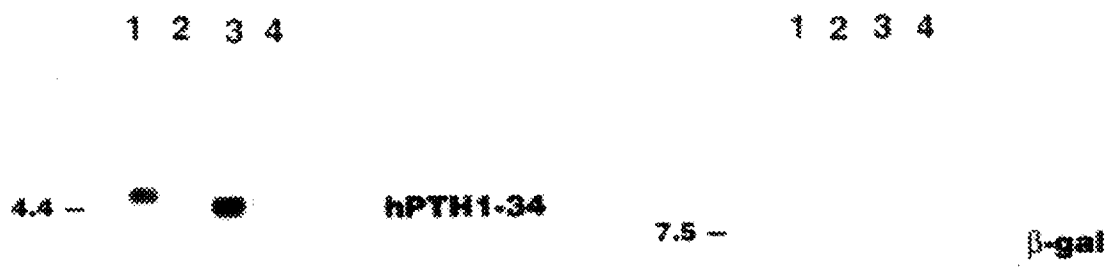
FIGURE 4A
FIGURE 4B
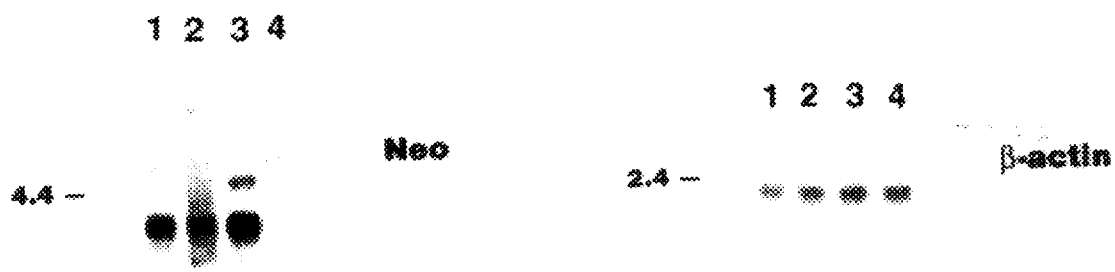
FIGURE 4C
FIGURE 4D

```
MIPGNRMLMV  VLLCQVLLGG  ATDASLMPET  GKKKVAEIQG  HAGGRRSGQS  HELLRDFEAT  LLQMFGLRRR
PQPSKSAVIP  DYMSDLYRLQ  SGEEEEEQS   QGTGLEYPER  PASSANTVSS  FHHEEHLENI  PGTSESSAFR
FFFNLSSIPE  NEVISSAELR  LFREQVDQGP  DWEQGFHRMN  IYEVMKPPAE  MVPGHLITRL  LDTSLVRHNV
TRWETFDVSP  AVLRWTREKQ  PNYGLAIEVT  HLHQTRTHQG  QHVSISRSLP  QGSGNWAQLR  PLLVTFGHDG
RGHTLTRRSA  KRSPKHHPQR  SSKKNKNCRR  HSLYVDFSDV  GWNDWIVAPP  GYQAFYCHGD  CPFPLADHLN
STNHAIVQTL  VNSVNSSIPK  ACCVPTELSA  ISMLYLDEYD  KVVLKNYQEM  VVEGCGCRYP  YDVPDYA

SEQ ID NO:1

FIGURE 9
```

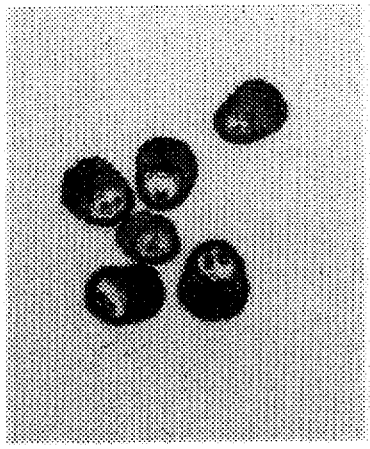
FIGURE 13A　　FIGURE 13B　　FIGURE 13C
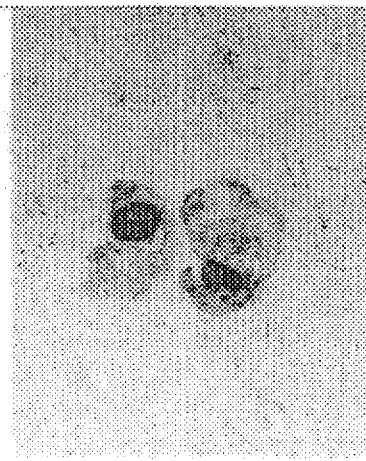
FIGURE 13D　　FIGURE 13E　　FIGURE 13F

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 417 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Met Ile Pro Gly Asn Arg Met Leu Met Val Val Leu Leu Cys Gln Val
 1               5                  10                  15
Leu Leu Gly Gly Ala Thr Asp Ala Ser Leu Met Pro Glu Thr Gly Lys
            20                  25                  30
Lys Lys Val Ala Glu Ile Gln Gly His Ala Gly Gly Arg Arg Ser Gly
        35                  40                  45
Gln Ser His Glu Leu Leu Arg Asp Phe Glu Ala Thr Leu Leu Gln Met
    50                  55                  60
Phe Gly Leu Arg Arg Arg Pro Gln Pro Ser Lys Ser Ala Val Ile Pro
65                  70                  75                  80
Asp Tyr Met Ser Asp Leu Tyr Arg Leu Gln Ser Gly Glu Glu Glu Glu
                85                  90                  95
Glu Glu Gln Ser Gln Gly Thr Gly Leu Glu Tyr Pro Glu Arg Pro Ala
            100                 105                 110
Ser Ser Ala Asn Thr Val Ser Ser Phe His His Glu Glu His Leu Glu
        115                 120                 125
Asn Ile Pro Gly Thr Ser Glu Ser Ser Ala Phe Arg Phe Phe Phe Asn
    130                 135                 140
Leu Ser Ser Ile Pro Glu Asn Glu Val Ile Ser Ser Ala Glu Leu Arg
145                 150                 155                 160
Leu Phe Arg Glu Gln Val Asp Gln Gly Pro Asp Trp Glu Gln Gly Phe
                165                 170                 175
His Arg Met Asn Ile Tyr Glu Val Met Lys Pro Pro Ala Glu Met Val
            180                 185                 190
Pro Gly His Leu Ile Thr Arg Leu Leu Asp Thr Ser Leu Val Arg His
        195                 200                 205
Asn Val Thr Arg Trp Glu Thr Phe Asp Val Ser Pro Ala Val Leu Arg
    210                 215                 220
Trp Thr Arg Glu Lys Gln Pro Asn Tyr Gly Leu Ala Ile Glu Val Thr
225                 230                 235                 240
His Leu His Gln Thr Arg Thr His Gln Gly Gln His Val Ser Ile Ser
                245                 250                 255
Arg Ser Leu Pro Gln Gly Ser Gly Asn Trp Ala Gln Leu Arg Pro Leu
            260                 265                 270
```

| | | | | | | | | | | | | | | |
|---|---|---|---|---|---|---|---|---|---|---|---|---|---|---|
| Leu | Val | Thr 275 | Phe | Gly | His | Asp | Gly 280 | Arg | Gly | His | Thr 285 | Leu | Thr | Arg | Arg |
| Ser | Ala 290 | Lys | Arg | Ser | Pro 295 | Lys | His | His | Pro | Gln 300 | Arg | Ser | Ser | Lys | Lys |
| Asn 305 | Lys | Asn | Cys | Arg | Arg 310 | His | Ser | Leu | Tyr | Val 315 | Asp | Phe | Ser | Asp | Val 320 |
| Gly | Trp | Asn | Asp | Trp 325 | Ile | Val | Ala | Pro | Pro 330 | Gly | Tyr | Gln | Ala | Phe 335 | Tyr |
| Cys | His | Gly | Asp 340 | Cys | Pro | Phe | Pro | Leu 345 | Ala | Asp | His | Leu | Asn 350 | Ser | Thr |
| Asn | His | Ala 355 | Ile | Val | Gln | Thr | Leu 360 | Val | Asn | Ser | Val | Asn 365 | Ser | Ser | Ile |
| Pro | Lys 370 | Ala | Cys | Cys | Val | Pro 375 | Thr | Glu | Leu | Ser | Ala 380 | Ile | Ser | Met | Leu |
| Tyr 385 | Leu | Asp | Glu | Tyr | Asp 390 | Lys | Val | Val | Leu | Lys 395 | Asn | Tyr | Gln | Glu | Met 400 |
| Val | Val | Glu | Gly | Cys 405 | Gly | Cys | Arg | Tyr | Pro 410 | Tyr | Asp | Val | Pro | Asp 415 | Tyr |
| Ala | | | | | | | | | | | | | | | |

(2) INFORMATION FOR SEQ ID NO:2:

(i) SEQUENCE CHARACTERISTICS:
        (A) LENGTH: 4314 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 157..3912

(xi) SEQUENCE DESCRIPTION: SEQ ID NO:2:

```
CCTCCTGCTG TCCCCTCCCT ACCCTTGGCT TCTCGCCCCG CTCTGCCCTC TGCTACCAAC        60

ACTCGATCCC CTGCTCGGGC TCGACCTCCA ATCTCCGAGG GTCGTGCGGC CCCGGATGCC       120

CGGGCCCCGA GCGGTGCCCA CGGCCTGGCC CCTGCG ATG CGC CAG GCC GGC GGA        174
                                         Met Arg Gln Ala Gly Gly
                                           1               5

TTG GGG CTG CTG GCA CTA CTC CTG CTG GCG CTG CTG GGC CCC GGC GGC        222
Leu Gly Leu Leu Ala Leu Leu Leu Leu Ala Leu Leu Gly Pro Gly Gly
         10                  15                  20

CGA GGG GTG GGC CGG CCG GGC AGC GGG GCA CAG GCG GGG GCG GGG CGC        270
Arg Gly Val Gly Arg Pro Gly Ser Gly Ala Gln Ala Gly Ala Gly Arg
             25                  30                  35

TGG GCC CAA CGC TTC AAG GTG GTC TTT GCG CCT GTG ATC TGC AAG CGG        318
Trp Ala Gln Arg Phe Lys Val Val Phe Ala Pro Val Ile Cys Lys Arg
     40                  45                  50

ACC TGT CTG AAG GGC CAG TGT CGG GAC AGC TGT CAG CAG GGC TCC AAC        366
Thr Cys Leu Lys Gly Gln Cys Arg Asp Ser Cys Gln Gln Gly Ser Asn
 55                  60                  65                  70

ATG ACG CTC ATC GGA GAG AAC GGC CAC AGC ACC GAC ACG CTC ACC GGT        414
Met Thr Leu Ile Gly Glu Asn Gly His Ser Thr Asp Thr Leu Thr Gly
                 75                  80                  85

TCT GCC TTC CGC GTG GTG GTG TGC CCT CTA CCC TGC ATG AAC GGT GGC        462
Ser Ala Phe Arg Val Val Val Cys Pro Leu Pro Cys Met Asn Gly Gly
                 90                  95                 100

CAG TGC TCT TCC CGA AAC CAG TGC CTG TGT CCC CCG GAT TTC ACG GGG        510
```

|     |     |     |     |     |     |     |     |     |     |     |     |     |     |     |     |
| --- | --- | --- | --- | --- | --- | --- | --- | --- | --- | --- | --- | --- | --- | --- | --- |
| Gln | Cys | Ser | Ser | Arg | Asn | Gln | Cys | Leu | Cys | Pro | Pro | Asp | Phe | Thr | Gly |
|     |     | 105 |     |     |     | 110 |     |     |     |     | 115 |     |     |     |     |

| CGC | TTC | TGC | CAG | GTG | CCT | GCT | GCA | GGA | ACC | GGA | GCT | GGC | ACC | GGG | AGT | 558 |
| Arg | Phe | Cys | Gln | Val | Pro | Ala | Ala | Gly | Thr | Gly | Ala | Gly | Thr | Gly | Ser |     |
|     | 120 |     |     |     | 125 |     |     |     |     | 130 |     |     |     |     |     |     |

| TCA | GGC | CCC | GGC | TGG | CCC | GAC | CGG | GCC | ATG | TCC | ACA | GGC | CCG | CTG | CCG | 606 |
| Ser | Gly | Pro | Gly | Trp | Pro | Asp | Arg | Ala | Met | Ser | Thr | Gly | Pro | Leu | Pro |     |
| 135 |     |     |     | 140 |     |     |     |     | 145 |     |     |     |     | 150 |     |     |

| CCC | CTT | GCC | CCA | GAA | GGA | GAG | TCT | GTG | GCT | AGC | AAA | CAC | GCC | ATT | TAC | 654 |
| Pro | Leu | Ala | Pro | Glu | Gly | Glu | Ser | Val | Ala | Ser | Lys | His | Ala | Ile | Tyr |     |
|     |     |     |     | 155 |     |     |     |     | 160 |     |     |     |     | 165 |     |     |

| GCG | GTG | CAG | GTG | ATC | GCA | GAT | CCT | CCC | GGG | CCG | GGG | GAG | GGT | CCT | CCT | 702 |
| Ala | Val | Gln | Val | Ile | Ala | Asp | Pro | Pro | Gly | Pro | Gly | Glu | Gly | Pro | Pro |     |
|     |     | 170 |     |     |     |     | 175 |     |     |     |     | 180 |     |     |     |     |

| GCA | CAA | CAT | GCA | GCC | TTC | TTG | GTG | CCC | CTG | GGG | CCA | GGA | CAA | ATC | TCG | 750 |
| Ala | Gln | His | Ala | Ala | Phe | Leu | Val | Pro | Leu | Gly | Pro | Gly | Gln | Ile | Ser |     |
|     |     | 185 |     |     |     |     | 190 |     |     |     |     | 195 |     |     |     |     |

| GCA | GAA | GTG | CAG | GCT | CCG | CCC | CCC | GTG | GTG | AAC | GTG | CGT | GTC | CAT | CAC | 798 |
| Ala | Glu | Val | Gln | Ala | Pro | Pro | Pro | Val | Val | Asn | Val | Arg | Val | His | His |     |
|     | 200 |     |     |     |     | 205 |     |     |     |     | 210 |     |     |     |     |     |

| CCT | CCT | GAA | GCT | TCC | GTT | CAG | GTG | CAC | CGC | ATC | GAG | GGG | CCG | AAC | GCT | 846 |
| Pro | Pro | Glu | Ala | Ser | Val | Gln | Val | His | Arg | Ile | Glu | Gly | Pro | Asn | Ala |     |
| 215 |     |     |     |     | 220 |     |     |     |     | 225 |     |     |     |     | 230 |     |

| GAA | GGC | CCA | GCC | TCT | TCC | CAG | CAC | TTG | CTG | CCG | CAT | CCC | AAG | CCC | CCG | 894 |
| Glu | Gly | Pro | Ala | Ser | Ser | Gln | His | Leu | Leu | Pro | His | Pro | Lys | Pro | Pro |     |
|     |     |     |     | 235 |     |     |     |     | 240 |     |     |     |     | 245 |     |     |

| CAC | CCG | AGG | CCA | CCC | ACT | CAA | AAG | CCA | CTG | GGC | CGC | TGC | TTC | CAG | GAC | 942 |
| His | Pro | Arg | Pro | Pro | Thr | Gln | Lys | Pro | Leu | Gly | Arg | Cys | Phe | Gln | Asp |     |
|     |     |     | 250 |     |     |     |     | 255 |     |     |     |     | 260 |     |     |     |

| ACA | TTG | CCC | AAG | CAG | CCT | TGT | GGC | AGC | AAC | CCT | TTG | CCT | GGC | CTT | ACC | 990 |
| Thr | Leu | Pro | Lys | Gln | Pro | Cys | Gly | Ser | Asn | Pro | Leu | Pro | Gly | Leu | Thr |     |
|     |     | 265 |     |     |     |     | 270 |     |     |     |     | 275 |     |     |     |     |

| AAG | CAG | GAA | GAT | TGC | TGC | GGT | AGC | ATC | GGT | ACT | GCC | TGG | GGA | CAA | AGC | 1038 |
| Lys | Gln | Glu | Asp | Cys | Cys | Gly | Ser | Ile | Gly | Thr | Ala | Trp | Gly | Gln | Ser |     |
|     | 280 |     |     |     |     | 285 |     |     |     |     | 290 |     |     |     |     |     |

| AAG | TGT | CAC | AAG | TGC | CCA | CAG | CTT | CAG | TAT | ACA | GGG | GTG | CAG | AAG | CCT | 1086 |
| Lys | Cys | His | Lys | Cys | Pro | Gln | Leu | Gln | Tyr | Thr | Gly | Val | Gln | Lys | Pro |     |
| 295 |     |     |     |     | 300 |     |     |     |     | 305 |     |     |     |     | 310 |     |

| GTA | CCT | GTA | CGT | GGG | GAG | GTG | GGT | GCT | GAC | TGC | CCC | CAG | GGC | TAC | AAG | 1134 |
| Val | Pro | Val | Arg | Gly | Glu | Val | Gly | Ala | Asp | Cys | Pro | Gln | Gly | Tyr | Lys |     |
|     |     |     |     | 315 |     |     |     |     | 320 |     |     |     |     | 325 |     |     |

| AGG | CTC | AAC | AGC | ACC | CAC | TGC | CAG | GAT | ATC | AAC | GAA | TGT | GCG | ATG | CCC | 1182 |
| Arg | Leu | Asn | Ser | Thr | His | Cys | Gln | Asp | Ile | Asn | Glu | Cys | Ala | Met | Pro |     |
|     |     |     | 330 |     |     |     |     | 335 |     |     |     |     | 340 |     |     |     |

| GGG | AAT | GTG | TGC | CAT | GGT | GAC | TGC | CTC | AAC | AAC | CCT | GGC | TCT | TAT | CGC | 1230 |
| Gly | Asn | Val | Cys | His | Gly | Asp | Cys | Leu | Asn | Asn | Pro | Gly | Ser | Tyr | Arg |     |
|     |     | 345 |     |     |     |     | 350 |     |     |     |     | 355 |     |     |     |     |

| TGT | GTC | TGC | CCG | CCC | GGT | CAT | AGC | TTG | GGT | CCC | CTC | GCA | GCA | CAG | TGC | 1278 |
| Cys | Val | Cys | Pro | Pro | Gly | His | Ser | Leu | Gly | Pro | Leu | Ala | Ala | Gln | Cys |     |
|     | 360 |     |     |     |     | 365 |     |     |     |     | 370 |     |     |     |     |     |

| ATT | GCC | GAC | AAA | CCA | GAG | GAG | AAG | AGC | CTG | TGT | TTC | CGC | CTT | GTG | AGC | 1326 |
| Ile | Ala | Asp | Lys | Pro | Glu | Glu | Lys | Ser | Leu | Cys | Phe | Arg | Leu | Val | Ser |     |
| 375 |     |     |     |     | 380 |     |     |     |     | 385 |     |     |     |     | 390 |     |

| ACC | GAA | CAC | CAG | TGC | CAG | CAC | CCT | CTG | ACC | ACA | CGC | CTA | ACC | CGC | CAG | 1374 |
| Thr | Glu | His | Gln | Cys | Gln | His | Pro | Leu | Thr | Thr | Arg | Leu | Thr | Arg | Gln |     |
|     |     |     |     | 395 |     |     |     |     | 400 |     |     |     |     | 405 |     |     |

| CTC | TGC | TGC | TGT | AGT | GTG | GGT | AAA | GCC | TGG | GGT | GCC | CGG | TGC | CAG | CGC | 1422 |
| Leu | Cys | Cys | Cys | Ser | Val | Gly | Lys | Ala | Trp | Gly | Ala | Arg | Cys | Gln | Arg |     |
|     |     |     | 410 |     |     |     |     | 415 |     |     |     |     | 420 |     |     |     |

| TGC | CCG | GCA | GAT | GGT | ACA | GCA | GCC | TTC | AAG | GAG | ATC | TGC | CCC | GGC | TGG | 1470 |

```
Cys Pro Ala Asp Gly Thr Ala Ala Phe Lys Glu Ile Cys Pro Gly Trp
        425                 430                 435

GAA AGG GTA CCA TAT CCT CAC CTC CCA CCA GAC GCT CAC CAT CCA GGG      1518
Glu Arg Val Pro Tyr Pro His Leu Pro Pro Asp Ala His His Pro Gly
    440                 445                 450

GGA AAG CGA CTT CTC CCT CTT CCT GCA CCC GAC GGG CCA CCC AAA CCC      1566
Gly Lys Arg Leu Leu Pro Leu Pro Ala Pro Asp Gly Pro Pro Lys Pro
455                 460                 465                 470

CAG CAG CTT CCT GAA AGC CCC AGC CGA GCA CCA CCC CTC GAG GAC ACA      1614
Gln Gln Leu Pro Glu Ser Pro Ser Arg Ala Pro Pro Leu Glu Asp Thr
                    475                 480                 485

GAG GAA GAG AGA GGA GTG ACC ATG GAT CCA CCA GTG AGT GAG GAG CGA      1662
Glu Glu Glu Arg Gly Val Thr Met Asp Pro Pro Val Ser Glu Glu Arg
            490                 495                 500

TCG GTG CAG CAG AGC CAC CCC ACT ACC ACC ACC TCA CCC CCC CGG CCT      1710
Ser Val Gln Gln Ser His Pro Thr Thr Thr Thr Ser Pro Pro Arg Pro
        505                 510                 515

TAC CCA GAG CTC ATC TCT CGC CCC TCC CCA CCT ACC TTC CAC CGG TTC      1758
Tyr Pro Glu Leu Ile Ser Arg Pro Ser Pro Pro Thr Phe His Arg Phe
    520                 525                 530

CTG CCA GAC TTG CCC CCA TCC CGA AGT GCA GTG GAG ATC GCC CCC ACT      1806
Leu Pro Asp Leu Pro Pro Ser Arg Ser Ala Val Glu Ile Ala Pro Thr
535                 540                 545                 550

CAG GTC ACA GAG ACC GAT GAG TGC CGA TTG AAC CAG AAT ATC TGT GGC      1854
Gln Val Thr Glu Thr Asp Glu Cys Arg Leu Asn Gln Asn Ile Cys Gly
                    555                 560                 565

CAT GGA CAG TGT GTG CCT GGC CCC TCG GAT TAC TCC TGC CAC TGC AAC      1902
His Gly Gln Cys Val Pro Gly Pro Ser Asp Tyr Ser Cys His Cys Asn
            570                 575                 580

GCT GGC TAC CGG TCA CAC CCG CAG CAC CGC TAC TGT GTT GAT GTG AAC      1950
Ala Gly Tyr Arg Ser His Pro Gln His Arg Tyr Cys Val Asp Val Asn
        585                 590                 595

GAG TGC GAG GCA GAG CCC TGC GGC CCC GGG AAA GGC ATC TGT ATG AAC      1998
Glu Cys Glu Ala Glu Pro Cys Gly Pro Gly Lys Gly Ile Cys Met Asn
    600                 605                 610

ACT GGT GGC TCC TAC AAT TGT CAC TGC AAC CGA GGC TAC CGC CTC CAC      2046
Thr Gly Gly Ser Tyr Asn Cys His Cys Asn Arg Gly Tyr Arg Leu His
615                 620                 625                 630

GTG GGT GCA GGG GGC CGC TCG TGC GTG GAC CTG AAC GAG TGC GCC AAG      2094
Val Gly Ala Gly Gly Arg Ser Cys Val Asp Leu Asn Glu Cys Ala Lys
                    635                 640                 645

CCT CAC CTG TGT GGG GAC GGT GGC TTC TGC ATC AAC TTC CCT GGT CAC      2142
Pro His Leu Cys Gly Asp Gly Gly Phe Cys Ile Asn Phe Pro Gly His
            650                 655                 660

TAC AAA TGC AAC TGC TAT CCT GGC TAC CGG CTC AAG GCC TCC CGA CCG      2190
Tyr Lys Cys Asn Cys Tyr Pro Gly Tyr Arg Leu Lys Ala Ser Arg Pro
        665                 670                 675

CCC ATT TGC GAA GAC ATC GAC GAG TGT CGC GAC CCT AGC ACC TGC CCT      2238
Pro Ile Cys Glu Asp Ile Asp Glu Cys Arg Asp Pro Ser Thr Cys Pro
    680                 685                 690

GAT GGC AAA TGT GAA AAC AAA CCT GGC AGC TTC AAG TGC ATC GCC TGC      2286
Asp Gly Lys Cys Glu Asn Lys Pro Gly Ser Phe Lys Cys Ile Ala Cys
695                 700                 705                 710

CAG CCT GGC TAC CGT AGC CAG GGG GGC GGG GCC TGT CGT GAT GTC AAC      2334
Gln Pro Gly Tyr Arg Ser Gln Gly Gly Gly Ala Cys Arg Asp Val Asn
                    715                 720                 725

GAA TGC TCC GAA GGT ACC CCC TGC TCT CCT GGA TGG TGT GAG AAA CTT      2382
Glu Cys Ser Glu Gly Thr Pro Cys Ser Pro Gly Trp Cys Glu Lys Leu
            730                 735                 740

CCG GGT TCT TAC CGT TGC ACG TGT GCC CAG GGG ATA CGA ACC CGC ACA      2430
```

|  |  |  |  |  |  |  |  |  |  |  |  |  |  |  |  |
|---|---|---|---|---|---|---|---|---|---|---|---|---|---|---|---|
| Pro | Gly | Ser | Tyr | Arg | Cys | Thr | Cys | Ala | Gln | Gly | Ile | Arg | Thr | Arg | Thr |
|  |  | 745 |  |  |  |  | 750 |  |  |  |  | 755 |  |  |  |

| GGA | CGC | CTC | AGT | TGC | ATA | GAC | GTG | GAT | GAC | TGT | GAG | GCT | GGG | AAA | GTG | 2478 |
|---|---|---|---|---|---|---|---|---|---|---|---|---|---|---|---|---|
| Gly | Arg | Leu | Ser | Cys | Ile | Asp | Val | Asp | Asp | Cys | Glu | Ala | Gly | Lys | Val |  |
|  | 760 |  |  |  | 765 |  |  |  |  | 770 |  |  |  |  |  |  |

| TGC | CAA | GAT | GGC | ATC | TGC | ACG | AAC | ACA | CCA | GGC | TCT | TTC | CAG | TGT | CAG | 2526 |
|---|---|---|---|---|---|---|---|---|---|---|---|---|---|---|---|---|
| Cys | Gln | Asp | Gly | Ile | Cys | Thr | Asn | Thr | Pro | Gly | Ser | Phe | Gln | Cys | Gln |  |
| 775 |  |  |  | 780 |  |  |  |  | 785 |  |  |  |  | 790 |  |  |

| TGC | CTC | TCC | GGC | TAT | CAT | CTG | TCA | AGG | GAT | CGG | AGC | CGC | TGT | GAG | GAC | 2574 |
|---|---|---|---|---|---|---|---|---|---|---|---|---|---|---|---|---|
| Cys | Leu | Ser | Gly | Tyr | His | Leu | Ser | Arg | Asp | Arg | Ser | Arg | Cys | Glu | Asp |  |
|  |  |  |  | 795 |  |  |  |  | 800 |  |  |  | 805 |  |  |  |

| ATT | GAT | GAA | TGT | GAC | TTC | CCT | GCG | GCC | TGC | ATC | GGG | GGT | GAC | TGC | ATC | 2622 |
|---|---|---|---|---|---|---|---|---|---|---|---|---|---|---|---|---|
| Ile | Asp | Glu | Cys | Asp | Phe | Pro | Ala | Ala | Cys | Ile | Gly | Gly | Asp | Cys | Ile |  |
|  |  |  | 810 |  |  |  |  | 815 |  |  |  | 820 |  |  |  |  |

| AAT | ACC | AAT | GGT | TCC | TAC | AGA | TGT | CTC | TGT | CCC | CTG | GGT | CAT | CGG | TTG | 2670 |
|---|---|---|---|---|---|---|---|---|---|---|---|---|---|---|---|---|
| Asn | Thr | Asn | Gly | Ser | Tyr | Arg | Cys | Leu | Cys | Pro | Leu | Gly | His | Arg | Leu |  |
|  |  | 825 |  |  |  |  | 830 |  |  |  |  | 835 |  |  |  |  |

| GTG | GGC | GGC | AGG | AAG | TGC | AAG | AAA | GAT | ATA | GAT | GAG | TGC | AGC | CAG | GAC | 2718 |
|---|---|---|---|---|---|---|---|---|---|---|---|---|---|---|---|---|
| Val | Gly | Gly | Arg | Lys | Cys | Lys | Lys | Asp | Ile | Asp | Glu | Cys | Ser | Gln | Asp |  |
|  | 840 |  |  |  | 845 |  |  |  |  | 850 |  |  |  |  |  |  |

| CCA | GGC | CTG | TGC | CTG | CCC | CAT | GCC | TGC | GAG | AAC | CTC | CAG | GGC | TCC | TAT | 2766 |
|---|---|---|---|---|---|---|---|---|---|---|---|---|---|---|---|---|
| Pro | Gly | Leu | Cys | Leu | Pro | His | Ala | Cys | Glu | Asn | Leu | Gln | Gly | Ser | Tyr |  |
| 855 |  |  |  | 860 |  |  |  |  | 865 |  |  |  |  | 870 |  |  |

| GTC | TGT | GTC | TGT | GAT | GAG | GGT | TTC | ACA | CTC | ACC | CAG | GAC | CAG | CAT | GGG | 2814 |
|---|---|---|---|---|---|---|---|---|---|---|---|---|---|---|---|---|
| Val | Cys | Val | Cys | Asp | Glu | Gly | Phe | Thr | Leu | Thr | Gln | Asp | Gln | His | Gly |  |
|  |  |  |  | 875 |  |  |  |  | 880 |  |  |  |  | 885 |  |  |

| TGT | GAG | GAG | GTG | GAG | CAG | CCC | CAC | CAC | AAG | AAG | GAG | TGC | TAC | CTT | AAC | 2862 |
|---|---|---|---|---|---|---|---|---|---|---|---|---|---|---|---|---|
| Cys | Glu | Glu | Val | Glu | Gln | Pro | His | His | Lys | Lys | Glu | Cys | Tyr | Leu | Asn |  |
|  |  |  | 890 |  |  |  |  | 895 |  |  |  |  | 900 |  |  |  |

| TTC | GAT | GAC | ACA | GTG | TTC | TGT | GAC | AGC | GTA | TTG | GCT | ACC | AAT | GTC | ACT | 2910 |
|---|---|---|---|---|---|---|---|---|---|---|---|---|---|---|---|---|
| Phe | Asp | Asp | Thr | Val | Phe | Cys | Asp | Ser | Val | Leu | Ala | Thr | Asn | Val | Thr |  |
|  |  | 905 |  |  |  |  | 910 |  |  |  |  | 915 |  |  |  |  |

| CAG | CAG | GAA | TGC | TGT | TGC | TCT | CTG | GGA | GCT | GGC | TGG | GGA | GAC | CAC | TGC | 2958 |
|---|---|---|---|---|---|---|---|---|---|---|---|---|---|---|---|---|
| Gln | Gln | Glu | Cys | Cys | Cys | Ser | Leu | Gly | Ala | Gly | Trp | Gly | Asp | His | Cys |  |
| 920 |  |  |  |  | 925 |  |  |  |  | 930 |  |  |  |  |  |  |

| GAA | ATC | TAT | CCC | TGT | CCA | GTC | TAC | AGC | TCA | GCC | GAA | TTT | CAC | AGC | CTG | 3006 |
|---|---|---|---|---|---|---|---|---|---|---|---|---|---|---|---|---|
| Glu | Ile | Tyr | Pro | Cys | Pro | Val | Tyr | Ser | Ser | Ala | Glu | Phe | His | Ser | Leu |  |
| 935 |  |  |  | 940 |  |  |  |  | 945 |  |  |  |  | 950 |  |  |

| GTG | CCT | GAT | GGG | AAA | AGG | CTA | CAC | TCA | GGA | CAA | CAA | CAT | TGT | GAA | CTA | 3054 |
|---|---|---|---|---|---|---|---|---|---|---|---|---|---|---|---|---|
| Val | Pro | Asp | Gly | Lys | Arg | Leu | His | Ser | Gly | Gln | Gln | His | Cys | Glu | Leu |  |
|  |  |  | 955 |  |  |  |  | 960 |  |  |  |  | 965 |  |  |  |

| TGC | ATT | CCT | GCC | CAC | CGT | GAC | ATC | GAC | GAA | TGC | ATA | TTG | TTT | GGG | GCA | 3102 |
|---|---|---|---|---|---|---|---|---|---|---|---|---|---|---|---|---|
| Cys | Ile | Pro | Ala | His | Arg | Asp | Ile | Asp | Glu | Cys | Ile | Leu | Phe | Gly | Ala |  |
|  |  |  | 970 |  |  |  | 975 |  |  |  |  | 980 |  |  |  |  |

| GAG | ATC | TGC | AAG | GAG | GGC | AAG | TGT | GTG | AAC | TCG | CAG | CCC | GGC | TAC | GAG | 3150 |
|---|---|---|---|---|---|---|---|---|---|---|---|---|---|---|---|---|
| Glu | Ile | Cys | Lys | Glu | Gly | Lys | Cys | Val | Asn | Ser | Gln | Pro | Gly | Tyr | Glu |  |
|  |  | 985 |  |  |  |  | 990 |  |  |  |  | 995 |  |  |  |  |

| TGC | TAC | TGC | AAG | CAG | GGC | TTC | TAC | TAC | GAT | GGC | AAC | CTG | CTG | GAG | TGC | 3198 |
|---|---|---|---|---|---|---|---|---|---|---|---|---|---|---|---|---|
| Cys | Tyr | Cys | Lys | Gln | Gly | Phe | Tyr | Tyr | Asp | Gly | Asn | Leu | Leu | Glu | Cys |  |
| 1000 |  |  |  |  | 1005 |  |  |  |  | 1010 |  |  |  |  |  |  |

| GTG | GAC | GTG | GAC | GAG | TGC | TTG | GAT | GAG | TCT | AAC | TGC | AGG | AAC | GGA | GTG | 3246 |
|---|---|---|---|---|---|---|---|---|---|---|---|---|---|---|---|---|
| Val | Asp | Val | Asp | Glu | Cys | Leu | Asp | Glu | Ser | Asn | Cys | Arg | Asn | Gly | Val |  |
| 1015 |  |  |  | 1020 |  |  |  |  | 1025 |  |  |  |  | 1030 |  |  |

| TGT | GAG | AAC | ACG | TGG | CGG | CTA | CCG | TGT | GCC | TGC | ACT | CCG | CCG | GCA | GAG | 3294 |
|---|---|---|---|---|---|---|---|---|---|---|---|---|---|---|---|---|
| Cys | Glu | Asn | Thr | Trp | Arg | Leu | Pro | Cys | Ala | Cys | Thr | Pro | Pro | Ala | Glu |  |
|  |  |  |  | 1035 |  |  |  |  | 1040 |  |  |  |  | 1045 |  |  |

| TAC | AGT | CCC | GCA | CAG | GCC | CAG | TGT | CTG | ATC | CCG | GAG | AGA | TGG | AGC | ACG | 3342 |
|---|---|---|---|---|---|---|---|---|---|---|---|---|---|---|---|---|
| Tyr | Ser | Pro | Ala | Gln | Ala | Gln | Cys | Leu | Ile | Pro | Glu | Arg | Trp | Ser | Thr |  |
|  |  |  | 1050 |  |  |  |  | 1055 |  |  |  |  | 1060 |  |  |  |

| CCC | CAG | AGA | GAC | GTG | AAG | TGT | GCT | GGG | GCC | AGC | GAG | GAG | AGG | ACG | GCA | 3390 |
|---|---|---|---|---|---|---|---|---|---|---|---|---|---|---|---|---|

| | | | | | | | | | | | | | | | |
|---|---|---|---|---|---|---|---|---|---|---|---|---|---|---|---|
| Pro | Gln | Arg | Asp | Val | Lys | Cys | Ala | Gly | Ala | Ser | Glu | Glu | Arg | Thr | Ala |
| | | 1065 | | | | 1070 | | | | | 1075 | | | | |

```
TGT GTA TGG GGC CCC TGG GCG GGA CCT GCC CTC ACT TTT GAT GAC TGC    3438
Cys Val Trp Gly Pro Trp Ala Gly Pro Ala Leu Thr Phe Asp Asp Cys
    1080                1085                1090

TGC TGC CGC CAG CCG CGG CTG GGT ACC CAG TGC AGA CCG TGC CCG CCA    3486
Cys Cys Arg Gln Pro Arg Leu Gly Thr Gln Cys Arg Pro Cys Pro Pro
1095                1100                1105                1110

CGT GGC ACC GGG TCC CAG TGC CCG ACT TCA CAG AGT GAG AGC AAT TCT    3534
Arg Gly Thr Gly Ser Gln Cys Pro Thr Ser Gln Ser Glu Ser Asn Ser
                1115                1120                1125

TTC TGG GAC ACA AGC CCC CTG CTA CTG GGG AAG TCT CCG CGA GAC GAA    3582
Phe Trp Asp Thr Ser Pro Leu Leu Leu Gly Lys Ser Pro Arg Asp Glu
            1130                1135                1140

GAC AGC TCA GAG GAG GAT TCA GAT GAG TGC CGT TGT GTG AGC GGA CCG    3630
Asp Ser Ser Glu Glu Asp Ser Asp Glu Cys Arg Cys Val Ser Gly Pro
        1145                1150                1155

TGT GTG CCA CGG CCA GGC GGG GCG GTA TGC GAG TGT CCT GGA GGC TTT    3678
Cys Val Pro Arg Pro Gly Gly Ala Val Cys Glu Cys Pro Gly Gly Phe
    1160                1165                1170

CAG CTG GAC GCC TCC CGT GCC CGC TGC GTG GAC ATT GAT GAG TGC CGA    3726
Gln Leu Asp Ala Ser Arg Ala Arg Cys Val Asp Ile Asp Glu Cys Arg
1175                1180                1185                1190

GAA CTG AAC CAG CGG GGA CTG CTG TGT AAG AGC GAG CGG TGC GTG AAC    3774
Glu Leu Asn Gln Arg Gly Leu Leu Cys Lys Ser Glu Arg Cys Val Asn
                1195                1200                1205

ACC AGT GGA TCC TTC CGC TGT GTC TGC AAA GCT GGC TTC ACG CGC AGC    3822
Thr Ser Gly Ser Phe Arg Cys Val Cys Lys Ala Gly Phe Thr Arg Ser
            1210                1215                1220

CGC CCT CAC GGG CCT GCG TGC CTC AGC GCC GCC GCT GAT GAT GCA GCC    3870
Arg Pro His Gly Pro Ala Cys Leu Ser Ala Ala Ala Asp Asp Ala Ala
        1225                1230                1235

ATA GCC CAC ACC TCA GTG ATC GAT CAT CGA GGG TAT TTT CAC             3912
Ile Ala His Thr Ser Val Ile Asp His Arg Gly Tyr Phe His
    1240                1245                1250

TGAAAGTGGA GACAGACAAG TACATCCTTT GCTCCTGACC AAACGAGAGC ATGGACCCAA   3972

GGATCCTTCA GGGCCCACAA ATCTCCTTCC CACACCCCAA ACCCAAGGTG CTCCTGTCTG   4032

CAGAGTGCTG TCTGCTTTCT CCCAAGGGTG ATTCCTAGAA ACTTCGACAT CAGATCTGCC   4092

CCTTTAATTT ACTCTTGGCT TTCAAGGCAA ATTGATATTC ACATCCAAAG CGGGCAGCAT   4152

CAACTGCTTG GCGGGTTGGA CTGAGCTGGG ACCCAGGATG TGAAATAGAA TTTATTGTGG   4212

CTCTGATTAT GTACACTAGA TGTGCCTGAC CTGCTGACCA GGCTCACATG GTTTGTACAA   4272

TAAATACATC CGCCGGGAAA AAAAAAAAA AAAAAAAAA AA                        4314
```

( 2 ) INFORMATION FOR SEQ ID NO:3:

( i ) SEQUENCE CHARACTERISTICS:
        ( A ) LENGTH: 1252 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Arg Gln Ala Gly Gly Leu Gly Leu Leu Ala Leu Leu Leu Ala
    1               5                   10                  15

Leu Leu Gly Pro Gly Gly Arg Gly Val Gly Arg Pro Gly Ser Gly Ala
            20                  25                  30

Gln Ala Gly Ala Gly Arg Trp Ala Gln Arg Phe Lys Val Val Phe Ala
```

|  | 35 |  |  |  | 40 |  |  |  | 45 |  |  |  |
|---|---|---|---|---|---|---|---|---|---|---|---|---|

Pro Val Ile Cys Lys Arg Thr Cys Leu Lys Gly Gln Cys Arg Asp Ser
 50                      55                  60

Cys Gln Gln Gly Ser Asn Met Thr Leu Ile Gly Glu Asn Gly His Ser
65                  70                  75                  80

Thr Asp Thr Leu Thr Gly Ser Ala Phe Arg Val Val Cys Pro Leu
                 85                  90                      95

Pro Cys Met Asn Gly Gly Gln Cys Ser Ser Arg Asn Gln Cys Leu Cys
             100                 105                 110

Pro Pro Asp Phe Thr Gly Arg Phe Cys Gln Val Pro Ala Ala Gly Thr
             115                 120                 125

Gly Ala Gly Thr Gly Ser Ser Gly Pro Gly Trp Pro Asp Arg Ala Met
130                      135                 140

Ser Thr Gly Pro Leu Pro Pro Leu Ala Pro Glu Gly Glu Ser Val Ala
145              150              155                      160

Ser Lys His Ala Ile Tyr Ala Val Gln Val Ile Ala Asp Pro Pro Gly
                 165                 170                 175

Pro Gly Glu Gly Pro Pro Ala Gln His Ala Ala Phe Leu Val Pro Leu
             180                 185                 190

Gly Pro Gly Gln Ile Ser Ala Glu Val Gln Ala Pro Pro Val Val
         195                 200                 205

Asn Val Arg Val His His Pro Glu Ala Ser Val Gln Val His Arg
210                      215                 220

Ile Glu Gly Pro Asn Ala Glu Gly Pro Ala Ser Ser Gln His Leu Leu
225              230                 235                     240

Pro His Pro Lys Pro His Pro Arg Pro Thr Gln Lys Pro Leu
             245              250              255

Gly Arg Cys Phe Gln Asp Thr Leu Pro Lys Gln Pro Cys Gly Ser Asn
         260                 265                 270

Pro Leu Pro Gly Leu Thr Lys Gln Glu Asp Cys Cys Gly Ser Ile Gly
         275                 280              285

Thr Ala Trp Gly Gln Ser Lys Cys His Lys Cys Pro Gln Leu Gln Tyr
290                      295                 300

Thr Gly Val Gln Lys Pro Val Pro Val Arg Gly Glu Val Gly Ala Asp
305                  310                 315                 320

Cys Pro Gln Gly Tyr Lys Arg Leu Asn Ser Thr His Cys Gln Asp Ile
             325                 330                 335

Asn Glu Cys Ala Met Pro Gly Asn Val Cys His Gly Asp Cys Leu Asn
             340                 345                 350

Asn Pro Gly Ser Tyr Arg Cys Val Cys Pro Pro Gly His Ser Leu Gly
         355             360                 365

Pro Leu Ala Ala Gln Cys Ile Ala Asp Lys Pro Glu Glu Lys Ser Leu
370                  375                 380

Cys Phe Arg Leu Val Ser Thr Glu His Gln Cys Gln His Pro Leu Thr
385                  390                 395                 400

Thr Arg Leu Thr Arg Gln Leu Cys Cys Cys Ser Val Gly Lys Ala Trp
                 405                 410                 415

Gly Ala Arg Cys Gln Arg Cys Pro Ala Asp Gly Thr Ala Ala Phe Lys
             420                 425                 430

Glu Ile Cys Pro Gly Trp Glu Arg Val Pro Tyr Pro His Leu Pro Pro
         435             440                 445

Asp Ala His His Pro Gly Gly Lys Arg Leu Leu Pro Leu Pro Ala Pro
450                  455                 460

-continued

| | | | | | | | | | | | | | | |
|---|---|---|---|---|---|---|---|---|---|---|---|---|---|---|
| Asp 465 | Gly | Pro | Pro | Lys 470 | Pro | Gln | Gln | Leu | Pro 475 | Glu | Ser | Pro | Ser | Arg | Ala 480 |
| Pro | Pro | Leu | Glu | Asp 485 | Thr | Glu | Glu | Glu | Arg 490 | Gly | Val | Thr | Met | Asp 495 | Pro |
| Pro | Val | Ser | Glu 500 | Glu | Arg | Ser | Val | Gln 505 | Gln | Ser | His | Pro | Thr 510 | Thr | Thr |
| Thr | Ser | Pro 515 | Pro | Arg | Pro | Tyr | Pro 520 | Glu | Leu | Ile | Ser | Arg 525 | Pro | Ser | Pro |
| Pro | Thr 530 | Phe | His | Arg | Phe | Leu 535 | Pro | Asp | Leu | Pro | Pro 540 | Ser | Arg | Ser | Ala |
| Val 545 | Glu | Ile | Ala | Pro | Thr 550 | Gln | Val | Thr | Glu | Thr 555 | Asp | Glu | Cys | Arg | Leu 560 |
| Asn | Gln | Asn | Ile | Cys 565 | Gly | His | Gly | Gln | Cys 570 | Val | Pro | Gly | Pro | Ser 575 | Asp |
| Tyr | Ser | Cys | His 580 | Cys | Asn | Ala | Gly | Tyr 585 | Arg | Ser | His | Pro | Gln 590 | His | Arg |
| Tyr | Cys | Val 595 | Asp | Val | Asn | Glu | Cys 600 | Glu | Ala | Glu | Pro | Cys 605 | Gly | Pro | Gly |
| Lys | Gly 610 | Ile | Cys | Met | Asn | Thr 615 | Gly | Gly | Ser | Tyr | Asn 620 | Cys | His | Cys | Asn |
| Arg 625 | Gly | Tyr | Arg | Leu | His 630 | Val | Gly | Ala | Gly | Gly 635 | Arg | Ser | Cys | Val | Asp 640 |
| Leu | Asn | Glu | Cys | Ala 645 | Lys | Pro | His | Leu | Cys 650 | Gly | Asp | Gly | Phe 655 | Cys |
| Ile | Asn | Phe | Pro 660 | Gly | His | Tyr | Lys | Cys 665 | Asn | Cys | Tyr | Pro | Gly 670 | Tyr | Arg |
| Leu | Lys | Ala 675 | Ser | Arg | Pro | Pro | Ile 680 | Cys | Glu | Asp | Ile | Asp 685 | Glu | Cys | Arg |
| Asp | Pro 690 | Ser | Thr | Cys | Pro | Asp 695 | Gly | Lys | Cys | Glu | Asn 700 | Lys | Pro | Gly | Ser |
| Phe 705 | Lys | Cys | Ile | Ala | Cys 710 | Gln | Pro | Gly | Tyr | Arg 715 | Ser | Gln | Gly | Gly | Gly 720 |
| Ala | Cys | Arg | Asp | Val 725 | Asn | Glu | Cys | Ser | Glu 730 | Gly | Thr | Pro | Cys | Ser 735 | Pro |
| Gly | Trp | Cys | Glu 740 | Lys | Leu | Pro | Gly | Ser 745 | Tyr | Arg | Cys | Thr | Cys 750 | Ala | Gln |
| Gly | Ile | Arg 755 | Thr | Arg | Thr | Gly | Arg 760 | Leu | Ser | Cys | Ile | Asp 765 | Val | Asp | Asp |
| Cys | Glu 770 | Ala | Gly | Lys | Val | Cys 775 | Gln | Asp | Gly | Ile | Cys 780 | Thr | Asn | Thr | Pro |
| Gly 785 | Ser | Phe | Gln | Cys | Gln 790 | Cys | Leu | Ser | Gly | Tyr 795 | His | Leu | Ser | Arg | Asp 800 |
| Arg | Ser | Arg | Cys | Glu 805 | Asp | Ile | Asp | Glu | Cys 810 | Asp | Phe | Pro | Ala | Ala 815 | Cys |
| Ile | Gly | Gly | Asp 820 | Cys | Ile | Asn | Thr | Asn 825 | Gly | Ser | Tyr | Arg | Cys 830 | Leu | Cys |
| Pro | Leu | Gly 835 | His | Arg | Leu | Val | Gly 840 | Gly | Arg | Lys | Cys | Lys 845 | Lys | Asp | Ile |
| Asp | Glu 850 | Cys | Ser | Gln | Asp | Pro 855 | Gly | Leu | Cys | Leu | Pro 860 | His | Ala | Cys | Glu |
| Asn | Leu 865 | Gln | Gly | Ser | Tyr | Val 870 | Cys | Val | Cys | Asp 875 | Glu | Gly | Phe | Thr | Leu 880 |
| Thr | Gln | Asp | Gln | His 885 | Gly | Cys | Glu | Glu | Val 890 | Glu | Gln | Pro | His | His 895 | Lys |

```
Lys Glu Cys Tyr Leu Asn Phe Asp Asp Thr Val Phe Cys Asp Ser Val
            900             905             910

Leu Ala Thr Asn Val Thr Gln Gln Glu Cys Cys Cys Ser Leu Gly Ala
        915             920             925

Gly Trp Gly Asp His Cys Glu Ile Tyr Pro Cys Pro Val Tyr Ser Ser
    930             935             940

Ala Glu Phe His Ser Leu Val Pro Asp Gly Lys Arg Leu His Ser Gly
945             950             955             960

Gln Gln His Cys Glu Leu Cys Ile Pro Ala His Arg Asp Ile Asp Glu
            965             970             975

Cys Ile Leu Phe Gly Ala Glu Ile Cys Lys Glu Gly Lys Cys Val Asn
        980             985             990

Ser Gln Pro Gly Tyr Glu Cys Tyr Cys Lys Gln Gly Phe Tyr Tyr Asp
        995             1000            1005

Gly Asn Leu Leu Glu Cys Val Asp Val Asp Glu Cys Leu Asp Glu Ser
    1010            1015            1020

Asn Cys Arg Asn Gly Val Cys Glu Asn Thr Trp Arg Leu Pro Cys Ala
1025            1030            1035            1040

Cys Thr Pro Pro Ala Glu Tyr Ser Pro Ala Gln Ala Gln Cys Leu Ile
            1045            1050            1055

Pro Glu Arg Trp Ser Thr Pro Gln Arg Asp Val Lys Cys Ala Gly Ala
            1060            1065            1070

Ser Glu Glu Arg Thr Ala Cys Val Trp Gly Pro Trp Ala Gly Pro Ala
            1075            1080            1085

Leu Thr Phe Asp Asp Cys Cys Cys Arg Gln Pro Arg Leu Gly Thr Gln
    1090            1095            1100

Cys Arg Pro Cys Pro Arg Gly Thr Gly Ser Gln Cys Pro Thr Ser
1105            1110            1115            1120

Gln Ser Glu Ser Asn Ser Phe Trp Asp Thr Ser Pro Leu Leu Leu Gly
            1125            1130            1135

Lys Ser Pro Arg Asp Glu Asp Ser Ser Glu Glu Asp Ser Asp Glu Cys
        1140            1145            1150

Arg Cys Val Ser Gly Pro Cys Val Pro Arg Pro Gly Gly Ala Val Cys
        1155            1160            1165

Glu Cys Pro Gly Gly Phe Gln Leu Asp Ala Ser Arg Ala Arg Cys Val
    1170            1175            1180

Asp Ile Asp Glu Cys Arg Glu Leu Asn Gln Arg Gly Leu Leu Cys Lys
1185            1190            1195            1200

Ser Glu Arg Cys Val Asn Thr Ser Gly Ser Phe Arg Cys Val Cys Lys
        1205            1210            1215

Ala Gly Phe Thr Arg Ser Arg Pro His Gly Pro Ala Cys Leu Ser Ala
        1220            1225            1230

Ala Ala Asp Asp Ala Ala Ile Ala His Thr Ser Val Ile Asp His Arg
        1235            1240            1245

Gly Tyr Phe His
        1250
```

GENE TRANSFER INTO BONE CELLS AND TISSUES

BACKGROUND OF THE INVENTION

1. Field of the Invention

The present invention relates generally to the field of bone cells and tissues and, more particularly, it concerns the transfer of genetic material into bone. In certain examples, the invention concerns the use of nucleic acids to stimulate bone growth, repair and regeneration. Methods, compositions and devices are provided for transferring an osteotropic gene into bone progenitor cells, which is shown to stimulate progenitor cells and to promote increased bone formation in vivo. This invention may be used to administer nucleic acids to bone tissue in many circumstances, including the treatment of a variety of diseases, from promoting fracture repair and bone reconstruction, to treating osteoporosis and osteogenesis imperfecta.

2. Description of the Related Art

Defects in the process of bone repair and regeneration are linked to the development of several human diseases and disorders, e.g., osteoporosis and osteogenesis imperfecta. Failure of the bone repair mechanism is, of course, also associated with significant complications in clinical orthopaedic practice, for example, fibrous non-union following bone fracture, implant interface failures and large allograft failures. The lives of many individuals would be improved by the development of new therapies designed to stimulate and strengthen the fracture repair process.

Naturally, any new technique to stimulate bone repair would be a valuable tool in treating bone fractures. A significant portion of fractured bones are still treated by casting, allowing natural mechanisms to effect wound repair. Although there have been advances in fracture treatment in recent years, including improved devices, the development of new processes to stimulate, or complement, the wound repair mechanisms would represent significant progress in this area.

A very significant patient population that would benefit from new therapies designed to promote fracture repair, or even prevent or lessen fractures, are those patients suffering from osteoporosis. The term osteoporosis refers to a heterogeneous group of disorders characterized by decreased bone mass and fractures. Clinically, osteoporosis is segregated into type I and type II. Type I osteoporosis occurs predominantly in middle aged women and is associated with estrogen loss at the menopause, while osteoporosis type II is associated with advancing age.

An estimated 20–25 million people are at increased risk for fracture because of site-specific bone loss. The cost of treating osteoporosis in the United States is currently estimated to be in the order of $10 billion per year. Demographic trends, i.e., the gradually increasing age of the US population, suggest that these costs may increase 2–3 fold by the year 2020 if a safe and effective treatment is not found.

The major focus of current therapies for osteoporosis is fracture prevention, not fracture repair. This is an important consideration, as it is known that significant morbidity and mortality are associated with prolonged bed rest in the elderly, especially those who have suffered hip fracture. New methods are clearly needed for stimulating fracture repair, thus restoring mobility in these patients before the complications arise.

Osteogenesis imperfecta (OI) refers to a group of inherited connective tissue diseases characterized by bone and soft connective tissue fragility (Byers & Steiner, 1992; Prockop, 1990). Males and females are affected equally, and the overall incidence is currently estimated to be 1 in 5,000–14,000 live births. Hearing loss, dentinogenesis imperfecta, respiratory insufficiency, severe scoliosis and emphysema are just some of the conditions that are associated with one or more types of OI. While accurate estimates of the health care costs are not available, the morbidity and mortality associated with OI certainly result from the extreme propensity to fracture (OI types I–IV) and the deformation of abnormal bone following fracture repair (OI types II–IV) (Bonadio & Goldstein, 1993). The most relevant issue with OI treatment is to develop new methods by which to improve fracture repair and thus to improve the quality of life of these patients.

The techniques of bone reconstruction, such as is used to reconstruct defects occurring as a result of trauma, cancer surgery or errors in development, would also be improved by new methods to promote bone repair. Reconstructive methods currently employed, such as using autologous bone grafts, or bone grafts with attached soft tissue and blood vessels, are associated with significant drawbacks of both cost and difficulty. For example, harvesting a useful amount of autologous bone is not easily achieved, and even autologous grafts often become infected or suffer from resorption.

The process of bone repair and regeneration resembles the process of wound healing in other tissues. A typical sequence of events includes; hemorrhage; clot formation; dissolution of the clot with concurrent removal of damaged tissues; ingrowth of granulation tissue; formation of cartilage; capillary ingrowth and cartilage turnover; rapid bone formation (callus tissue); and, finally, remodeling of the callus into cortical and trabecular bone. Therefore, bone repair is a complex process that involves many cell types and regulatory molecules. The diverse cell populations involved in fracture repair include stem cells, macrophages, fibroblasts, vascular cells, osteoblasts, chondroblasts, and osteoclasts.

Regulatory factors involved in bone repair are known to include systemic hormones, cytokines, growth factors, and other molecules that regulate growth and differentiation. Various osteoinductive agents have been purified and shown to be polypeptide growth-factor-like molecules. These stimulatory factors are referred to as bone morphogenetic or morphogenic proteins (BMPs), and have also been termed osteogenic bone inductive proteins or osteogenic proteins (OPs). Several BMP (or OP) genes have now been cloned, and the common designations are BMP-1 through BMP-8. Although the BMP terminology is widely used, it may prove to be the case that there is an OP counterpart term for every individual BMP (Alper, 1994).

BMPs 2–8 are generally thought to be osteogenic, although BMP-1 is a more generalized morphogen (Shimell et al., 1991). BMP-3 is also called osteogenin (Luyten et al., 1989) and BMP-7 is also called OP-1 (Ozkaynak et al., 1990). BMPs are related to, or part of, the transforming growth factor-$\beta$ (TGF-$\beta$) superfamily, and both TGF-$\beta$1 and TGF-$\beta$2 also regulates osteoblast function (Seitz et al., 1992). Several BMP (or OP) nucleotide sequences and polypeptides have been described in U.S. patents, e.g., U.S. Pat. Nos. 4,795,804; 4,877,864; 4,968,590; 5,108,753; including, specifically, BMP-1 disclosed in U.S. Pat. No. 5,108,922; BMP-2A in U.S. Pat. Nos. 5,166,058 and 5,013,649; BMP-2B disclosed in U.S. Pat. No. 5,013,649; BMP-3 in U.S. Pat. No. 5,116,738; BMP-5 in U.S. Pat. No. 5,106,748; BMP-6 in U.S. Pat. No. 5,187,076; BMP-7 in U.S. Pat. Nos. 5,108,753 and 5,141,905; and OP-1, COP-5 and COP-7 in U.S. Pat. No. 5,011,691.

Other growth factors or hormones that have been reported to have the capacity to stimulate new bone formation include acidic fibroblast growth factor (Jingushi et al., 1990); estrogen (Boden et al., 1989); macrophage colony stimulating factor (Horowitz et al., 1989); and calcium regulatory agents such as parathyroid hormone (PTH) (Raisz & Kream, 1983).

Several groups have investigated the possibility of using bone stimulating proteins and polypeptides, particularly recombinant BMPs, to influence bone repair in vivo. For example, recombinant BMP-2 has been employed to repair surgically created defects in the mandible of adult dogs (Toriumi et al., 1991), and high doses of this molecule have been shown to functionally repair segmental defects in rat femurs (Yasko et al., 1992). Chen and colleagues showed that a single application of 25–100 ng of recombinant TGF-β1 adjacent to cartilage induced endochondral bone formation in the rabbit ear full thickness skin wounds (Chen et al., 1991). It has also been reported that an application of TGF-β1 in a 3% methylcellulose gel was able to repair surgically induced large skull defects that otherwise heal by fibrous connective tissue and never form bone (Beck et al., 1991).

However, there are many drawbacks associated with these type of treatment protocols, not least the expensive and time-consuming purification of the recombinant proteins from their host cells. Also, polypeptides, once administered to an animal are more unstable than is generally desired for a therapeutic agent, and they are susceptible to proteolytic attack. Furthermore, the administration of recombinant proteins can initiate various inhibitive or otherwise harmful immune responses. It is clear, therefore, that a new method capable of promoting bone repair and regeneration in vivo would represent a significant scientific and medical advance with immediate benefits to a large number of patients. A method readily adaptable for use with a variety of bone-stimulatory genes would be particularly advantageous.

SUMMARY OF THE INVENTION

The present invention seeks to overcome one or more of these and other drawbacks inherent in the prior art by providing novel methods, compositions and devices for use in transferring nucleic acids into bone cells and tissues, and for promoting bone repair and regeneration. The invention rests, in general terms, with the inventors' surprising finding that nucleic acids can be effectively transferred to bone progenitor cells in vivo and that, in certain embodiments, the transfer of an osteotropic gene stimulates bone repair in an animal.

The invention, in general terms, thus concerns methods, compositions and devices for transferring a nucleic acid segment into bone progenitor cells or tissues. The methods of the invention generally comprise contacting bone progenitor cells with a composition comprising a nucleic acid segment in a manner effective to transfer the nucleic acid segment into the cells. The cells may be cultured cells or recombinant cells maintained in vitro, when all that is required is to add the nucleic acid composition to the cells, e.g., by adding it to the culture media.

Alternatively, the progenitor cells may be located within a bone progenitor tissue site of an animal, when the nucleic acid composition would be applied to the site in order to effect, or promote, nucleic acid transfer into bone progenitor cells in vivo. In transferring nucleic acids into bone cells within an animal, a preferred method involves first adding the genetic material to a bone-compatible matrix and then using the impregnated matrix to contact an appropriate tissue site within the animal.

An extremely wide variety of genetic material can be transferred to bone progenitor cells or tissues using the compositions and methods of the invention. For example, the nucleic acid segment may be DNA (double or single-stranded) or RNA (e.g., mRNA, tRNA, rRNA); it may also be a "coding segment", i.e., one that encodes a protein or polypeptide, or it may be an antisense nucleic acid molecule, such as antisense RNA that may function to disrupt gene expression. The nucleic acid segments may thus be genomic sequences, including exons or introns alone or exons and introns, or coding cDNA regions, or in fact any construct that one desires to transfer to a bone progenitor cell or tissue. Suitable nucleic acid segments may also be in virtually any form, such as naked DNA or RNA, including linear nucleic acid molecules and plasmids, or as a functional insert within the genomes of various recombinant viruses, including viruses with DNA genomes and retroviruses.

The invention may be employed to promote expression of a desired gene in bone cells or tissues and to impart a particular desired phenotype to the cells. This expression could be increased expression of a gene that is normally expressed (i.e., "over-expression"), or it could be used to express a gene that is not normally associated with bone progenitor cells in their natural environment. Alternatively, the invention may be used to suppress the expression of a gene that is naturally expressed in such cells and tissues, and again, to change or alter the phenotype. Gene suppression may be a way of expressing a gene that encodes a protein that exerts a down-regulatory function, or it may utilize antisense technology.

Bone Progenitor Cells and Tissues

In certain embodiments, this invention provides advantageous methods for using genes to stimulate bone progenitor cells. As used herein, the term "bone progenitor cells" refers to any or all of those cells that have the capacity to ultimately form, or contribute to the formation of, new bone tissue. This includes various cells in different stages of differentiation, such as, for example, stem cells, macrophages, fibroblasts, vascular cells, osteoblasts, chondroblasts, osteoclasts, and the like. Bone progenitor cells also include cells that have been isolated and manipulated in vitro, e.g., subjected to stimulation with agents such as cytokines or growth factors or even genetically engineered cells. The particular type or types of bone progenitor cells that are stimulated using the methods and compositions of the invention are not important, so long as the cells are stimulated in such a way that they are activated and, in the context of in vivo embodiments, ultimately give rise to new bone tissue.

The term "bone progenitor cell" is also used to particularly refer to those cells that are located within, are in contact with, or migrate towards (i.e., "home to"), bone progenitor tissue and which cells directly or indirectly stimulate the formation of mature bone. As such, the progenitor cells may be cells that ultimately differentiate into mature bone cells themselves, i.e., cells that "directly" form new bone tissue. Cells that, upon stimulation, attract further progenitor cells or promote nearby cells to differentiate into bone-forming cells (e.g., into osteoblasts, osteocytes and/or osteoclasts) are also considered to be progenitor cells in the context of this disclosure—as their stimulation "indirectly" leads to bone repair or regeneration. Cells affecting bone formation indirectly may do so by the elaboration of various growth factors or cytokines, or by their physical interaction with other cell types. Although of scientific interest, the direct or indirect mechanisms by which progenitor cells stimulate bone repair is not a consideration in practicing this invention.

Bone progenitor cells and bone progenitor tissues may be cells and tissues that, in their natural environment, arrive at an area of active bone growth, repair or regeneration. In terms of bone progenitor cells, these may also be cells that are attracted or recruited to such an area. These may be cells that are present within an artificially-created osteotomy site in an animal model, such as those disclosed herein. Bone progenitor cells may also be isolated from animal or human tissues and maintained in an in vitro environment. Suitable areas of the body from which to obtain bone progenitor cells are areas such as the bone tissue and fluid surrounding a fracture or other skeletal defect (whether or not this is an artificallu created site), or indeed, from the bone marrow. Isolated cells may be stimulated using the methods and compositions disclosed herein and, if desired, be returned to an appropriate site in an animal where bone repair is to be stimulated. In such cases, the nucleic-acid containing cells would themselves be a form of therapeutic agent. Such ex vivo protocols are well known to those of skill in the art.

In important embodiments of the invention, the bone progenitor cells and tissues will be those cells and tissues that arrive at the area of bone fracture or damage that one desires to treat. Accordingly, in treatment embodiments, there is no difficulty associated with the identification of suitable target progenitor cells to which the present therapeutic compositions should be applied. All that is required in such cases is to obtain an appropriate stimulatory composition, as disclosed herein, and contact the site of the bone fracture or defect with the composition. The nature of this biological environment is such that the appropriate cells will become activated in the absence of any further targeting or cellular identification by the practitioner.

Certain methods of the invention involve, generally, contacting bone progenitor cells with a composition comprising one or more osteotropic genes (with or without additional genes, proteins or other biomolecules) so as to promote expression of said gene in said cells. As outlined above, the cells may be contacted in vitro or in vivo. This is achieved, in the most direct manner, by simply obtaining a functional osteotropic gene construct and applying the construct to the cells. The present inventors surprisingly found that there are no particular molecular biological modifications that need to be performed in order to promote effective expression of the gene in progenitor cells. Contacting the cells with DNA, e.g., a linear DNA molecule, or DNA in the form of a plasmid or other recombinant vector, that contains the gene of interest under the control of a promoter, along with the appropriate termination signals, is sufficient to result in uptake and expression of the DNA, with no further steps necessary.

In preferred embodiments, the process of contacting the progenitor cells with the osteotropic gene composition is conducted in vivo. Again, a direct consequence of this process is that the cells take up and express the gene and that they, without additional steps, function to stimulate bone tissue growth, repair or regeneration.

An assay of an osteo-inductive gene may be conducted using the bone induction bioassay of Sampath & Reddi (1981; incorporated herein by reference). This is a rat bone formation assay that is routinely used to evaluate the osteogenic activity of bone inductive factors. However, for analyzing the effects of osteotropic genes on bone growth, one is generally directed to use the novel osteotomy model disclosed herein.

Osteotropic Genes

As used herein, the terms "osteotropic and osteogenic gene" are used to refer to a gene or DNA coding region that encodes a protein, polypeptide or peptide that is capable of promoting, or assisting in the promotion of, bone formation, or one that increases the rate of primary bone growth or healing (or even a gene that increases the rate of skeletal connective tissue growth or healing). The terms promoting, inducing and stimulating are used interchangeably throughout this text to refer to direct or indirect processes that ultimately result in the formation of new bone tissue or in an increased rate of bone repair. Thus, an osteotropic gene is a gene that, when expressed, causes the phenotype of a cell to change so that the cell either differentiates, stimulates other cells to differentiate, attracts bone-forming cells, or otherwise functions in a manner that ultimately gives rise to new bone tissue.

In using the new osteotomy model of the invention, an osteotropic gene is characterized as a gene that is capable of stimulating proper bone growth in the osteotomy gap to any degree higher than that observed in control studies, e.g., parallel studies employing an irrelevant marker gene such as $\beta$-galactosidase. This stimulation of "proper bone growth" includes both the type of tissue growth and the rate of bone formation. In using the model with a 5 mm osteotomy gap, an osteotropic gene is generally characterized as a gene that is capable of promoting or inducing new bone formation, rather than abnormal bone fracture repair, i.e. fibrous nonunion. In using the 2 mm osteotomy gap, one may characterize osteotropic genes as genes that increase the rate of primary bone healing as compared to controls, and more preferably, genes capable of stimulating repair of the osteotomy defect in a time period of less than nine weeks.

In general terms, an osteotropic gene may also be characterized as a gene capable of stimulating the growth or regeneration of skeletal connective tissues such as, e.g., tendon, cartilage, and ligament. Thus, in certain embodiments, the methods and compositions of the invention may be employed to stimulate the growth or repair of both bone tissue itself and also of skeletal connective tissues.

A variety of osteotropic genes are now known, all of which are suitable for use in connection with the present invention. Osteotropic genes and the proteins that they encode include, for example, systemic hormones, such as parathyroid hormone (PTH) and estrogen; many different growth factors and cytokines; chemotactic or adhesive peptides or polypeptides; molecules such as activin (U.S. Pat. No. 5,208,219, incorporated herein by reference); specific bone morphogenetic proteins (BMPs); and even growth factor receptor genes.

Examples of suitable osteotropic growth factors include those of the transforming growth factor (TGF) gene family, including TGFs 1–4, and particularly TGF-$\alpha$, TGF-$\beta$1, TGF-$\beta$2 (U.S. Pat. Nos. 5,168,051; 4,886,747 and 4,742,003, each incorporated herein by reference); and also fibroblast growth factors (FGF), such as acidic FGF and kFGF; granulocyte/macrophage colony stimulating factor (GMCSF); epidermal growth factor (EGF); platelet derived growth factor (PDGF); insulin-like growth factors (IGF), including IGF-I and IGF-II; and leukemia inhibitory factor (LIF), also known as HILDA and DIA. Any of the above or other related genes, or DNA segments encoding the active portions of such proteins, may be used in the novel methods and compositions of the invention.

Certain preferred osteotropic genes and DNA segments are those of the TGF superfamily, such as TGF-$\alpha$, TGF-$\beta$1 and TGF-$\beta$2, and members of the BMP family of genes. For example, several BMP genes have been cloned that are ideal candidates for use in the nucleic acid transfer or delivery protocols of the invention. Suitable BMP genes are those designated BMP-2 through BMP-8. BMP-1 is not considered to be particularly useful at this stage.

There is considerable variation in the terminology currently employed in the literature in referring to these genes and polypeptides. It will be understood by those of skill in the art that all BMP genes that encode an active osteogenic protein are considered for use in this invention, regardless of the differing terminology that may be employed. For example, BMP-3 is also called osteogenin and BMP-7 is also called OP-1 (osteogenic protein-1). It is likely that the family of factors termed OP(s) is as large as that termed BMP(s), and that these terms, in fact, describe the same set of molecules (Alper, 1994).

The DNA sequences for several BMP (or OP) genes have been described both in scientific articles and in U.S. patents such as U.S. Pat. Nos. 4,877,864; 4,968,590; 5,108,753. Specifically, BMP-1 sequences are disclosed in U.S. Pat. No. 5,108,922; BMP-2A in U.S. Pat. Nos. 5,166,058 and 5,013,649; BMP-2B disclosed in U.S. Pat. No. 5,013,649; BMP-3 in U.S. Pat. No. 5,116,738; BMP-5 in U.S. Pat. No. 5,106,748; BMP-6 in U.S. Pat. No. 5,187,076; and BMP-7 in U.S. Pat. Nos. 5,108,753 and 5,141,905; all incorporated herein by reference). The article by Wozney et al. (1988; incorporated herein by reference) is considered to be particularly useful for describing BMP molecular clones and their activities. DNA sequences encoding the osteogenic proteins designated OP-1, COP-5 and COP-7 are also disclosed in U.S. Pat. No. 5,011,691.

All of the above issued U.S. patents are incorporated herein by reference and are intended to be used in order to supplement the present teachings regarding the preparation of BMP and OP genes and DNA segments that express osteotropic polypeptides. As disclosed in the above patents, and known to those of skill in the art, the original source of a recombinant gene or DNA segment to be used in a therapeutic regimen need not be of the same species as the animal to be treated. In this regard, it is contemplated that any recombinant PTH, TGF or BMP gene may be employed to promote bone repair or regeneration in a human subject or an animal, such as, e.g., a horse. Particularly preferred genes are those from human, mouse and bovine sources, in that such genes and DNA segments are readily available, with the human or mouse forms of the gene being most preferred for use in human treatment regimens. Recombinant proteins and polypeptides encoded by isolated DNA segments and genes are often referred to with the prefix "r" for recombinant and "rh" for recombinant human. As such, DNA segments encoding rBMPs, such as rhBMP-2A or rhBMP-4, are contemplated to be particularly useful in connection with this invention.

To prepare an osteotropic gene segment or cDNA one may follow the teachings disclosed herein and also the teachings of any of patents or scientific documents specifically referenced herein. Various nucleotide sequences encoding active BMPs are disclosed in U.S. Pat. Nos. 5,166,058, 5,013,649, 5,116,738, 5,106,748, 5,187,076, 5,108,753 and 5,011,691, each incorporated herein by reference. By way of example only, U.S. Pat. No. 5,166,058, teaches that hBMP-2A is encoded by a nucleotide sequence from nucleotide #356 to nucleotide #1543 of the sequence shown in Table II of the patent. One may thus obtain a hBMP-2A DNA segment using molecular biological techniques, such as polymerase chain reaction (PCR) or screening a cDNA or genomic library, using primers or probes with sequences based on the above nucleotide sequence. The practice of such techniques is a routine matter for those of skill in the art, as taught in various scientific articles, such as Sambrook et al. (1989), incorporated herein by reference. Certain documents further particularly describe suitable mammalian expression vectors, e.g., U.S. Pat. No. 5,168,050, incorporated herein by reference.

Osteotropic genes and DNA segments that are particularly preferred for use in the present compositions and methods are the TGFα and TGFβ genes (U.S. Pat. Nos. 5,168,051; 4,886,747 and 4,742,003, each incorporated herein by reference), with TGFα being particularly considered for applications involving skeletal soft tissues; the PTH gene or a DNA segment encoding the active fragment thereof, such as a DNA segment encoding a polypeptide that includes the amino acids 1-34 (hPTH1-34; Hendy et al., 1981; incorporated herein by reference); and the BMP genes termed BMP-4 and BMP-2, such as the gene or cDNA encoding the mouse BMP-4 disclosed herein.

It is also contemplated that one may clone further genes or cDNAs that encode an osteotropic protein or polypeptide. The techniques for cloning DNA molecules, i.e., obtaining a specific coding sequence from a DNA library that is distinct from other portions of DNA, are well known in the art. This can be achieved by, for example, screening an appropriate DNA library, as disclosed in Example XIII herein, which relates to the cloning of a wound healing gene. The screening procedure may be based on the hybridization of oligonucleotide probes, designed from a consideration of portions of the amino acid sequence of known DNA sequences encoding related osteogenic proteins. The operation of such screening protocols are well known to those of skill in the art and are described in detail in the scientific literature, for example, in Sambrook et al. (1989), incorporated herein by reference.

Osteotropic genes with sequences that vary from those described in the literature are also encompassed by the invention, so long as the altered or modified gene still encodes a protein that functions to stimulate bone progenitor cells in any direct or indirect manner. These sequences include those caused by point mutations, those due to the degeneracies of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the osteogenic activity of a protein, to increase its biological stability or half-life, to change its glycosylation pattern, and the like. All such modifications to the nucleotide sequences are encompassed by this invention.

It will, of course, be understood that one or more than one osteotropic gene may be used in the methods and compositions of the invention. The nucleic acid delivery methods may thus entail the administration of one, two, three, or more, osteotropic genes. The maximum number of genes that may be applied is limited only by practical considerations, such as the effort involved in simultaneously preparing a large number of gene constructs or even the possibility of eliciting an adverse cytotoxic effect. The particular combination of genes may be two or more distinct BMP genes; or it may be such that a growth factor gene is combined with a hormone gene, e.g., a BMP gene and a PTH gene; a hormone or growth factor gene may even be combined with a gene encoding a cell surface receptor capable of interacting with the polypeptide product of the first gene.

In using multiple genes, they may be combined on a single genetic construct under control of one or more promoters, or they may be prepared as separate constructs of the same of different types. Thus, an almost endless combination of different genes and genetic constructs may be employed. Certain gene combinations may be designed to, or their use may otherwise result in, achieving synergistic effects on cell stimulation and bone growth, any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic segment or gene could be administered in combination with further agents, such as, e.g., proteins or polypeptides or various pharmaceutically active agents. So long as genetic material forms part of the composition, there is virtually no limit to other components which may also be included, given that the additional agents do not cause a significant adverse effect upon contact with the target cells or tissues. The nucleic acids may thus be delivered along with various other agents, for example, in certain embodiments one may wish to administer an angiogenic factor, and/or an inhibitor of bone resorption, as disclosed in U.S. Pat. Nos. 5,270,300 and 5,118,667, respectively, each incorporated herein by reference.

Gene Constructs and DNA Segments

As used herein, the terms "gene" and "DNA segment" are both used to refer to a DNA molecule that has been isolated free of total genomic DNA of a particular species. Therefore, a gene or DNA segment encoding an osteotropic gene refers to a DNA segment that contains sequences encoding an osteotropic protein, but is isolated away from, or purified free from, total genomic DNA of the species from which the DNA is obtained. Included within the term "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case, an osteotropic gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

This invention provides novel ways in which to utilize various known osteotropic DNA segments and recombinant vectors. As described above, many such vectors are readily available, one particular detailed example of a suitable vector for expression in mammalian cells is that described in U.S. Pat. No. 5,168,050, incorporated herein by reference.

However, there is no requirement that a highly purified vector be used, so long as the coding segment employed encodes a osteotropic protein and does not include any coding or regulatory sequences that would have an adverse effect on bone progenitor cells. Therefore, it will also be understood that useful nucleic acid sequences may include additional residues, such as additional non-coding sequences flanking either of the 5' or 3' portions of the coding region or may include various internal sequences, i.e., introns, which are known to occur within genes.

After identifying an appropriate osteotropic gene or DNA molecule, it may be inserted into any one of the many vectors currently known in the art, so that it will direct the expression and production of the osteotropic protein when incorporated into a bone progenitor cell. In a recombinant expression vector, the coding portion of the DNA segment is positioned under the control of a promoter. The promoter may be in the form of the promoter which is naturally associated with an osteotropic gene, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an osteotropic gene in its natural environment. Such promoters may include those normally associated with other osteotropic genes, and/or promoters isolated from any other bacterial, viral, eukaryotic, or mammalian cell. Naturally, it will be important to employ a promoter that effectively directs the expression of the DNA segment in bone progenitor cells.

The use of recombinant promoters to achieve protein expression is generally known to those of skill in the art of molecular biology, for example, see Sambrook et al. (1989). The promoters employed may be constitutive, or inducible, and can be used under the appropriate conditions to direct high level or regulated expression of the introduced DNA segment. The currently preferred promoters are those such as CMV, RSV LTR, the SV40 promoter alone, and the SV40 promoter in combination with the SV40 enhancer.

Osteotropic genes and DNA segments may also be in the form of a DNA insert which is located within the genome of a recombinant virus, such as, for example a recombinant adenovirus, adeno-associated virus (AAV) or retrovirus. In such embodiments, to place the gene in contact with a bone progenitor cell, one would prepare the recombinant viral particles, the genome of which includes the osteotropic gene insert, and simply contact the progenitor cells or tissues with the virus, whereby the virus infects the cells and transfers the genetic material.

In preferred embodiments, one would impregnate a matrix or implant material with virus by soaking the material in recombinant virus stock solution, e.g., for 1–2 hours, and then contact the bone progenitor cells or tissues with the impregnated matrix. Cells then penetrate, or grow into, the matrix, thereby contacting the virus and allowing viral infection which leads to the cells taking up the desired gene or cDNA and expressing the encoded protein.

Bone-Compatible Matrices

In a preferred embodiment, the methods of the invention involve preparing a composition in which the osteotropic gene, genes, DNA segments, or cells already incorporating such genes or segments, are associated with, or impregnated within, a bone-compatible matrix, to form a "matrix-gene composition" and the matrix-gene composition is then placed in contact with the bone progenitor cells or tissue. The matrix may become impregnated with a gene DNA segment simply by soaking the matrix in a solution containing the DNA, such as a plasmid solution, for a brief period of time of anywhere from about 5 minutes or so, up to and including about an hour. Matrix-gene compositions are all those in which a gene is adsorbed, absorbed, or otherwise maintained in contact with the matrix.

The type of matrix that may be used in the compositions, devices and methods of the invention is virtually limitless, so long as it is a "bone-compatible matrix". This means that the matrix has all the features commonly associated with being "biocompatible", in that it is in a form that does not produce an adverse, allergic or other untoward reaction when administered to an animal, and it is also suitable for placing in contact with bone tissue. This latter requirement takes into consideration factors such as the capacity of the matrix to provide a structure for the developing bone and, preferably, its capacity to resorbed into the body after the bone has been repaired.

The choice of matrix material will differ according to the particular circumstances and the site of the bone that is to be treated. Matrices such as those described in U.S. Pat. No. 5,270,300 (incorporated herein by reference) may be employed. Physical and chemical characteristics, such as, e.g., biocompatibility, biodegradability, strength, rigidity, interface properties and even cosmetic appearance may be considered in choosing a matrix, as is well known to those of skill in the art. Appropriate matrices will both deliver the gene composition and also provide a surface for new bone growth, i.e., will act as an in situ scaffolding through which progenitor cells may migrate.

A particularly important aspect of the present invention is its use in connection with orthopaedic implants and interfaces and artificial joints, including implants themselves and functional parts of an implant, such as, e.g., surgical screws, pins, and the like. In preferred embodiments, it is contemplated that the metal surface or surfaces of an implant or a portion thereof, such as a titanium surface, will be coated with a material that has an affinity for nucleic acids, most preferably, with hydroxyl apatite, and then the coated-metal will be further coated with the gene or nucleic acid that one wishes to transfer. The available chemical groups of the absorptive material, such as hydroxyl apatite, may be readily manipulated to control its affinity for nucleic acids, as is known to those of skill in the art.

In certain embodiments, non-biodegradable matrices may be employed, such as sintered hydroxyapatite, bioglass, aluminates, other bioceramic materials and metal materials, particularly titanium. A suitable ceramic delivery system is that described in U.S. Pat. No. 4,596,574, incorporated herein by reference. Polymeric matrices may also be employed, including acrylic ester polymers and lactic acid polymers, as disclosed in U.S. Pat. Nos. 4,526,909, and 4,563,489, respectively, each incorporated herein by reference.

In preferred embodiments, it is contemplated that a biodegradable matrix will likely be most useful. A biodegradable matrix is generally defined as one that is capable of being resorbed into the body. Potential biodegradable matrices for use in connection with the compositions, devices and methods of this invention include, for example, biodegradable and chemically defined calcium sulfate, tricalciumphosphate, hydroxyapatite, polylactic acid, polyanhydrides, matrices of purified proteins, and semi-purified extracellular matrix compositions. The most preferred matrices are those prepared from tendon or dermal collagen, as may be obtained from a variety of commercial sources, such as, e.g., Sigma and Collagen Corporation. Collagen matrices may also be prepared as described in U.S. Pat. Nos. 4,394,370 and 4,975,527, each incorporated herein by reference. Currently, the most preferred collagenous material is that termed UltraFiber™, obtainable from Norian Corp. (Mountain View, Calif.).

Nucleic Acid Transfer Embodiments

Once a suitable matrix-gene composition has been prepared or obtained, all that is required to deliver the osteotropic gene to bone progenitor cells within an animal is to place the matrix-gene composition in contact with the site in the body in which one wishes to promote bone growth. This could be a simple bone fracture site that one wishes to repair, an area of weak bone, such as in a patient with osteoporosis, or a bone cavity site that one wishes to fill with new bone tissue. Bone cavities may arise as a result of an inherited disorder, birth defect, or may result following dental or periodontal surgery or after the removal of an osteosarcoma.

The amount of gene construct that is applied to the matrix and the amount of matrix-gene material that is applied to the bone tissue will be determined by the attending physician or veterinarian considering various biological and medical factors. For example, one would wish to consider the particular osteotropic gene and matrix, the amount of bone weight desired to be formed, the site of bone damage, the condition of the damaged bone, the patient's or animal's age, sex, and diet, the severity of any infection, the time of administration and any further clinical factors that may affect bone growth, such as serum levels of various factors and hormones. The suitable dosage regimen will therefore be readily determinable by one of skill in the art in light of the present disclosure, bearing in mind the individual circumstances.

In treating humans and animals, progress may be monitored by periodic assessment of bone growth and/or repair, e.g. using x-rays. The therapeutic methods and compositions of the invention are contemplated for use in both medical and veterinary applications, due to the lack of species specificity in bone inductive factors. In particular, it is contemplated that domestic, farm and zoological animals, as well as thoroughbred horses, would be treatable using the nucleic acid transfer protocols disclosed herein.

The present methods and compositions may also have prophylactic uses in closed and open fracture reduction and also in the improved fixation of artificial joints. The invention is applicable to stimulating bone repair in congenital, trauma-induced, or oncologic resection-induced craniofacial defects, and also is useful in the treatment of periodontal disease and other tooth repair processes and even in cosmetic plastic surgery. The matrix-gene compositions and devices of this invention may also be used in wound healing and related tissue repair, including, but not limited to healing of burns, incisions and ulcers.

The present invention also encompasses DNA-based compositions for use in cellular transfer to treat bone defects and disorders. The compositions of the invention generally comprise an osteotropic gene in association with a bone-compatible matrix, wherein the composition is capable of stimulating bone growth, repair or regeneration upon administration to, or implantation within, a bone progenitor tissue site of an animal. The osteotropic gene or genes may be any of those described above, with TGF-α (for soft skeletal tissues), TGF-β1, TGF-β2, PTH, BMP-2 and BMP-4 genes being generally preferred. Likewise, irrespective of the choice of gene, the bone-compatible matrix may be any of those described above, with biodegradable matrices such as collagen being particularly preferred.

In still further embodiments, the present invention concerns osteotropic devices, which devices may be generally considered as molded or designed matrix-gene compositions. The devices of the invention naturally comprise a bone-compatible matrix in which an osteotropic gene is associated with the matrix. The combination of genes and matrix components is such that the device is capable of stimulating bone growth or healing when implanted in an animal. The devices may be of virtually any size or shape, so that their dimensions are adapted to fit a bone fracture or bone cavity site in the animal that is to be treated, allowing the fracture join and/or bone regrowth to be more uniform. Other particularly contemplated devices are those that are designed to act as an artifical joint. Titanium devices and hydroxylapatite-coated titanium devices will be preferred in certain embodiments. Parts of devices in combination with an osteotropic nucleic acid segment, such as a DNA-coated screw for an artificial joint, and the like, also fall within the scope of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A, FIG. 4B, FIG. 4C and FIG. 4D. Northern blot analysis of a transduced Rat-1 clone. Poly-A($^+$)RNA was prepared from the YZ-15 clone and analyzed by Northern blotting as described (Chen et al., 1993). Poly-A($^+$) RNA prepared from PLJ-hPTH1-84 cells, BAG cells, and native Rat-1 cells were used as positive and negative controls. Four probes were applied to a single blot following sequential stripping: hPTH1-34 (FIG. 4A), β-gal (FIG. 4B), Neo (FIG. 4C), and β-actin (FIG. 4D). Lane assignments were as follows: 1, PLJhPTH1-84 cells; 2, BAG cells; 3, YZ-15 cells; 4, native Rat-1 cells. As expected, the hPTH1-34 transcript is seen only in lane 1 (positive control) and in lane 3; a Neo transcript is seen in lanes 1–3; a β-gal transcript is seen only in lane 2; and β-actin transcripts are seen in lanes 1–4.

FIG. 8A shows an exemplary result, 4 weeks post surgery (Rat #14) using the normal sense hPTH 1-34 construct applied to a 5 mm gap (as described herein, such as in Example X). The arrows point to new bone formed around new bone at pin sites and in gap, as defined by plain film x-ray examination.

FIG. 8B shows an exemplary control (Rat #15) to compare with FIG. 8A in which an antisense construct was applied to a 5 mm gap. There is no evidence of new bone formation 4 weeks post surgery.

FIG. 9. The mouse BMP-4 amino acid sequence, SEQ ID NO:1. The HA epitope is shown in bold at the extreme carboxy terminus of the sequence.

FIG. 10A: note the positive (the dark gray region enclosed within brackets)

β-gal cytoplasmic staining of callus tissue cells from the UltraFiber™+ adenovirus implant. This result indicates that cell surface receptors that mediate infection, and thus viral transduction, are expressed by (at least one population) callus cells during the fracture healing process. FIG. 10B: serial section negative control stained with the vehicle of the β-gal antibody plus a cocktail of non-specific rabbit IgG antibodies. FIG. 10C: note the positive (boxed) β-gal nuclear staining of chondrocytes in the osteotomy site filled with UltraFiber™ and AdRSVntlacZ. This result demonstrates the exquisite specificity of the anti-β-gal antibody, and conclusively demonstrates expression of the marker gene product in the osteotomy gap.

FIG. 11A shows tendon tissue with the SIS+plasmid graft. Note the positive cytoplasmic staining of fibroblastic cells as shown by the continuous light gray staining, indicated by the arrows. The bottom panel shows tendon tissue with the SIS-alone graft. Note the virtual absence of specific cytoplasmic staining in this negative control tissue section.

FIG. 13A, FIG. 13B, FIG. 13C, FIG. 13D, FIG. 13E and FIG. 13F. Expression of new fibrillin gene during mouse development. The transcript is expressed in connective tissue, mesenchyme, liver, heart and CNS. FIG. 13A, FIG. 13B and FIG. 13C were probed with an anti-sense probe; FIG. 13D, FIG. 13E, and FIG. 13F were probed with a sense probe. FIG. 13A and FIG. 13D show expression at 8.5–9.0 days; FIG. 13B and FIG. 13E show expression at 13.5 days; and FIG. 13C and FIG. 13F show expression at 16.5 days development.

DETAILED DESCRIPTION OF THE PREFERRED EMBODIMENTS

Figure 1:
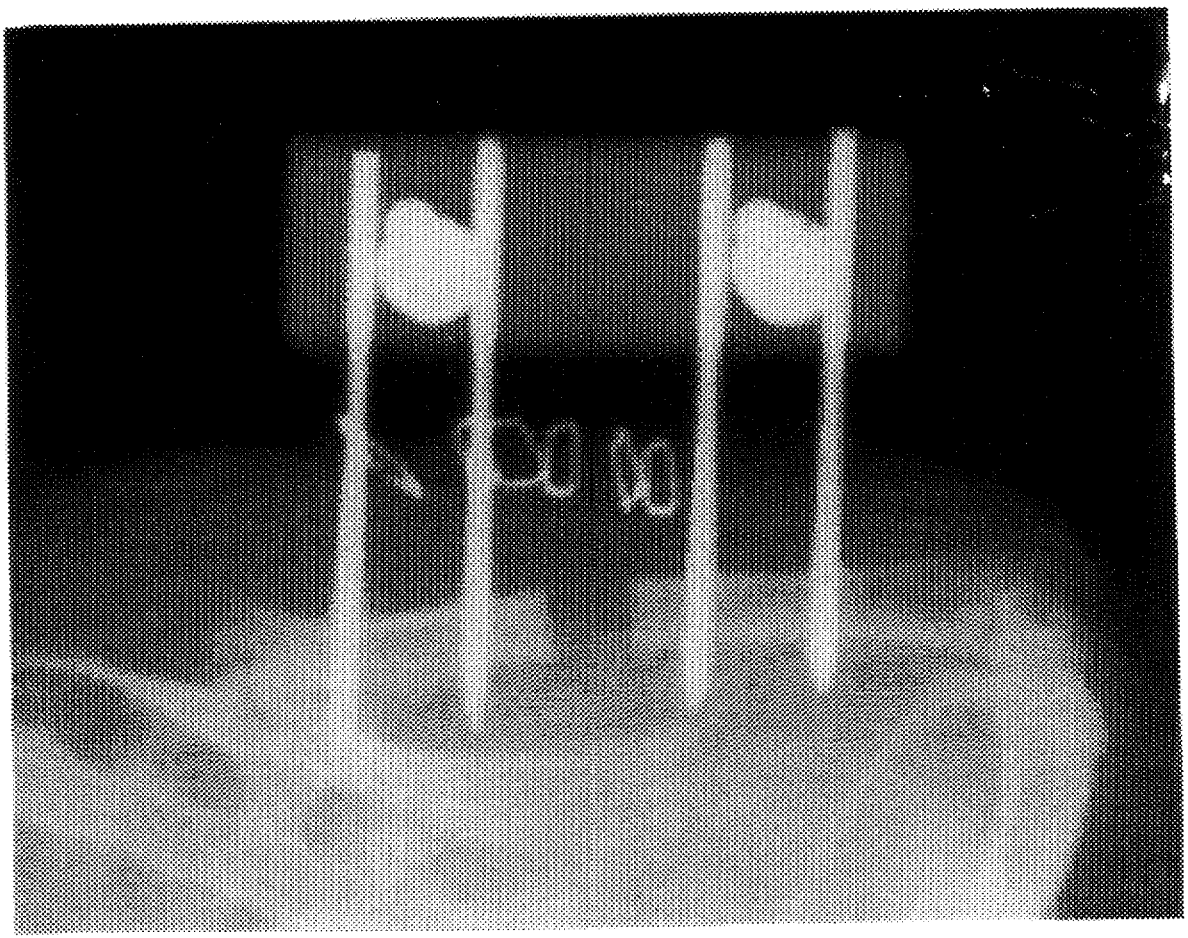
FIG. 1. Rat osteotomy model. The osteotomy site immediately after surgery. As expected, no evidence of mineralized tissue in the osteotomy gap was observed immediately post-op.

1. Applications of Bone Repair Technology to Human Treatment

The following is a brief discussion of four human conditions to exemplify the variety of diseases and disorders that would benefit from the development of new technology to improve bone repair and healing processes. In addition to the following, several other conditions, such as, for example, vitamin D deficiency; wound healing in general; soft skeletal tissue repair; and cartilage and tendon repair and regeneration, may also benefit from technology concerning the stimulation of bone progenitor cells.

The first example is the otherwise healthy individual who suffers a fracture. Often, clinical bone fracture is treated by casting to alleviate pain and allow natural repair mechanisms to repair the wound. There has been progress in the treatment of fracture in recent times, however, even without considering the various complications that may arise in treating fractured bones, any new procedures to increase bone healing in normal circumstances would be represent a great advance.

A second example which may benefit from new treatment methods is osteogenesis imperfecta (OI). OI encompasses various inherited connective tissue diseases that involve bone and soft connective tissue fragility in humans (Byers & Steiner, 1992; Prockop, 1990). About one child per 5,000–14,000 born is affected with OI and the disease is associated with significant morbidity throughout life. A certain number of deaths also occur, resulting from the high propensity for bone fracture and the deformation of abnormal bone after fracture repair (OI types II–IV; Bonadio & Goldstein, 1993). The relevant issue here is quality of life; clearly, the lives of affected individuals would be improved by the development of new therapies designed to stimulate and strengthen the fracture repair process.

OI type I is a mild disorder characterized by bone fracture without deformity, blue sclerae, normal or near normal stature, and autosomal dominant inheritance (Bonadio & Goldstein). Osteopenia is associated with an increased rate of long bone fracture upon ambulation (the fracture frequency decreases dramatically at puberty and during young adult life, but increases once again in late middle age). Hearing loss, which often begins in the second or third decade, is a feature of this disease in about half the families and can progress despite the general decline in fracture frequency. Dentinogenesis imperfecta is observed in a subset of individuals.

In contrast, OI types II–VI represent a spectrum of more severe disorders associated with a shortened life-span. OI type II, the perinatal lethal form, is characterized by short stature, a soft calvarium, blue sclerae, fragile skin, a small chest, floppy appearing lower extremities (due to external rotation and abduction of the femurs), fragile tendons and ligaments, bone fracture with severe deformity, and death in the perinatal period due to respiratory insufficiency. Radiographic signs of bone weakness include compression of the femurs, bowing of the tibiae, broad and beaded ribs, and calvarial thinning.

OI type III is characterized by short stature, a triangular facies, severe scoliosis, and bone fracture with moderate deformity. Scoliosis can lead to emphysema and a shortened life-span due to respiratory insufficiency. OI type IV is characterized by normal sclerae, bone fracture with mild to moderate deformity, tooth defects, and a natural history that essentially is intermediate between OI type II and OI type I.

More than 150 OI mutations have been characterized since 1989 (reviewed in Byers & Steiner, 1992; Prockop, 1990). The vast majority occur in the COL1A1 and COL1A2 genes of type I collagen. Most cases of OI type I appear to result from heterozygous mutations in the COL1A1 gene that decrease collagen production but do not alter primary structure, i.e. heterozygous null mutations affecting COL1A1 expression.

A third, important example is osteoporosis. The term osteoporosis refers to a heterogeneous group of disorders characterized by decreased bone mass and fractures. An estimated 20–25 million people are at increased risk for fracture because of site-specific bone loss. Risk factors for osteoporosis include increasing age, gender (more females), low bone mass, early menopause, race (Caucasians), low calcium intake, reduced physical activity, genetic factors, environmental factors (including cigarette smoking and abuse of alcohol or caffeine), and deficiencies in neuromuscular control that create a propensity to fall.

More than a million fractures in the USA each year can be attributed to osteoporosis, and in 1986 alone the treatment of osteoporosis cost an estimated 7–10 billion health care dollars. Demographic trends (i.e., the gradually increasing age of the US population) suggest that these costs may increase 2–3 fold by the year 2020 if a safe and effective treatment is not found. Clearly, osteoporosis is a significant health care problem.

Clinically, osteoporosis is segregated into type I and type II. Type I osteoporosis occurs predominantly in middle aged women and is associated with estrogen loss at the menopause, while osteoporosis type II is associated with advancing age. Much of the morbidity and mortality associated with osteoporosis results from immobilization of elderly patients following fracture.

Current therapies for osteoporosis patients focus on fracture prevention, not fracture repair. This remains an important Consideration because of the literature, which clearly states that significant morbidity and mortality are associated with prolonged bed rest in the elderly, particularly those who have suffered hip fractures. Complications of bed rest include blood clots and pneumonia. These complications are recognized and measures are usually taken to avoid them, but these is hardly the best approach to therapy. Thus, the osteoporotic patient population would benefit from new therapies designed to strengthen bone and speed up the fracture repair process, thus getting these people on their feet before the complications arise.

A fourth example is related to bone reconstruction and, specifically, the ability to reconstruct defects in bone tissue that result from traumatic injury; as a consequence of cancer or cancer surgery; as a result of a birth defect, an error in development, or a heritable disorder; or as a result of aging. There is a significant orthopaedic need for more frequent implants, and cranial and facial bone are particular targets for this type of reconstructive need. The availability of new implant materials, e.g., titanium, has permitted the repair of relatively large defects. Titanium implants provide excellent temporary stability across bony defects. However, experience has shown that a lack of viable bone bridging the defect can result in exposure of the appliance, infection, structural instability and, ultimately, failure to repair the defect.

Autologous bone grafts are another possibility, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed.

Microsurgical transfers of free bone grafts with attached soft tissue and blood vessels can close bony defects with an immediate source of blood supply to the graft. However, these techniques are time consuming, have been shown to produce a great deal of morbidity, and can only be used by specially trained individuals. Furthermore, the bone implant is often limited in quantity and is not readily contoured. In the mandible, for example, the majority of patients cannot wear dental appliances using presently accepted techniques (even after continuity is established), and thus gain little improvement in the ability to masticate. Toriumi et al. have written that "Reconstructive surgeons should have at their disposal a bone substitute that would be reliable, biocompatible, easy to use, and long lasting and that would restore mandibular continuity with little associated morbidity."

In connection with bone reconstruction, specific problem areas for improvement are those concerned with treating large defects, such as created by trauma, birth defects, or particularly, following tumor resection; and also the area of artificial joints. The success of orthopaedic implants, interfaces and artificial joints could conceivably be improved if the surface of the implant, or a functional part of an implant, were to be coated with a bone stimulatory agent. The surface of implants could be coated with one or more appropriate materials in order to promote a more effective interaction with the biological site surrounding the implant and, ideally, to promote tissue repair.

2. Bone Repair

Bone tissue is known to have the capacity for repair and regeneration and there is a certain understanding of the cellular and molecular basis of these processes. The initiation of new bone formation involves the commitment, clonal expansion, and differentiation of progenitor cells. Once initiated, bone formation is promoted by a variety of polypeptide growth factors. Newly formed bone is then maintained by a series of local and systemic growth and differentiation factors.

The concept of specific bone growth-promoting agents is derived from the work of Huggins and Urist. Huggins et al. demonstrated that autologous transplantation of canine incisor tooth to skeletal muscle resulted in local new bone formation (Huggins et al., 1936). Urist and colleagues reported that demineralized lyophilized bone segments induced bone formation (Urist, 1965; Urist et al., 1983), a process that involved macrophage chemotaxis; the recruitment of progenitor cells; the formation of granulation tissue, cartilage, and bone; bone remodeling; and marrow differentiation. The initiation of cartilage and bone formation in an extraskeletal site, a process referred to as osteoinduction, has permitted the unequivocal identification of initiators of bone morphogenesis (Urist, 1965; Urist et al., 1983; Sampath et al., 1984; Wang et al., 1990; Cunningham et al., 1992).

Significant progress has now been made in characterizing the biological agents elaborated by active bone tissue during growth and natural bone healing. Demineralized bone matrix is highly insoluble; Sampath and Reddi (1981) showed that only 3% of the proteins can be extracted using strong combinations of denaturants and detergents. They also showed that the unfractionated demineralized bone extract will initiate bone morphogenesis, a critical observation that led to the purification of "osteoinductive" molecules. Families of proteinaceous osteoinductive factors have now been purified and characterized. They have been variously referred to in the literature as bone morphogenetic or morphogenic proteins (BMPs), osteogenic bone inductive proteins or osteogenic proteins (OPs).

3. Bone Repair and Bone Morphogenetic Proteins (BMPs)

Following their initial purification, several bone morphogenetic protein genes have now been cloned using molecular techniques (Wozney et al., 1988; Rosen et al., 1989; summarized in Alper, 1994). This work has established BMPs as members of the transforming growth factor-$\beta$ (TGF-$\beta$) superfamily based on DNA sequence homologies. Other TGF molecules have also been shown to participate in new bone formation, and TGF-$\beta$ is regarded as a complex multifunctional regulator of osteoblast function (Centrella et al., 1988; Carrington et al., 1969–1975; Seitz et al., 1992). Indeed, the family of transforming growth factors (TGF-$\alpha$ and TGF-$\beta$) has been proposed as potentially useful in the treatment of bone disease (U.S. Pat. No. 5,125,978, incorporated herein by reference).

The cloning of distinct BMP genes has led to the designation of individual BMP genes and proteins as BMP-1 through BMP-8. BMPs 2–8 are generally thought to be osteogenic (BMP-1 may be a more generalized morphogen; Shimell et al., 1991). BMP-3 is also called osteogenin (Luyten et al., 1989) and BMP-7 is also called OP-1 (Ozkaynak et al., 1990). TGFs and BMPs each act on cells via complex, tissue-specific interactions with families of cell surface receptors (Roberts & Sporn, 1989; Paralkar et al., 1991).

Several BMP (or OP) nucleotide sequences and vectors, cultured host cells and polypeptides have been described in the patent literature. For example, U.S. patents, e.g., U.S. Pat. Nos. 4,877,864, 4,968,590 and 5,108,753 all concern osteogenic factors. More specifically, BMP-1 is disclosed in U.S. Pat. No. 5,108,922; BMP-2 species, including MBP-2A and BMP-2B, are disclosed in U.S. Pat. Nos. 5,166,058, 5,013,649, and 5,013,649; BMP-3 in U.S. Pat. No. 5,116,738; BMP-5 in U.S. Pat. No. 5,106,748; BMP-6 in U.S. Pat. No. 5,187,076; and BMP-7 in U.S. Pat. Nos. 5,108,753 and 5,141,905; all incorporated herein by reference. Various BMP clones and their activities are particularly described by Wozney et al. (1988; incorporated herein by reference). DNA sequences encoding the osteogenic proteins designated OP-1, COP-5 and COP-7 are also disclosed in U.S. Pat. No. 5,011,691. Although the BMP terminology is widely used, it may prove to be the case that there is an OP counterpart term for every individual BMP (Alper, 1994).

4. Bone Repair and Growth Factors and Cytokines

Transforming growth factors (TGFs) have a central role in regulating tissue healing by affecting cell proliferation, gene expression, and matrix protein synthesis (Roberts & Sporn, 1989). While not a direct effect, Bolander and colleagues have provided evidence that TGF-β1 and TGF-β2 can initiate both chondrogenesis and osteogenesis (Joyce et al., 1990; Izumi et al., 1992; Jingushi et al., 1992). In these studies new cartilage and bone formation appeared to be dose dependent (i.e. dependent on the local growth factor concentration). The data also suggested that TGF-β1 and TGF-β2 stimulated cell differentiation by a similar mechanism, even though they differed in terms of the ultimate amount of new cartilage and bone that was formed.

Other growth factors/hormones besides TGF and BMP may influence new bone formation following fracture. Bolander and colleagues injected recombinant acidic fibroblast growth factor into a rat fracture site (Jingushi et al., 1990). The major effect of multiple high doses (1.0 mg/50 ml) was a significant increase in cartilage tissue in the fracture gap, while lower doses had no effect. These investigators also used the reverse transcriptase-polymerase chain reaction (PCR) technique to demonstrate expression of estrogen receptor transcripts in callus tissue (Boden et al., 1989). These results suggested a role for estrogen in normal fracture repair.

Horowitz and colleagues have shown that activated osteoblasts will synthesize the cytokine, macrophage colony stimulating factor (Horowitz et al., 1989). The osteotropic agents used in this study included lipopolysaccharide, PTH1-84, PTH1-34, vitamin D and all-trans retinoic acid. This observation has led to the suggestion that osteoblast activation following fracture may lead to the production of cytokines that regulate both hematopoiesis and new bone formation. Various other proteins and polypeptides that have been found to be expressed at high levels in osteogenic cells, such as, e.g., the polypeptide designated Vgr-1 (Lyons et al. (1989) Proc. Natl. Acad. Sci. U.S.A., 86:4554-4558), also have potential for use in connection with the present invention.

5. Bone Repair and Calcium Regulating Hormones

Calcium regulating hormones such as parathyroid hormone (PTH) participate in new bone formation and bone remodeling (Raisz & Kream, 1983). PTH is an 84 amino acid calcium-regulating hormone whose principle function is to raise the $Ca^{+2}$ concentration in plasma and extracellular fluid. Studies with the native hormone and with synthetic peptides have demonstrated that the amino-terminus of the molecule (aa 1-34) contains the structural requirements for biological activity (Tregear et al., 1973; Hermann-Erlee et al., 1976; Riond, 1993). PTH functions by binding to a specific cell surface receptor that belongs to the G protein-coupled receptor superfamily (Silve et al., 1982; Rizzoli et al., 1983; Juppner et al., 1991).

Using a retroviral approach, a human full-length PTH gene construct has been introduced into cultured rat fibroblasts to create recombinant PTH-secreting cells. These cells were then transplanted into syngeneic rat recipients that were observed to develop hypercalcemia mediated by the increased serum concentrations of PTH (Wilson et al., 1992). The object of these studies was to create an animal model of primary hyperparathyroidism.

PTH has a dual effect on new bone formation, a somewhat confusing aspect of hormone function despite intensive investigation. PTH has been shown to be a potent direct inhibitor of type I collagen production by osteoblasts (Kream et al., 1993). Intact PTH was also shown to stimulate bone resorption in organ culture over 30 years ago, and the hormone is known to increase the number and activity of osteoclasts. Recent studies by Gay and colleagues have demonstrated binding of [$^{125}$I]PTH(1-84) to osteoclasts in tissue sections and that osteoclasts bind intact PTH in a manner that is both saturable and time- and temperature dependent (Agarwala & Gay, 1992). While these properties are consistent with the presence of PTH/PTHrP receptors on the osteoclast cell surface, this hypothesis is still considered controversial. A more accepted view, perhaps, is that osteoclast activation occurs via an osteoblast signaling mechanism.

On the other hand, osteosclerosis may occur in human patients with primary hyperparathyroidism (Seyle, 1932). It is well known that individuals with hyperparathyroidism do not inexorably lose bone mass, but eventually achieve a new bone remodeling steady state after an initial period of net bone loss. Chronic, low dose administration of the amino-terminal fragment of PTH (aa 1-34) also can induce new bone formation according to a time- and dose-dependent schedule (Seyle, 1932; Parsons & Reit, 1974).

Human PTH1-34 has recently been shown to: stimulate DNA synthesis in chick osteoblasts and chondrocytes in culture (van der Plas, 1985; Schluter et al., 1989; Somjen et al., 1990); increase bone cell number in vivo (Malluche et al., 1986); enhance the in vitro growth of chick embryonic cartilage and bone (Kawashima, 1980; Burch & Lebovitz, 1983; Lewinson & Silbermann, 1986; Endo et al., 1980; Klein-Nulend et al., 1990); enhance surface bone formation (both cortical and trabecular bone) in normal and osteogenic animals and in humans with osteoporosis (Reeve et al., 1976; Reeve et al., 1980; Tam et al., 1982; Hefti et al., 1982; Podbesek et al., 1983; Stevenson & Parsons, 1983; Slovik et al., 1986; Gunness-Hey & Hock, 1984; Tada et al., 1988; Spencer et al., 1989; Hock & Fonseca, 1990; Liu & Kalu, 1990; Hock & Gera, 1992; Mitlak et al., 1992; Ejersted et al., 1993); and delay and reverse the catabolic effects of estrogen deprivation on bone mass (Hock et al., 1988; Hori et al., 1988; Gunness-Hey & Hock, 1989) Liu et al., 1991). Evidence of synergistic interactions between hPTH1-34 and other anabolic molecules has been presented, including insulin-like growth factor, BMP-2, growth hormone, vitamin D, and TGF-β (Slovik et al., 1986; Spencer et al., 1989; Mitlak et al., 1992; Canalis et al., 1989; Linkhart & Mohan, 1989; Seitz et al., 1992; Vukicevic et al., 1989).

Anecdotal observation has shown that serum PTH levels may be elevated following bone fracture (Meller et al., 1984; Johnston et al., 1985; Compston et al., 1989; Hardy et al., 1993), but the significance of this observation is not understood. There are apparently no reports in the literature concerning attempts to localize either PTH or the PTH/PTHrP receptor in situ in human fracture sites or in experimental models. Furthermore, no attempt has been made to augment bone repair by the exogenous addition of PTH peptides. Although hPTH1-34 was known to function as an anabolic agent for bone, prior to the present invention, much remained to be learned about the role (if any) of PTH during bone regeneration and repair.

6. Protein Administration and Bone Repair

Several studies have been conducted in which preparations of protein growth factors, including BMPs, have been administered to animals in an effort to stimulate bone growth. The results of four such exemplary studies are described below.

Toriumi et al. studied the effect of recombinant BMP-2 on the repair of surgically created defects in the mandible of adult dogs (Toriumi et al., 1991). Twenty-six adult hounds were segregated into three groups following the creation of a 3 cm full thickness mandibular defect: 12 animals received test implants composed of inactive dog bone matrix carrier and human BMP-2, 10 animals received control implants composed of carrier without BMP-2, and BMP-4 animals received no implant. The dogs were euthanized at 2.5–6 months, and the reconstructed segments were analyzed by radiography, histology, histomorphometry, and biomechanical testing. Animals that received test implants were euthanized after 2.5 months because of the presence of well mineralized bone bridging the defect. The new bone allowed these animals to chew a solid diet, and the average bending strength of reconstructed mandibles was 27% of normal ('normal' in this case represents the unoperated, contralateral hemimandible). In contrast, the implants in the other two groups were nonfunctional even after 6 months and showed minimal bone formation.

Yasko et al. published a related study in which the effect of BMP-2 on the repair of segmental defects in the rat femur was examined (Yasko et al., 1992). The study design included a group that received a dose of 1.4 mg of BMP-2, another group that received 11.0 mg of BMP-2, and a control group that received carrier matrix alone. Endochondral bone formation was observed in both groups of animals that received BMP-2. As demonstrated by radiography, histology, and whole bone (torsion) tests of mechanical integrity, the larger dose resulted in functional repair of the 5 mm defect beginning 4.5 weeks after surgery. The lower dose resulted in radiographic and histological evidence of new bone formation, but functional union was not observed even after 9 weeks post surgery. There was also no evidence of bone formation in control animals at this time.

Chen et al. showed that a single application of 25–100 ng of recombinant TGF-β1 adjacent to cartilage induced endochondral bone formation in the rabbit ear full thickness skin wounds (Chen et al., 1991). Bone formation began 21 days following the creation of the wound and reached a peak at day 42, as demonstrated by morphological methods. Active bone remodeling was observed beyond this point.

In a related study, Beck et al. demonstrated that a single application of TGF-β1 in a 3% methylcellulose gel was able to repair surgically induced large skull defects that otherwise heal by fibrous connective tissue and never form bone (Beck et al., 1991). Bony closure was achieved within 28 days of the application of 200 mg of TGF-β1 and the rate of healing was shown to be dose dependent.

Studies such as those described above have thus established that exogenous growth factors can be used to stimulate new bone formation/repair/regeneration in vivo. Certain U.S. patents also concern methods for treating bone defects or inducing bone formation. For example, U.S. Pat. No. 4,877,864 relates to the administration of a therapeutic composition of bone inductive protein to treat cartilage and/or bone defects; U.S. Pat. No. 5,108,753 concerns the use of a device containing a pure osteogenic protein to induce endochondral bone formation and for use in periodontal, dental or craniofacial reconstructive procedures.

However, nowhere in this extensive literature does there appear to be any suggestion that osteogenic genes themselves may be applied to an animal in order to promote bone repair or regeneration. Indeed, even throughout the patent literature that concerns genes encoding various bone stimulatory factors and their in vitro expression in host cells to produce recombinant proteins, there seems to be no mention of the possibility of using nucleic acid transfer in an effort to express an osteogenic gene in bone progenitor cells in vivo or to promote new bone formation in an animal or human subject.

7. Biocompatible Matrices for use in Bone Repair

There is a considerable amount of work that has been directed to the development of biocompatible matrices for use in medical implants, including those specifically for bone implantation work. In context of the present invention, a matrix may be employed in association with the gene or DNA coding region encoding the osteotropic polypeptide in order to easily deliver the gene to the site of bone damage. The matrix is thus a "biofiller" that provides a structure for the developing bone and cartilage. Such matrices may be formed from a variety of materials presently in use for implanted medical applications.

Matrices that may be used in certain embodiments include non-biodegradable and chemically defined matrices, such as sintered hydroxyapatite, bioglass, aluminates, and other ceramics. The bioceramics may be altered in composition, such as in calcium-aluminate-phosphate; and they may be processed to modify particular physical and chemical characteristics, such as pore size, particle size, particle shape, and biodegradability. Certain polymeric matrices may also be employed if desired, these include acrylic ester polymers and lactic acid polymers, as disclosed in U.S. Pat. Nos. 4,526,909, and 4,563,489, respectively, each incorporated herein by reference. Particular examples of useful polymers are those of orthoesters, anhydrides, propylene-cofumarates, or a polymer of one or more α-hydroxy carboxylic acid monomers, (e.g. α-hydroxy acetic acid (glycolic acid) and/or α-hydroxy propionic acid (lactic acid).

Optimally, the best matrices for present purposes are those that are capable of being resorbed into the body. Potential biodegradable matrices for use in bone gene transfer include, for example, biodegradable and chemically defined calcium sulfate, tricalciumphosphate, hydroxyapatite, polylactic acid and polyanhydrides. Furthermore, biomatrices comprised of pure proteins and/or extracellular matrix components may be employed. The inventors currently prefer to use bone or dermal collagenous materials as matrices, as may be prepared from various commercially-available lyophilized collagen preparations, such as those from bovine or rat skin. Collagen matrices may also be formulated as described in U.S. Pat. No. 4,394,370, incorporated herein by reference, which concerns the use of collagenous matrices as delivery vehicles for osteogenic protein. UltraFiber™, as may be obtained from Norian Corp. (Mountain View, Calif.), is the most preferred matrix.

Further suitable matrices may also be prepared from combinations of materials, such as polylactic acid and hydroxyapatite or collagen and tricalciumphosphate. Although sufficient sequestration and subsequent delivery of an osteotropic gene is in no way a limitation of the present invention, should it be desired, a porous matrix and gene combination may also be administered to the bone tissue site in combination with an autologous blood clot. The basis for this is that blood clots have previously been employed to increase sequestration of osteogenic proteins for use in bone treatment (U.S. Pat. No. 5,171,579, incorporated herein by reference) and their use in connection with the present invention is by no means excluded (they may even attract growth factors or cytokines).

8. Nucleic Acid Delivery

The transfer of nucleic acids to mammalian cells has been proposed a method for treating certain diseases or disorders. Nucleic acid transfer or delivery is often referred to as "gene therapy". Initial efforts toward postnatal (somatic) gene therapy relied on indirect means of introducing genes into tissues, e.g., target cells were removed from the body, infected with viral vectors carrying recombinant genes, and implanted into the body. These type of techniques are generally referred to as ex vivo treatment protocols. Direct in vivo gene transfer has recently been achieved with formulations of DNA trapped in liposomes (Ledley et al., 1987); or in proteoliposomes that contain viral envelope receptor proteins (Nicolau et al., 1983); calcium phosphate-coprecipitated DNA (Benvenisty & Reshef, 1986); and DNA coupled to a polylysine-glycoprotein carrier complex (Wu & Wu, 1988). The use of recombinant replication-defective viral vectors to infect target cells in vivo has also been described (e.g., Seeger et al., 1984).

In recent years, Wolff et al. demonstrated that direct injection of purified preparations of DNA and RNA into mouse skeletal muscle resulted in significant reporter gene expression (Wolfe et al., 1990). This was an unexpected finding, and the mechanism of gene transfer could not be defined. The authors speculated that muscle cells may be particularly suited to take up and express polynucleotides in vivo or that damage associated with DNA injection may allow transfection to occur.

Wolff et al. suggested several potential applications of the direct injection method, including (a) the treatment of heritable disorders of muscle, (b) the modification of non-muscle disorders through muscle tissue expression of therapeutic transgenes, (c) vaccine development, and (d) a reversible type of gene transfer, in which DNA is administered much like a conventional pharmaceutical treatment. In an elegant study Liu and co-workers recently showed that the direct injection method can be successfully applied to the problem of influenza vaccine development (Ulmer et al., 1993).

The use of gene transfer to synoviocytes as a means of treating arthritis has also been discussed (Bandara et al., 1992; Roessler et al., 1993). The protocols considered have included both the ex vivo treatment of isolated synoviocytes and their re-introduction into the animal and also direct gene transfer in which suitable vectors are injected into the joint. The transfer of marker genes into synoviocytes has already been demonstrated using both retroviral and adenoviral technology (Bandara et al., 1992; Roessler et al., 1993).

Despite the exclusive emphasis on protein treatment by those working in this field, the present inventors saw that there was great potential for using nucleic acids themselves to promote bone regeneration/repair in vivo. In addition to the ease and cost, it was reasoned that using DNA transfer rather than peptide transfer would provide many further advantages. For example, DNA transfer allows for the expression or over-expression of integral membrane receptors on the surface of bone regeneration/repair cells, whereas this cannot be done using peptide transfer because the latter (a priori) is an extracellular manipulation. Importantly, DNA transfer also allows for the expression of polypeptides modified in a site-directed fashion with the very minimum of additional work (i.e., straightforward molecular biological manipulation without protein purification).

The inventors contemplated that both naked DNA and viral-mediated DNA could be employed in an effort to transfer genes to bone progenitor cells. In beginning to study this, the most appropriate animal model had to be employed, that is, one in which the possibilities of using nucleic acids to promote bone repair could be adequately tested in controlled studies.

9. Osteotomy Model

Prior to the present invention, three model systems were available for study in this area, including Mov13 mice, an animal model of OI. Unfortunately, each of the models suffers from significant drawbacks. With the Mov13 mice, first, these mice typically die in young adulthood because of retrovirus-induced leukemia (Schnieke et al., 1983); second, gene transfer studies in Mov13 mice conducted between postnatal weeks 8–16 (i.e. prior to the development of leukemia) may be complicated by a natural adaptation, in which a significant amount of new bone is deposited on the periosteal surface (Bonadio et al., 1993); and third, an osteotropic gene transferred into an osteotomy site may synergize with the active retrovirus and make it even more virulent.

Another system is the in vivo bone fracture model created by Einhorn and colleagues (Bonnarens & Einhorn, 1984). However, this model is a closed system that would not easily permit gene transfer in vivo. The organ culture model developed by Bolander and colleagues (Joyce et al., 1991) was also available, but again, this model is not suitable for studying gene transfer in vivo. Due to the unsuitability of the above models for studying the effects of gene transfer on bone repair and regeneration, the inventors employed a rat osteotomy system, as described below.

The important features of the rat osteotomy model are as follows: Under general anesthesia, four 1.2 mm diameter pins are screwed into the femoral diaphysis of normal adult Sprague-Dawley rats. A surgical template ensures parallel placement of the pins. An external fixator is then secured on the pins, and a 2 mm, or 5 mm, segmental defect is created in the central diaphysis with a Hall Micro 100 oscillating saw. A biodegradable implant material, soaked in a solution of plasmid DNA, other genetic construct or recombinant virus preparation, is then placed in the intramedullary canal and the defect is closed (FIG. 1).

New bone formation can be detected as early as three weeks later in the 2 mm gap, although up to 9 weeks is generally allowed for new bone formation to occur. The fixator provided the necessary stability, and there were no limitations on animal ambulation. The surgical protocol has been successfully performed on 21/21 animals to date. None of these animals have died. Assays of new bone formation are performed after sacrifice, except plain film radiography, which is performed weekly from the time of surgery to sacrifice.

Previous studies in Sprague-Dawley rats have shown that the 5 mm osteotomy gap will heal as a fibrous non-union, whereas the a gap of less than 3 mm, (such as the 2 mm gap routinely employed in the studies described herein) will heal by primary bone formation. Studies using the 5 mm gap thus allow a determination of whether transgene expression can stimulate new bone formation when fibrous tissue healing normally is expected. On the other hand, studies with the 2 mm gap allow a determination of whether transgene expression can speed up natural primary bone healing.

10. Gene Transfer Promotes Bone Repair In Vivo

The present inventors surprisingly found that gene transfer into bone progenitor cells in vivo (i.e., cells in the regenerating tissue in the osteotomy gap) could be readily achieved. Currently, the preferred methods for achieving gene transfer generally involve using a fibrous collagen implant material soaked in a solution of DNA shortly before being placed in the site in which one desires to promote bone growth. As the studies presented herein show, the implant material facilitates the uptake of exogenous plasmid constructs by cells (in the osteotomy gap) which clearly participate in bone regeneration/repair. The transgenes, following cellular uptake, direct the expression of recombinant polypeptides, as evidenced by the in vivo expression of functional marker gene products.

Further studies are presented herein demonstrating that the transfer of an osteotropic gene results in cellular expression of a recombinant osteotropic molecule, which expression is directly associated with stimulation of new bone formation. After considering a relatively large number of candidate genes, a gene transfer vector coding for a fragment of human parathyroid hormone (hPTH1-34) was chosen for the inventors' initial studies. Several factors were considered in making this choice: (a), recombinant hPTH1-34 peptides can be discriminated from any endogenous rat hormone present in osteotomy tissues; (b), hPTH1-34 peptides will stimulate new bone formation in Sprague-Dawley rats, indicating that the human peptide can efficiently bind the PTH/PTHrP receptor on the rat osteoblast cell surface; and (c), there is only one PTH/PTHrP receptor, the gene for this receptor has been cloned, and cDNA probes to the receptor are available.

Thus, in terms of understanding the mechanism of action of the transgene on new bone formation in vivo, the inventors reasoned it most straightforward to correlate the expression of recombinant hPTH1-34 peptide and its receptor with new bone formation in the rat osteotomy model. Of course, following these initial studies, it is contemplated that any one of a wide variety of genes may be employed in connection with the bone gene transfer embodiments of the present invention.

Previous studies have indicated that hPTH1-34 is a more powerful anabolic agent when given intermittently as opposed to continuously. Despite the fact that an anabolic effect would still be expected with continuous dosing, as documented by the studies of Parsons and co-workers (Tam et al., 1982) and Spencer et al. (1989), there was a concern that the PLJ-hPTH1-34 transgene may not function very effectively as transfected cells would be expected to express recombinant hPTH1-34 molecules in a constitutive manner. The finding that transfection and expression of the PLJ-hPTH1-34 transgene did effectively stimulate bone formation in the rat osteotomy model was therefore an important result.

As the osteotomy site in this model is highly vascularized, one possible complication of the studies with the PLJ-hPTH1-34 transgene is the secretion of recombinant human PTH from the osteotomy site with consequent hypercalcemia and (potentially) animal death. Weekly serum calcium levels should therefore determined when using this transgene. The fact that no evidence of disturbed serum calcium levels has been found in this work is therefore a further encouraging finding.

These studies complement others by the inventors in which direct gene transfer was employed to introduce genes into Achilles' tendon and cruciate ligament, as described in Example XI.

Various immediate applications for using nucleic acid delivery in connection with bone disorders became apparent to the inventors following these surprising findings. The direct transfer of an osteotropic gene to promote fracture repair in clinical orthopaedic practice is just one use. Other important aspects of this technology include the use of gene transfer to treat patients with "weak bones", such as in diseases like osteoporosis; to improve poor healing which may arise for unknown reasons, e.g., fibrous non-union; to promote implant integration and the function of artificial joints; to stimulate healing of other skeletal tissues such as Achilles tendon; and as an adjuvant to repair large defects. In all such embodiments, DNA is being used as a direct pharmaceutical agent.

The use of the methods and compositions of the present invention in stimulating vascular graft survival is also contemplated. The invention may thus be employed in connection with the technology described by Sandusky et al. (1992; incorporated herein by reference). In this case, the matrix part of the composition would be the biological graft, preferably made from a small intestine submucosa (SIS) graft. To practice these aspects of the invention one would simply impregnate the biological graft with the nucleic acid that one desired to transfer to the tissue surrounding the graft site.

11. Biological Functional Equivalents

As mentioned above, modification and changes may be made in the structure of an osteotropic gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | Codons | | | | |
|---|---|---|---|---|---|---|
| Alanine | Ala A | GCA | GCC | GCG | GCU | |
| Cysteine | Cys C | UGC | UGU | | | |
| Aspartic acid | Asp D | GAC | GAU | | | |
| Glutamic acid | Glu E | GAA | GAG | | | |
| Phenylalanine | Phe F | UUC | UUU | | | |
| Glycine | Gly G | GGA | GGC | GGG | GGU | |
| Histidine | His H | CAC | CAU | | | |
| Isoleucine | Ile I | AUA | AUC | AUU | | |
| Lysine | Lys K | AAA | AAG | | | |
| Leucine | Leu L | UUA | UUG | CUA | CUC | CUG | CUU |
| Methionine | Met M | AUG | | | | |
| Asparagine | Asn N | AAC | AAU | | | |
| Proline | Pro P | CCA | CCC | CCG | CCU | |
| Glutamine | Gln Q | CAA | CAG | | | |
| Arginine | Arg R | AGA | AGG | CGA | CGC | CGG | CGU |
| Serine | Ser S | AGC | AGU | UCA | UCC | UCG | UCU |
| Threonine | Thr T | ACA | ACC | ACG | ACU | |
| Valine | Val V | GUA | GUC | GUG | GUU | |
| Tryptophan | Trp W | UGG | | | | |
| Tyrosine | Tyr Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the DNA sequences of osteotropic genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

12. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes the desired osteotropic protein. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected osteotropic gene using site-directed mutagenesis is provided as a means of producing potentially useful species and is not meant to be limiting as there are other ways in which sequence variants of osteotropic genes may be obtained. For example, recombinant vectors encoding the desired osteotropic gene may be treated with mutagenic agents, such as hydroxylamine, to obtain sequence variants.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that any changes can be made in the specific embodiments which are disclosed and still obtain a like or similar result without departing from the spirit and scope of the invention.

EXAMPLE I

Animal Model for Assessing New Bone Formation

As various animal models were not suitable for studying the effects of nucleic acid transfer on bone formation, the inventors employed the following model system. The important features of the rat osteotomy model are as described in the following protocol (which is generally completed in 25–35 minutes):

The osteotomy was performed on one femur per animal. Right to left differences have not been apparent, but such differences are monitored in these studies, since the limb receiving the osteotomy is randomized.

After pre-operative preparation (i.e. shaving and betadine scrub), adult male Sprague Dawley rats (~500 gm, retired male breeders) were anesthetized using a 3% halothane 97% oxygen mixture (700 ml/min. flow rate). A lateral approach to the femur was made on one limb. Utilizing specially designed surgical guides, four 1.2 mm diameter pins were screwed into the diaphysis after pre-drilling with a high speed precision bit. A surgical template ensured precise and parallel placement of the pins. The order of pin placement was always the same: outer proximal first and then outer distal, inner proximal and inner distal (with "outer" and "inner" referring to the distance from the hip joint). Pin placement in the center of the femur was ensured by fluoroscopic imaging during pin placement. The external fixator was secured on the pins and a 5 mm or 2 mm segmental defect was created in the central diaphysis through an incision using a Hall Micro 100 Oscillating saw (#5053-60 Hall surgical blades) under constant irrigation. Other than the size of the segmental defect, there is no difference between the 5 mm and 2 mm osteotomy protocols (FIG. 1).

The contents of the osteotomy site were irrigated with sterile saline and the fibrous collagen implant material, previously soaked in a solution of plasmid DNA or other DNA construct, if appropriate, was placed in situ. The wound was then closed in layers. Since the fixator provided the necessary stability no limitations on animal ambulation existed, and other supports were not required. The surgical protocol has been successfully performed on 21/21 animals to date. None of these animals have died and no significant adverse effects have been observed, other than complications that might be associated with surgical fracture repair. Minor complications that were experienced include 1 animal that developed a post-operative osteomyelitis and 1 animal in which 2/4 pins loosened as a consequence of bone fracture.

EXAMPLE II

Implant Material for Use in Bone Gene Transfer

Various implant materials may be used for transferring genes into the site of bone repair and/or regeneration in vivo. These materials are soaked in a solution containing the DNA or gene that is to be transferred to the bone regrowth site.

One particular example of a suitable material is fibrous collagen, which may be lyophilized following extraction and partial purification from tissue and then sterilized. A particularly preferred collagen is the fibrous collagen implant material termed UltraFiber™, as may be obtained from Norian Corp., (1025 Terra Bella Ave., Mountain View, Calif., 94043). Detailed descriptions of the composition and use of UltraFiber™ are provided in Gunasekaran et al. (1993a,b; each incorporated herein by reference).

Prior to placement in osteotomy sites, implant materials are soaked in solutions of DNA (or virus) under sterile conditions. The soaking may be for any appropriate and convenient period, e.g., from 6 minutes to over-night. The DNA (e.g., plasmid) solution will be a sterile aqueous solution, such as sterile water or an acceptable buffer, with the concentration generally being about 0.5–1.0 mg/ml. Currently preferred plasmids are those such as pGL2 (Promega), pSV40β-gal, pAd.CMVlacZ, and pLJ.

EXAMPLE III

Parathyroid Hormone Gene Constructs

The active fragment of the human parathyroid hormone gene (hPTH1-34) was chosen as the first of the osteotropic genes to be incorporated into an expression vector for use in gene transfer to promote new bone formation in the rat osteotomy model.

Figure 2:
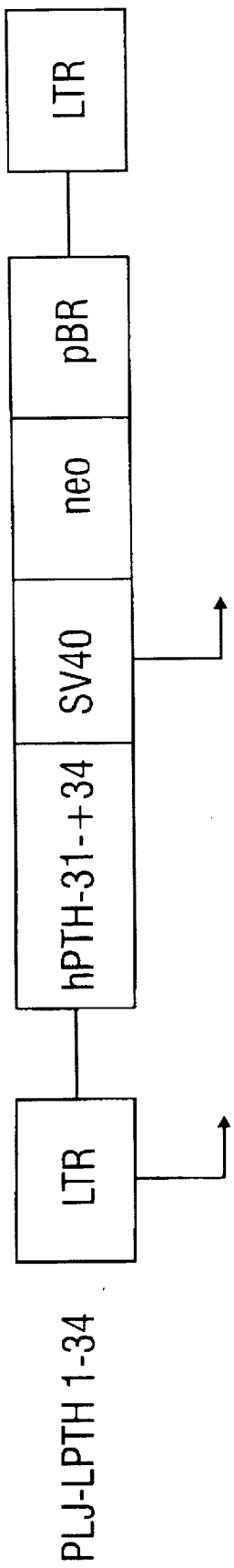
FIG. 2. PLJ-HPTH1-34 expression construct. A cDNA fragment coding for a prepro-hPTH1-34 peptide was generated by PCR (Hendy et al., 1981) and then ligated into a BamHI cloning site in the PLJ retroviral expression vector (Wilson et al., 1992). Several independent clones with the insert in the coding orientation were isolated and characterized.

The inventors chose to construct the hPTH1-34 transgene in the PLJ expression vector (FIG. 2), since this vector was appropriate for studies of transgene function both in vitro and in vivo. A schematic of the PLJ-hPTH1-34 transgene is shown in FIG. 2. The DNA and amino acid sequences of the hPTH1-34 are well known, e.g., see Hendy et al. (1981, incorporated herein by reference). To insert the transgene into the PLJ expression vector PCR of a full-length PTH recombinant clone was employed, followed by standard molecular biological manipulation.

A retroviral stock was then generated following $CaPO_4$-mediated transfection of psi crip cells with the PLJ-hPTH1-34 construct, all according to standard protocols (Sambrook et al., 1989). Independent transduced Rat-1 clones were obtained by standard infection and selection procedures (Sambrook et al., 1989).

Figure 3:
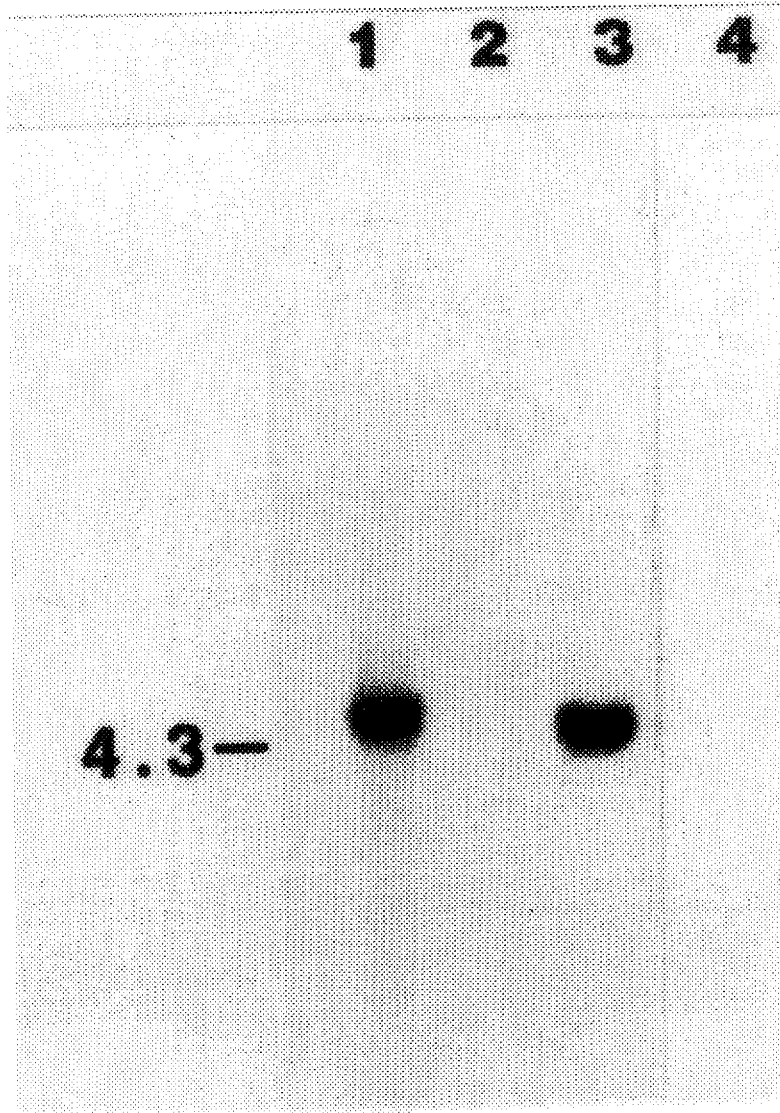
FIG. 3. Southern analysis of retroviral integration in the YZ-15 clone. 10 mg of YZ-15 genomic DNA were digested with KpnI (for which there is a unique site in the vector LTR) and analyzed by Southern blotting. A cDNA fragment that coded for prepro-hPTH1-34 was used as a probe. The positive control for the Southern hybridization conditions was a KpnI digest of genomic DNA from Rat-1 cells infected and selected with the recombinant, replication-defective retrovirus PLJ-hPTH1-84 (Wilson et al., 1992). KpnI digests of DNA were also prepared from two negative controls: native Rat-1 cells and Rat-1 cells infected and selected with BAG ("BAG cells", (Wilson et al., 1992), a replication-defective recombinant retrovirus that encodes β-galactosidase, which is an irrelevant marker gene in these studies. Lane assignments were as follows: 1, PLJ-hPTH1-84 cells; 2, BAG cells; 3, YZ-15; 4, native Rat-1 cells. DNA sizes (kb) are shown at the left of the figure. As expected, a fragment of the predicted size (e.g., 4.3 kb) is seen only in lane 1 (the positive control) and in lane 3 (YZ-15 DNA).

One clone (YZ-15) was analyzed by Southern analysis, demonstrating that the PLJ-hPTH1-34 transgene had stably integrated into the Rat-1 genome (FIG. 3). A Northern analysis was next performed to show that the YZ-15 clone expressed the PLJ-hPTH1-34 transgene, as evidenced by the presence of specific PLJ-hPTH1-34 transcripts (FIG. 4A, FIG. 4B, FIG. 4C and FIG. 4D).

EXAMPLE IV

Parathyroid Hormone Polypeptide Expression and Activity

A sensitive and specific radioimmunoassay was performed to demonstrate that the YZ-15 cells expressed and secreted a recombinant hPTH1-34 molecule (Table 2). The radioimmunoassay was performed on media from transduced Rat-1 clones. To quantify secretion of the recombinant hPTH-1-34 peptide produced by YZ-15 cells, the culture medium from one 100 mm confluent dish was collected over a 24 hour period and assayed with the NH2-terminal hPTH RIA kit (Nichols Institute Diagnostics) according to the manufacturer's protocol. PLJ-hPTH1-84 cells and BAG cells served as positive and negative controls, respectively.

Protein concentrations in Table 2 are expressed as the average of three assays plus the standard deviation (in parenthesis). The concentration of the 1-34 and full length (1-84) peptides was determined relative to a standard curve generated with commercially available reagents (Nichols Institute Diagnostics).

TABLE 2

| CELL LINES | PTH (pg/ml) |
|---|---|
| YZ-15 | 247 (±38) |
| PLJ-hPTH1-84 | 2616 (±372) |
| BAG | 12 (±3) |

As shown in Table 2, PTH expression was detected in both YZ-15 cells and PLJ-hPTH1-84 cells. BAG cells produced no detectable PTH and served as a baseline for the RIA. These results demonstrate that YZ-15 cells expressed recombinant hPTH1-34 protein.

The recombinant hPTH1-34 molecule was added to rat osteosarcoma cells and a cAMP response assay conducted in order to determine whether the secreted molecule had biological activity. Unconcentrated media was collected from YZ-15 cells, PLJ-hPTH1-84 cells, and BAG cells and was used to treat ROS17/2.8 cells for 10 minutes, as described (Majmudar et al., 1991). cAMP was then extracted from treated cells and quantified by RIA (Table 3). The amount of cAMP shown is the average of three assays. The standard deviation of the mean is shown in parenthesis.

TABLE 3

| CELL LINES | cAMP (pmol) |
|---|---|
| YZ-15 | 20.3 (±0.25) |
| PLJ-hPTH1-84 | 88.5 (±4.50) |
| BAG | 7.6 (±0.30) |

A cAMP response was induced by the recombinant PTH secreted by the YZ-15 cells and by PLJ-hPTH1-84 cells. BAG cells produced no PTH and served as the baseline for the cAMP assay. These results provide direct in vitro evidence that the PLJ-hPTH1-34 transgene directs the expression and secretion of a functional osteotropic agent.

EXAMPLE V

Bone Morphogenetic Protein (BMP) Gene Constructs

The mouse bone morphogenetic protein-4 (BMP-4) was chosen as the next of the osteotropic genes to be incorporated into an expression vector for use in promoting bone repair and regeneration.

A full length mouse BMP-4 cDNA was generated by screening a mouse 3T3 cell cDNA library (Stratagene). The human sequence for BMP-4 is well known to those of skill in the art and has been deposited in Genbank. Degenerate oligos were prepared and employed in standard PCR to obtain a murine cDNA sequence.

The ends of the cDNA clone were further modified using the polymerase chain reaction so that the full length cDNA (5'→3' direction) codes for: the natural mouse initiator Met codon, the full length mouse coding sequence, a 9 amino acid tag (known as the HA epitope), and the natural mouse stop codon. The amino acid sequence encoded by the mouse BMP-4 transgene is shown in FIG. 9; this entire sequence, including the tag, is represented by SEQ ID NO:1. As of the filing of this application, the precise nucleic acid sequence has not yet been determined, and various "wobble position" bases remain unknown.

Placement of the HA epitope at the extreme carboxy terminus should not interfere with the function of the recombinant molecule sequence in vitro or in vivo. The advantage of the epitope is for utilization in immunohistochemical methods to specifically identify the recombinant mouse BMP-4 molecule in osteotomy tissues in vivo, e.g., the epitope can be identified using a commercially available monoclonal antibody (Boehringer-Mannheim), as described herein.

Studies to demonstrate that the mouse BMP-4 transgene codes for a functional osteotropic agent include, for example, (a) transfection of COS cells and immunoprecipitation of a protein band of the correct size using a monoclonal anti-HA antibody (Boehringer-Mannheim); and (b) a quantitative in vivo bone induction bioassay (Sampath & Reddi, 1981) that involves implanting proteins from the medium of transfected COS cells beneath the skin of male rats and scoring for new bone formation in the ectopic site.

EXAMPLE VI

Detection of mRNA by Tissue in Situ Hybridization

The following technique describes the detection of mRNA in tissue obtained from the site of bone regeneration. This may be useful for detecting expression of the transgene mRNA itself, and also in detecting expression of hormone or growth factor receptors or other molecules. This method may be used in place of, or in addition to, Northern analyses, such as those described in FIG. 7.

DNA from a plasmid containing the gene for which mRNA is to be detected is linearized, extracted, and precipitated with ethanol. Sense and antisense transcripts are generated from 1 mg template with T3 and T7 polymerases, e.g., in the presence of [$^{35}$S]UTP at >6 mCi/ml (Amersham Corp., >1200 Ci/mmol) and 1.6 U/ml RNasin (Promega), with the remaining in vitro transcription reagents provided in a kit (SureSite, Novagen Inc.). After transcription at 37° C. for 1 hour, DNA templates are removed by a 15 minute digestion at 37° C. with 0.5 U/ml RNase-free DNase I, extracted, and precipitated with ethanol. Riboprobes are hydrolyzed to an average final length of 150 bp by incubating in 40 mM NaHCO$_3$, 60 mM Na$_2$CO$_3$, 80 mM DTT at 60° C., according to previously determined formula. Hydrolysis is terminated by addition of sodium acetate, pH 6.0, and glacial acetic acid to 0.09M and 0.005% (v/v), respectively, and the probes are then ethanol precipitated, dissolved in 0.1M DTT, counted, and stored at -20° C. until use.

RNase precautions are taken in all stages of slide preparation. Bouins fixed, paraffin embedded tissue sections are heated to 65° C. for 10 minutes, deparaffinized in 3 changes of xylene for 5 minutes, and rehydrated in a descending ethanol series, ending in phosphate-buffered saline (PBS). Slides will be soaked in 0.2N HCl for 5 min., rinsed in PBS, digested with 0.0002% proteinase K in PBS for 30 minutes at 37° C. and rinsed briefly with DEPC-treated water. After equilibrating for 3 minutes in 0.1M triethanolamine-HCl (TEA-HCl), pH 8.0, sections are acetylated in 0.25% (v/v) acetic anhydride in 0.1M TEA-HCl for 10 minutes at room temperature, rinsed in PBS, and dehydrated in an ascending ethanol series. Each section receives 100–200 ml prehybridization solution (0.5 mg/ml denatured RNase-free tRNA (Boehringer-Mannheim), 10 mM DTT, 5 mg/ml denatured, sulfurylated salmon sperm DNA, 50% formamide, 10% dextran sulfate, 300 mM NaCl, 1× RNase-free Denhardt's solution (made with RNase-free bovine serum albumin, Sigma), 10 mM Tris-HCl, pH 7.4, 1 mM EDTA) and then incubate on a 50° C. slide warmer in a humidified enclosure for 2 hours. The sulfurylated salmon-sperm DNA blocking reagent is used in both prehybridization and hybridization solutions to help reduce nonspecific binding to tissue by $^{35}$SH groups on the probe. It is prepared by labeling RNase-free salmon sperm DNA (Sigma) with non-radioactive α-thio-dCTP and α-thio-dATP (Amersham) in a standard random oligonucleotide-primed DNA labeling reaction. Excess prehybridization solution is removed with a brief rinse in 4× SSC before application of probe.

Riboprobes, fresh tRNA and sulfurylated salmon sperm DNA will be denatured for 10 minutes at 70° C., and chilled on ice. Hybridization solution, identical to prehybridization solution except with denatured probe added to 5×10$^6$ CPM/ml, is applied and slides incubated at 50° C. overnight in sealed humidified chambers on a slide warmer. Sense and antisense probes are applied to serial sections. Slides are rinsed 3 times in 4× SSC, washed with 2× SSC, 1 mM DTT for 30 min. at 50° C., digested with RNase A (20 mg/ml RNase A, 0.5M NaCl, 10 mM Tris, pH 8.0, 1 mM EDTA, pH 8.0) for 30 min. at 37° C., and rinsed briefly with 2× SSC, 1 mM DTT. Three additional washes are performed, each at 50° C. for 30 minutes: once in 2× SSC, 50% formamide, 1 mM DTT, and twice in 1× SSC, 0.13% (w/v) sodium pyrophosphate, 1 mM DTT.

Slides are dehydrated in an ascending ethanol series (with supplementation of the dilute ethanols (50% and 70%) with SSC and DTT to 0.1× and 1 mM, respectively). Slides are exposed to X-ray film for 20–60 hours to visualize overall hybridization patterns, dipped in autoradiographic emulsion (Kodak NTB-2, diluted to 50% with 0.3M ammonium acetate), slowly dried for 2 hours, and exposed (4° C.) for periods ranging from 8 days to 8 weeks. After developing emulsion, sections are counter stained with hematoxylin and eosin, dehydrated, and mounted with xylene-based medium. The hybridization signal is visualized under darkfield microscopy.

The above in situ hybridization protocol may be used, for example, in detecting the temporal and spatial pattern of PTH/PTHrP receptor expression. A suitable rat PTH/PTHrP receptor cDNA probe (R15B) is one that consists of a 1810 bp region encoding the full length rat bone PTH/PTHrP receptor (Abou-Samra et al., 1992). The cDNA fragment is subcloned into pcDNA 1 (Invitrogen Corp., San Diego, Calif.) and is cut out using XbaI and BamHI. This probe has provided positive signals for northern blot analysis of rat, murine, and human osteoblastic cell lines, rat primary calvarial cells, and murine bone tissue. The pcDNA I plasmid contains a T7 and SP6 promoter that facilitate the generation of cRNA probes for in situ hybridization. The full length transcript has been used to detect PTH/PTHrP receptor in sections of bone (Lee et al., 1994). The PTHrP cDNA probe (Yasuda et al., 1989) is a 400 bp subcloned fragment in pBluescript 1 KS (Stratagene). This probe has been used for in situ hybridization, generating an antisense cRNA probe using BamHI cleavage and the T3 primer and a sense cRNA probe using EcoRI cleavage and the T7 primer.

EXAMPLE VII

In Vivo Protein Detection Following Transgene Expression

1. β-galactosidase Transgene

Bacterial β-galactosidase is detected immunohistochemically and by substrate utilization assays. Osteotomy tissue specimens are fixed in Bouins fixative, demineralized, and then split in half along the longitudinal plane. One-half of each specimen is embedded in paraffin for subsequent immunohistochemical identification of the bacterial β-galactosidase protein.

For immunohistochemistry, cross-Sections (2–3 mm thick) were transferred to poly-L-Lysine coated microscope slides and fixed in acetone at 0 C. for at least 20 min. Sections were rehydrated in PBS. Endogenous peroxidase activity was quenched by immersion of tissue sections in 0.1% hydrogen peroxide (in 95% methanol) at room temperature for 10 min, and quenched sections were washed 3× in PBS. In some cases, sectioned calvariae were demineralized by immersion in 4% EDTA, 5 polyvinyl pyrrolidone, and 7% sucrose, pH 7.4, for 24 h at 4 C. Demineralized sections were washed 3× before application of antibodies. Primary antibodies were applied to sections for 30 min. Monoclonal antibodies were used without dilution in the form of hybridoma supernatant. Purified antibodies were applied to tissue sections at a concentration of 5 mg/ml.

Primary antibodies were detected with biotinylated rabbit antimouse IgG and peroxidase conjugated streptavidin (Zymed Histostain-SPkit). After peroxidase staining, sections were counterstained with hematoxylin.

Substrate utilization assays (for both β-gal and luciferase) are conducted using commercially available kits (e.g., Promega) according to the manufacturers' instructions.

2. PTH Transgenes

Recombinant PTH, such as hPTH1-34 peptide, is assayed in homogenates of osteotomy gap tissue, for example, using two commercially available radioimmunoassay kits according to the manufacturer's protocols (Nichols Institute Diagnostics, San Juan Capistrano, Calif.).

One kit is the Intact PTH-Parathyroid Hormone 100T Kit. This radioimmunoassay utilizes an antibody to the carboxy terminus of the intact hormone, and thus is used to measure endogenous levels of hormone in gap osteotomy tissue. This assay may be used to establish a baseline value PTH expression in the rat osteotomy model.

The second kit is a two-site immunoradiometric kit for the measurement of rat PTH. This kit uses affinity purified antibodies specific for the amino terminus of the intact rat hormone (PTH1-34) and thus will measure endogenous PTH production as well as the recombinant protein. Previous studies have shown that these antibodies cross-react with human PTH and thus are able to recognize recombinant molecules in vivo.

Values obtained with kit #1 (antibody to the carboxy terminus) are subtracted from values obtained with kit #2 (antibody to the amino terminus) to obtain an accurate and sensitive measurements. The level of recombinant peptide is thus correlated with the degree of new bone formation.

3. BMP Transgene

Preferably, BMP proteins, such as the mouse BMP-4 transgene peptide product, are detected immunohistochemically using a specific antibody that recognizes the HA epitope (Majmudar et al., 1991), such as the monoclonal antibody available from Boehringer-Mannheim. Antibodies to BMP proteins themselves may also be used. Such antibodies, along with various immunoassay methods, are described in U.S. Pat. No. 4,857,456, incorporated herein by reference.

Osteotomy tissue specimens are fixed in Bouins fixative, demineralized, and then split in half along the longitudinal plane. One-half of each specimen is embedded in paraffin for subsequent immunohistochemical identification of the recombinant mouse BMP-4 molecule.

EXAMPLE VIII

Direct Gene Transfer into Regenerating Bone in Vivo

To assess the feasibility of direct gene transfer into regenerating bone in vivo, marker gene transfer into cells in the rat osteotomy model was employed. These studies involved two marker genes: bacterial β-galactosidase and insect luciferase.

Aliquots of a fibrous collagen implant material were soaked in solutions of pure marker gene DNA. The implant materials were then placed in the osteotomy site, and their expression determined as described above.

Figure 5:
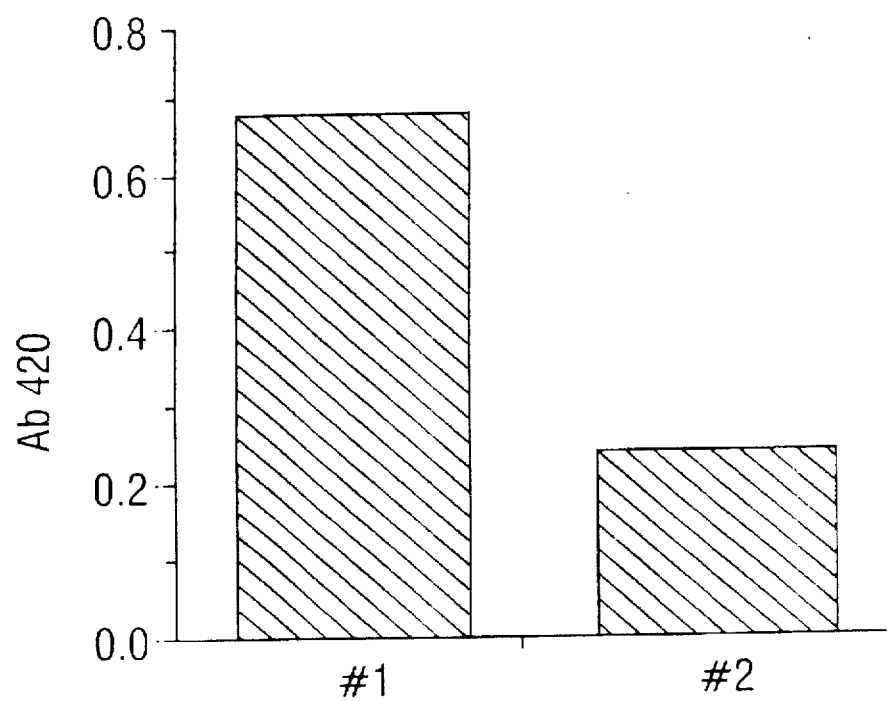
FIG. 5. Direct DNA transfer into regenerating bone: β-gal activity. The figure compares β-galactosidase activity in homogenates of osteotomy gap tissue from two Sprague-Dawley rats. In animal #1, the UltraFiber™ implant material was soaked in a solution of pSV40β-gal DNA, Promega) encoding bacterial β-galactosidase. In animal #2, the implant material was soaked in a pure solution of pGL2-Promoter Vector DNA (Promega) encoding insect luciferase. Enzyme activity was determined using substrate assay kits (β-galactosidase and Luciferase Assay Systems, Promega). Note that significant β-galactosidase activity was found only in the homogenate prepared from animal #1.
Figure 6:
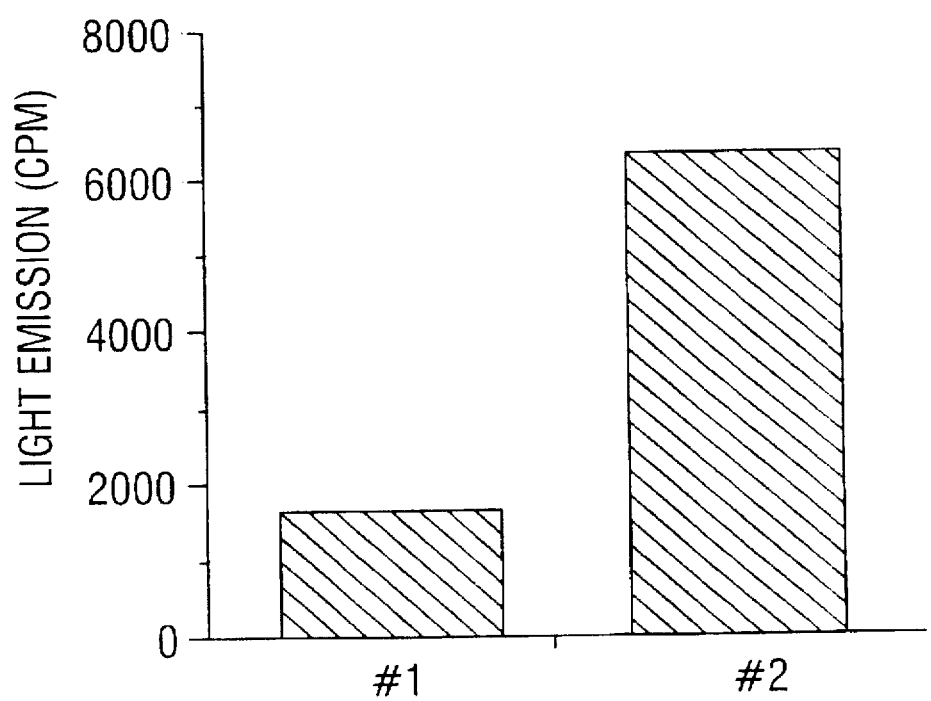
FIG. 6. Direct DNA transfer into regenerating bone: luciferase activity. The figure compares luciferase activity in aliquots of the homogenates described in FIG. 5. Luciferase activity was determined using the commercial reagents and protocols (Promega) described in FIG. 5. Note that significant luciferase activity is found only in the homogenate prepared from animal #2.

It was found that both marker genes were successfully transferred and expressed, without any failures, as demonstrated by substrate utilization assays (FIGS. 5 and 6). Since mammalian cells do not normally synthesize either marker gene product, this provides direct evidence that osteotomy repair cells were transfected in vivo and then expressed the β-galactosidase and luciferase transgenes as a functional enzymes.

EXAMPLE IX

Adenoviral Gene Transfer into Regenerating Bone in Vivo

One of the alternative methods to achieve in vivo gene transfer into regenerating bone is to utilize an adenovirus-mediated transfer event. Successful adenoviral gene transfer of a marker gene construct into bone repair cells in the rat osteotomy model has been achieved.

The inventors employed the adenoviral vector pAd.CMVlacZ, which is an example of a replication-defective adenoviral vector which can replicate in permissive cells (Stratford-Perricaudet et al., 1992). In pAd.CMVlacZ, the early enhancer/promoter of the cytomegalovirus (CMV) is used to drive transcription of lacZ with an SV40 polyadenylation sequence cloned downstream from this reporter (Davidson et al., 1993).

The vector pAd.RSV4 is also utilized by the inventors. This vector essentially has the same backbone as pAdCMVlacZ, however the CMV promoter and the single BglII cloning site have been replaced in a cassette-like fashion with BglII fragment that consists of an RSV promoter, a multiple cloning site, and a poly($A^+$) site. The greater flexibility of this vector is contemplated to be useful in subcloning osteotropic genes, such as the hPTH1-34 cDNA fragment, for use in further studies.

To generate recombinant PTH adenovirus, a 100 mm dish of 293 cells is transfected using calcium phosphate with 20 mg of a plasmid construct, e.g., the plasmid containing the hPTH1-34 insert linearized with NheI, plus 2 mg of wild type adenovirus DNA digested with XbaI and ClaI. The adenovirus DNA is derived from adenovirus type 5, which contains only a single XbaI and ClaI sites and has a partial deletion of the E3 region. Approximately 7 days post-transfection, cells and media are harvested and a lysate prepared by repeated freeze-thaw cycles. This lysate is diluted and used to infect 60 mm dishes of confluent 293 cells for 1 hour. The cells are then overlaid with 0.8% agar/1× MEM/2% calf serum/12.5 mM $MgCl_2$. Ten days post-infection, individual plaques are picked and used to infect 60 mm dishes of 293 cells to expand the amount of virus. Plaques are screened by in-situ hybridization or by PCR. Positive plaques are selected for further purification and the generation of adenoviral stocks.

To purify recombinant adenovirus, 150 mm dishes of 75–90% confluent 293 cells are infected with 2–5 PFU/cell, a titer that avoids the potential cytotoxic effects of adenovirus. Thirty hours post-infection, the cells are rinsed, removed from the dishes, pelleted, and resuspended in 10 mM Tris-HCl, pH 8.1. A viral lysate is generated by three freeze-thaw cycles, cell debris is removed by centrifugation for 10 min. at 2,000 rpm, and the adenovirus is purified by density gradient centrifugation. The adenovirus band is stored at −20° C. in sterile glycerol/BSA until needed.

Figure 10A:
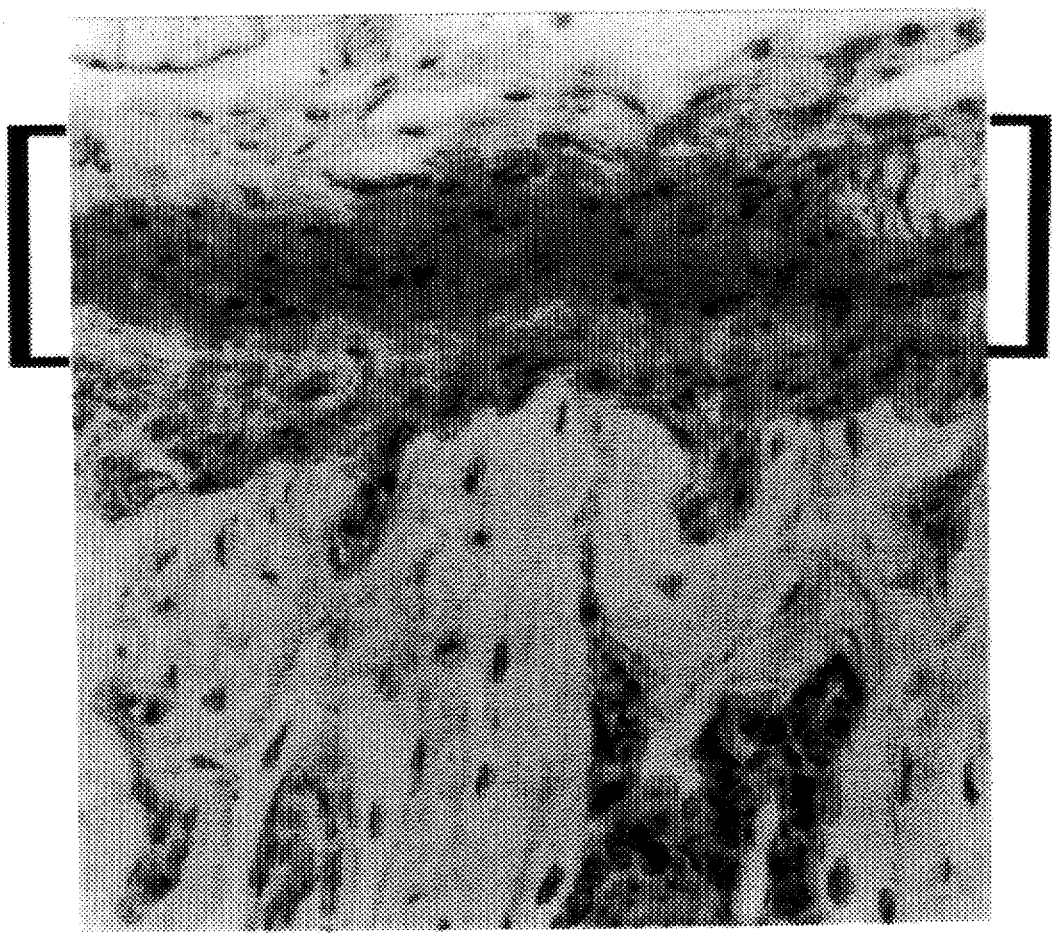
FIG. 10A, FIG. 10B and FIG. 10C. Adenovirus-mediated gene transfer into bone repair/regeneration cells in vivo. The UltraFiber™ implant was soaked for 6 min. in a solution of the AdCMVlacZ virus ($10^{10}$–$10^{11}$ plaque forming units or PFU/ml) and then implanted into the osteotomy site. The defect was allowed to heal for 3 weeks, during which time the progress of the wound healing response was monitored by weekly radiographic examination. By 3 weeks, it was estimated that 40% of the defect was filled with callus tissue. The animal was sacrificed and tissues were fixed in Bouins fixation and then demineralized for 6–8 days using standard formic acid solutions. Photomicrographs were taken from transverse sections of new bone (callus) that formed in the osteotomy site 3 weeks after surgery.
Figure 10B:
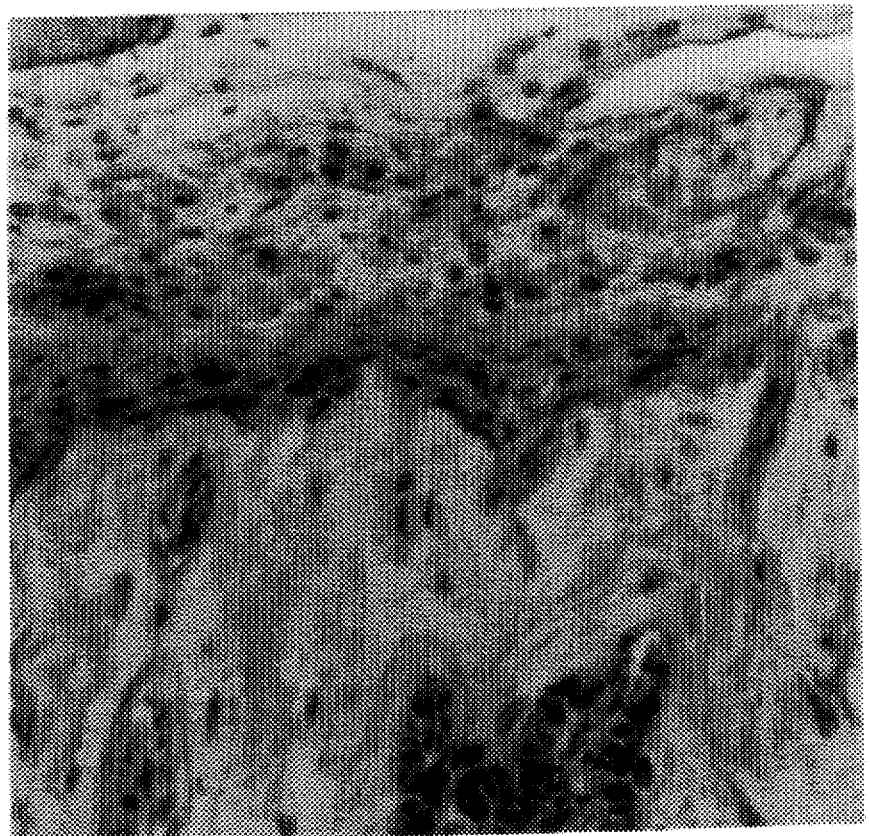
Figure 10C:
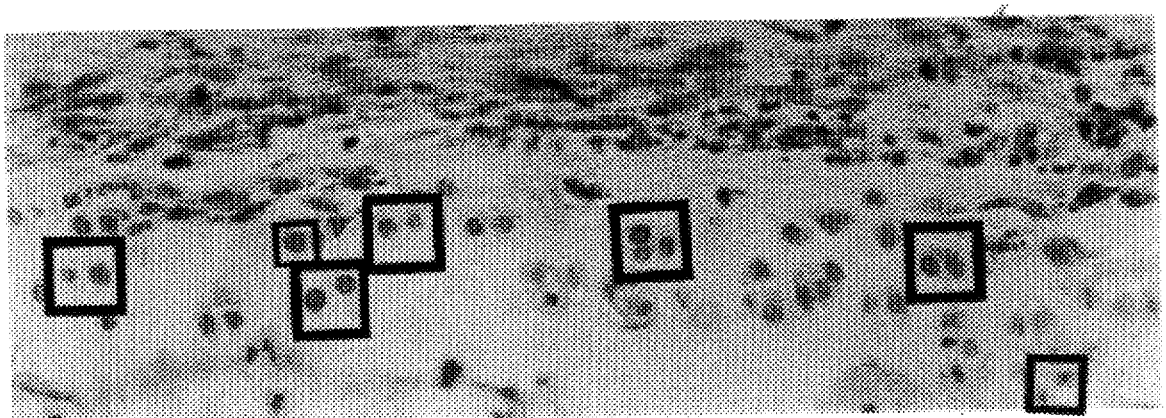

The solution of virus particles was sterilized and incubated with the implant material (from 6 mins to overnight), and the virus-impregnated material was implanted into the osteotomy gap, where viral infection of cells clearly occurred. The results obtained clearly demonstrated the exquisite specificity of the anti-β-gal antibody (Sambrook et al., 1989), and conclusively demonstrated expression of the marker gene product in chondrocyte-like cells of the osteotomy gap (FIG. 10A and FIG. 10C). The nuclear-targeted signal has also been observed in pre-osteoblasts.

EXAMPLE X

Transfer of an Osteotropic Gene Stimulated Bone Regeneration/Repair in vivo

In order for a parathyroid hormone (PTH) transgene to function as an osteotropic agent, it is likely that there is a requirement for the PTH/PTHrP receptor to be expressed in the bone repair tissue itself. Therefore, the inventors investigated PTH/PTHrP receptor expression in the rat osteotomy model.

Figure 7:
FIG. 7. Northern analysis of poly-A($^+$) RNA demonstrating expression of the PTH/PTHrP receptor in osteotomy repair tissue.

A Northern analysis of poly-$A(^+)$ RNA was conducted which demonstrated that the PTH/PTHrP receptor was expression in osteotomy repair tissue (FIG. 7).

The inventors next investigated whether gene transfer could be employed to create transfected cells that constitutively express recombinant hPTH1-34 in vivo, and whether this transgene can stimulate bone formation. The rate of new bone formation is analyzed as follows. At necropsy the osteotomy site is carefully dissected for histomorphometric analysis. The A–P and M–L dimensions of the callus tissue are measured using calipers. Specimens are then immersion fixed in Bouins fixative, washed in ethanol, and demineralized in buffered formic acid. Plastic embedding of decalcified materials is used because of the superior dimensional stability of methacrylate during sample preparation and sectioning.

Tissue blocks are dehydrated in increasing alcohol concentrations and embedded. 5 mm thick sections are cut in the coronal plane using a Reichert Polycut microtome. Sections are prepared from midway through the width of the marrow cavity to guard against a sampling bias. Sections for light microscopy are stained using a modified Goldner's trichrome stain, to differentiate bone, osteoid, cartilage, and fibrous tissue. Sections are cover-slipped using Eukitt's mounting medium (Calibrated Instruments, Ardsley, N.Y.). Histomorphometric analyses are performed under bright-field using a Nikon Optiphot Research microscope. Standard point count stereology techniques using a 10 mm×10 mm eyepiece grid reticula are used.

Total callus area is measured at 125× magnification as an index of the overall intensity of the healing reaction. Area fractions of bone, cartilage, and fibrous tissue are measured at 250× magnification to examine the relative contribution of each tissue to callus formation. Since the dimensions of the osteotomy gap reflect the baseline (time 0), a measurement of bone area at subsequent time intervals is used to indicate the rate of bone infill. Statistical significance is assessed using analysis of variance, with post-hoc comparisons between groups conducted using Tukey's studentized range t test.

Figure 8A:
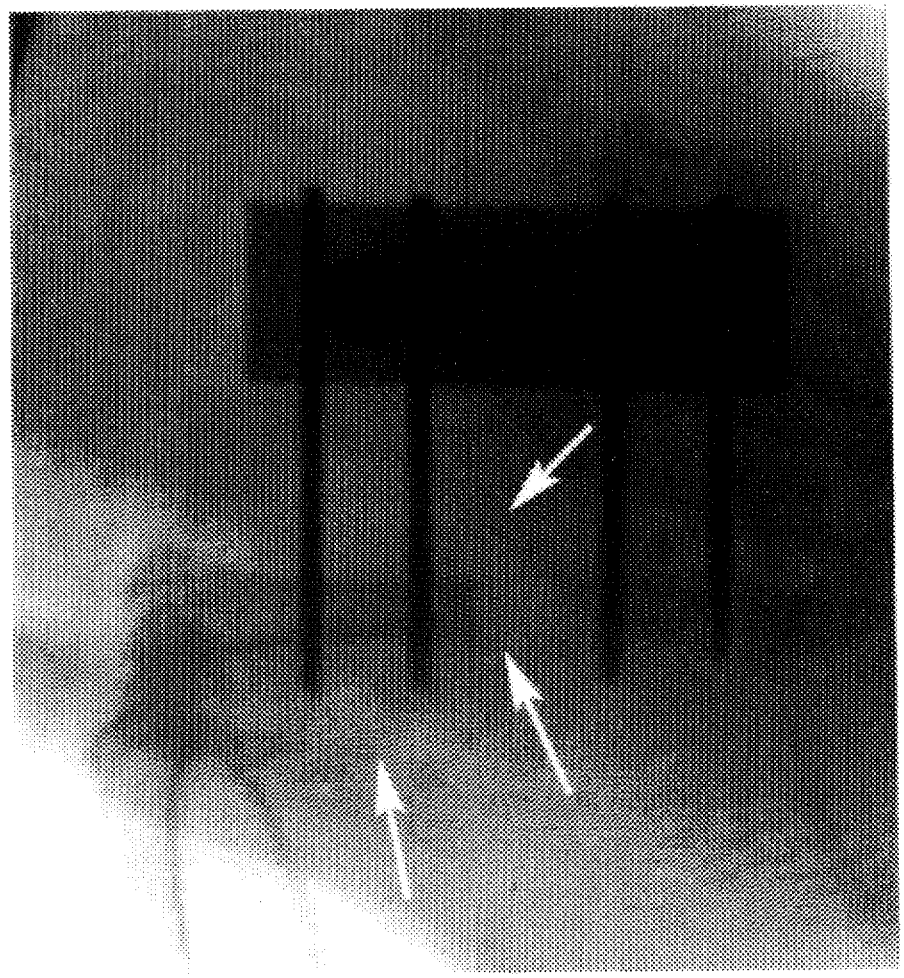
FIG. 8A. Transgene expression is capable of stimulating bone regeneration/repair in vivo.
Figure 8B:
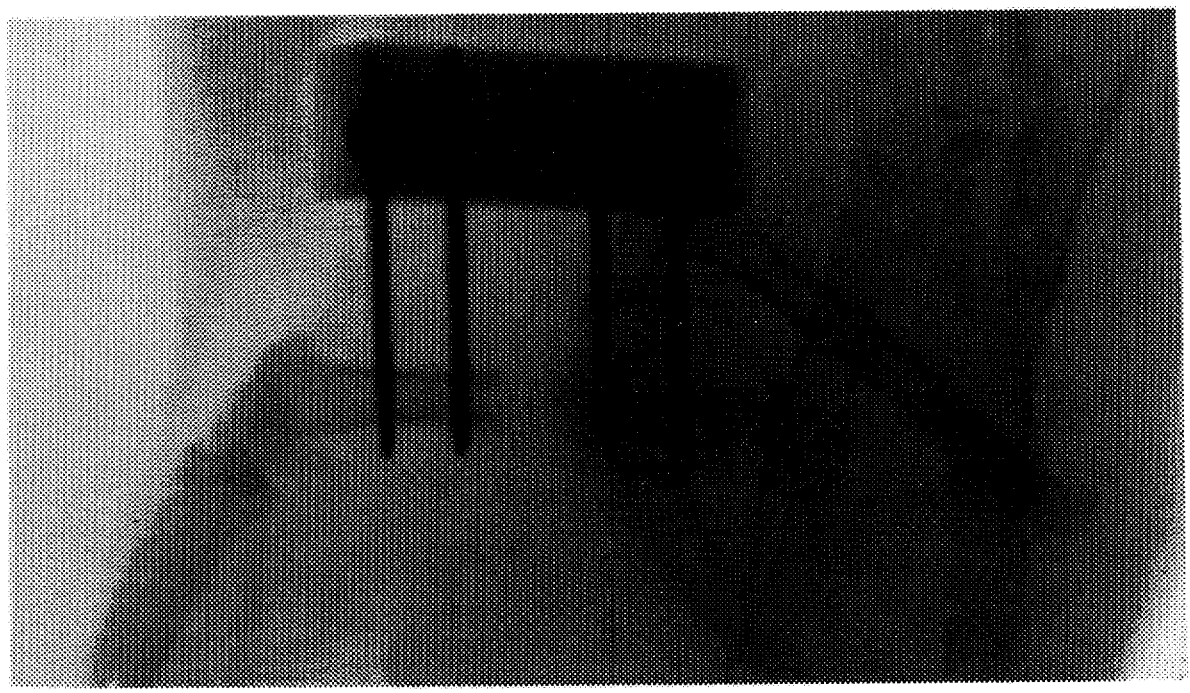
FIG. 8B. Control transgene expression is not capable of stimulating bone regeneration/repair in vivo.

In the 5 mm rat osteotomy model described above, it was found that PTH transgene expression can stimulate bone regeneration/repair in live animals (FIG. 8A and FIG. 8B). This is a particularly important finding as it is known that hPTH1-34 is a more powerful anabolic agent when given intermittently as opposed to continuously, and it is the continuous-type delivery that results from the gene transfer methods used here.

Although the present inventors have already demonstrated success of direct gene transfer into regenerating bone in vivo, the use of ex vivo treatment protocols is also contemplated. In such embodiments, bone progenitor cells would be isolated from a particular animal or human subject and maintained in an in vitro environment. Suitable areas of the body from which to obtain bone progenitor cells are areas such as the bone tissue and fluid surrounding a fracture or other skeletal defect (whether or not this is an artificially created site) and from the bone marrow. Isolated cells would then be contacted with the DNA (or recombinant viral) composition, with, or preferably without, a matrix, when the cells would take up the DNA (or be infected by the recombinant virus). The stimulated cells would then be returned to the site in the animal or patient where bone repair is to be stimulated.

EXAMPLE XI

Transfer of Genes to Achilles' Tendon and to Cruciate Ligament in vivo

The studies on regenerating bone described above complement others by the inventors in which gene transfer was successfully employed to introduce genes into Achilles' tendon and cruciate ligament.

The Achilles' tendon consists of cells and extracellular matrix organized in a characteristic tissue architecture. Tissue wounding can disrupt this architecture and stimulate a wound healing response. The wounded tendon will regenerate, as opposed to scar, if its connective tissue elements remain approximately intact. Regeneration is advantageous because scar tissue is not optimally designed to support normal mechanical function. Segmental defects in tendon due to traumatic injury may be treated with biological or synthetic implants that encourage neo-tendon formation. This strategy is limited, however, by the availability of effective (autologous) biological grafts, the long term stability and compatibility of synthetic prostheses, and the slow rate of incorporation often observed with both types of implants.

The inventors hypothesized that the effectiveness of biological grafts may be enhanced by the over-expression of molecules that regulate the tissue regeneration response. Toward this end, they developed a model system in which segmental defects in Achilles' tendon are created and a novel biomaterial, small intestinal submucosa or SIS, is used as a tendon implant/molecular delivery agent. In the present example, the ability to deliver and express marker gene constructs into regenerating tendon tissue using the SIS graft is demonstrated.

Plasmid (pSVβgal, Promega) stock solutions were prepared according to standard protocols (Sambrook et al., 1989). SIS graft material was prepared from a segment of jejunum of adult pigs (Badylak et al., 1989). At harvest, mesenteric tissues were removed, the segment was inverted, and the mucosa and superficial submucosa were removed by a mechanical abrasion technique. After returning the segment to its original orientation, the serosa and muscle layers were removed using the same abrasion technique. SIS grafts were rinsed, sterilized by treatment with dilute peracetic acid, and stored at 4° C. until use.

Mongrel dogs (all studies) were anesthetized, intubated, placed in right-lateral recumbency upon a heating pad, and maintained with inhalant anesthesia. A lateral incision from the musculotendinous junction to the plantar fascia was used to expose the Achilles' tendon. A double thickness sheet of SIS was wrapped around a central portion of the tendon, both ends were sutured, a 1.5 cm segment of the tendon was removed through a lateral opening in the graft material, and the graft and surgical site were closed. The leg was immobilized for 6 weeks and then used freely for 6 weeks. Graft tissues were harvested at time points indicated below, fixed in Bouins solution, and embedded in paraffin. Tissue sections (8 μm) were cut and used for immunohistochemistry.

In an initial study, SIS material alone (SIS-alone graft) engrafted and promoted the regeneration of Achilles' tendon following the creation of a segmental defect in mongrel dogs as long as 6 months post surgery. The remodeling process involved the rapid formation of granulation tissue and eventual degradation of the graft. Scar tissue did not form, and evidence of immune-mediated rejection was not observed.

In a second study, SIS was soaked in a plasmid DNA solution (SIS+plasmid graft) and subsequently implanted as an Achilles' tendon graft (n=2 dogs) or a cruciate ligament graft (n=2 dogs) in normal mongrel dogs. A pSVβgal plasmid that employs simian virus 40 regulatory sequences to drive β-galactosidase gene expression was used. Bacterial β-galactosidase (β-gal) activity was detectable by immunohistochemistry using a specific antibody in 4/4 animals. As a negative control, β-gal activity was not detected in the unoperated Achilles' tendon and cruciate ligament of these animals. It appeared, therefore, that SIS facilitated the uptake and subsequent expression of plasmid DNA by wound healing cells in both tendon and ligament.

Figure 11A:
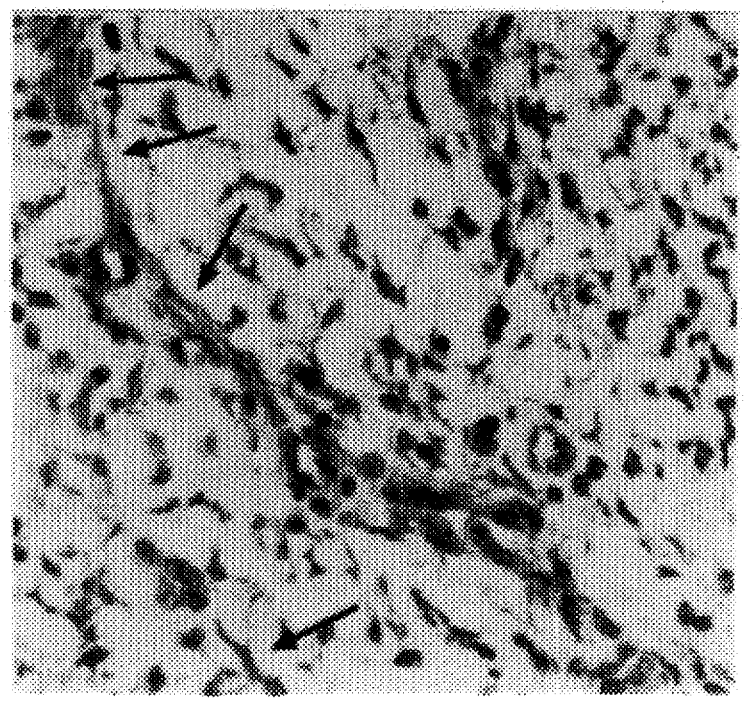
FIG. 11A and FIG. 11B. Direct transfer of bacterial β-galactosidase gene into regenerating Achilles' tendon. Cross-sections (8 µm) of Bouins fixed, paraffin embedded tissue were cut and mounted on Probeon Plus slides (Fisher). Immunohistochemistry was performed according to the protocol provided with the Histostain-SP kit (Zymed).
Figure 11B:
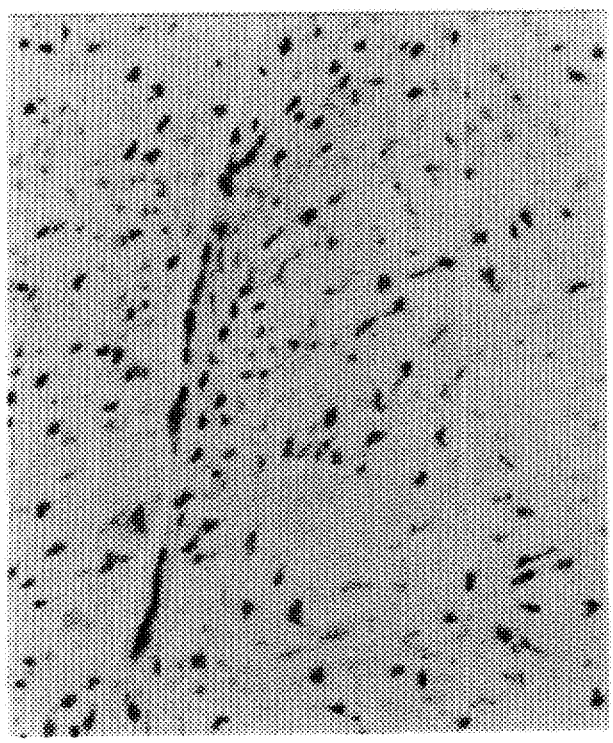

A third study was designed to evaluate the time course of β-gal transgene expression. SIS+plasmid grafts were implanted for 3, 6, 9, and 12 weeks (n=2 dogs pr time point) and transgene expression was assayed by immunohistochemistry (FIG. 11A and FIG. 11B) and by in situ hybridization. Cross-sections (8 μm) of Bouins fixed, paraffin embedded tissue were cut and mounted on ProbeOn Plus slides (Fisher). Immunohistochemistry was performed according to the protocol provided with the Histostain-SP kit (Zymed). In brief, slides were incubated with a well characterized anti-β-galactosidase antibody (1:200 dilution, 5 Prime→3 Prime), washed in PBS, incubated with a biotinylated second antibody, washed, stained with the enzyme conjugate plus a substrate-chromogen mixture, and then counterstained with hematoxylin and eosin.

Bacterial β-gal activity was detected in tendons that received the SIS+plasmid graft (8/8 animals). Although not rigorously quantitative, transgene expression appeared to peak at 9–12 weeks. Bacterial β-gal gene expression was not detected in animals that received SIS-alone grafts (N=2, 3 weeks and 12 weeks). Again, scar tissue did not form and evidence of immune-mediated rejection was not observed.

This study has demonstrated that (i) a novel biomaterial, SIS, can effectively function as a autologous graft which promotes the regeneration of tissues such as Achilles' tendon and anterior cruciate ligament, and (ii) SIS can be used to deliver a marker gene construct to regenerating tissues.

EXAMPLE XII

Mechanical Properties of New Bone Formation

The mechanical properties of new bone formed during gene transfer may be measured using, e.g., whole bone torsion tests which create a stress state in which the maximum tensile stresses will occur on planes that lie obliquely to the bone's longitudinal axis. Such tests may provide important inferences about the mechanical anisotropy of callus tissue and the degree of osseous integration of new bone tissue. These tests are particularly advantageous in the evaluation of fracture specimens, e.g., the irregular shape of callus tissue typically precludes the use of whole bone 4-point bending tests because it is impossible to reproducibly align the points from specimen to specimen.

Femurs are tested on an MTS Servohydraulic Testing Machine while moist and at room temperature. A torque sensor and rotary variable displacement transducer provides data for torque-angular displacement curves. Specially designed fixtures support each bone near the metaphyseal-diaphyseal junctions, and apply a 2-point load to the diaphysis. Tests are conducted at a constant rate of displacement equal to 20 degrees/sec. A 250 inch-ounce load cell measures the total applied force. All bones are tested while moist and at room temperature. Torque and angular displacement data are acquired using an analog-to-digital converter and a Macintosh computer and software. From this data, the following variables are calculated: a) maximum torque, b) torsional stiffness, the slope of the pre-yield portion of the curve determined from a linear regression of the data, c) energy to failure, the area under the torque-angular displacement curve to the point of failure, and d) the angular displacement ratio, the ratio of displacement at failure to displacement at yield. Statistical significance is determined using Analysis of Variance followed by multiple comparisons with appropriate corrections (e.g., Bonferroni).

This invention also provides a means of using osteotropic gene transfer in connection with reconstructive surgery and various bone remodelling procedures. The techniques described herein may thus be employed in connection with the technology described by Yasko et al., (1992), Chen et al., (1991) and Beck et al. (1991), each incorporated herein by reference.

EXAMPLE XIII

Identification and Cloning of Further Osteotropic Genes

The extracellular matrix contains a heterogeneous population of 3–20 nm filaments termed microfibrils. The inventors recently isolated and characterized the mouse and human genes for several microfibril components and characterized their expression pattern during mouse development. This example concerns the isolation and characterization of a new member of the fibrillin gene family.

Microfibrils 10 nm in diameter assist in elastic fiber assembly, serve an anchoring function in non-elastic tissues, and play a role in tissue remodeling. Consistent with a possible role in wound healing, it was found that the new fibrillin gene is expressed as alternatively spliced transcripts in fracture tissue.

The isolation and characterization of mouse cDNA clones, RT-PCR, Southern Blotting, and Northern blotting were performed using standard methods (Sambrook et al., 1989). The rat osteotomy model employed is as described hereinabove.

Figure 12:
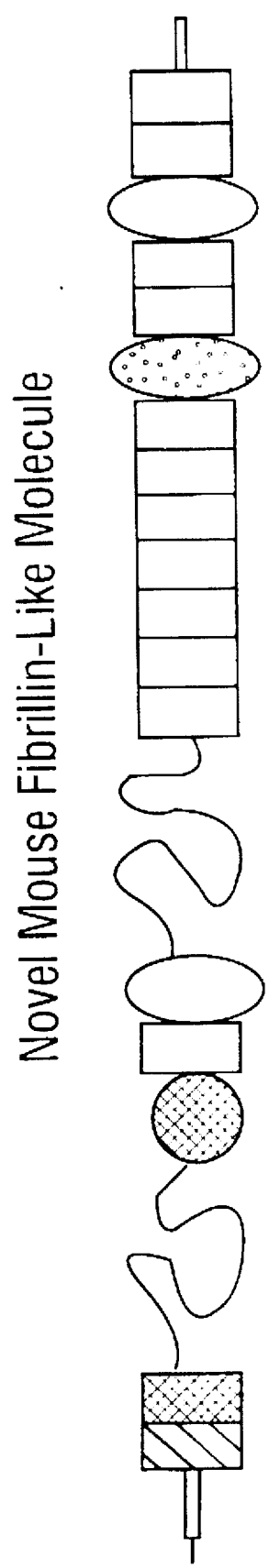
FIG. 12. Schematic diagram of the novel mouse fibrillin-like molecule. The corresponding nucleic acid and amino acid sequences are represented by SEQ ID NO:2 and SEQ ID NO:3, respectively.

In this study, the inventors isolated and characterized a novel mouse fibrillin-like cDNA. It provides a unique mRNA of 4,314 nucleotides, with an open reading frame of 3,756 nucleotides (SEQ ID NO:2). The deduced molecule is a unique polypeptide of 1,252 amino acids (SEQ ID NO:3). Excluding the signal peptide (est. 18 amino acids), the novel fibrillin-like molecule consists of five structurally distinct regions (A–E), a schematic representation of the domain structure of the new sequence is shown in FIG. 12. The largest region (region D) extends for 635 amino acids and comprises an uninterrupted series of 12 cysteine-rich repeats. Based on structural homologies, this sequence includes ten epidermal growth factor-calcium binding repeats and two transforming growth factor-β1-binding protein repeats.

A second cysteine-rich region (region B), more near the amino terminus, spans 392 amino acids. Between the two cysteine-rich regions is a 154 amino acid segment (region C) that has a high proline content (21%). The last two predicted regions of the novel fibrillin are a 22 amino acid carboxy-terminus (region E) and a 31 amino acid stretch at the amino-terminus (region A). Northern blot analysis of mouse embryo RNA agrees with the deduced size of the transcript, showing a single band of 4.55.0 kb.

The first indication of alternative splicing came from molecular cloning studies in the mouse, in which independent cDNA clones were isolated with a deletion of 51 bp from the coding sequence. PCR/Southern blot analysis provided additional evidence that the homologous 51 bp sequence was alternatively spliced in normal mouse embryo tissues.

Northern blot analysis demonstrated that the novel fibrillin gene was also expressed in rat callus three weeks after osteotomy, after mineralization has begun. Gene expression in normal adult rat bone tissue was insignificant, which suggests that microfibrils are an important part of the bone fracture healing response. The novel fibrillin-like gene was expressed in callus as a pair of alternatively spliced transcripts. This result has been independently reproduced on three occasions. Molecular cloning of the novel fibrillin gene in both mouse and rat has identified potential splice junction sites for the alternative splicing event.

This new fibrillin-like gene is present in both the mouse and rat, and is expressed in callus tissue as a pair of alternatively spliced transcripts. This is the first evidence that fibrillin-associated microfibrils are present in the extracellular matrix of callus.

This new fibrillin gene is expressed during mouse development. The transcript is widely expressed in connective tissue and mesenchyme (FIG. 13A, FIG. 13B and FIG. 13C), it is also expressed in liver, heart and CNS tissues.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abou-Samra, A. B., Juppner, H., Force, T., Freeman, M. W., Kong, X. F., Schipani, E., Urena, P., Richards, J., Bonventre, J. V., Potts, J. T., Kronenberg, H. M., Segre, G. V. (1992) Expression cloning of a common receptor for parathyroid hormone and parathyroid hormone-related peptide from rat osteoblast-like cells: a single receptor stimulates intracellular accumulation of both cAMP and inositol triphosphates and increases intracellular free Calcium. Proc. Natl. Acad. Sci. U.S.A. 89, 2732–2736.

Agarwala, N., and Gay, C. V. (1992) J. Bone Min. Res. 7, 531.

Alper, J. (1994) Boning up: newly isolated proteins heal bad breaks. Science 263, 324–325.

Bandara, G., Robbins, P. D., Georgescu, H. I., Mueller, G. M., Glorioso, J. C., and Evans, C. H., (1992) Gene Transfer to Synoviocytes: Prospects for Gene Treatment of Arthritis. DNA Cell Biol. 11:(3), 227–231.

Badylak et al., J. Surg. Res. 47, 74–80 (1989)

Beck L. S., Deguzman L., Lee W. P., Xu Y., McFatridge L. A., Gillett N. A., Amento E. P. (1991) TGF-beta 1 induces bone closure of skull defects. J. Bone Miner. Res. 11, 1257–65.

Benvenisty, N., Reshef, L (1986). *Proc. Natl. Acad. Sci. U.S.A.* 83, 9551.

Boden, S. D., Joyce, M. E., Oliver, B., and Bolander, M. E. (1989) Estrogen receptor mRNA expression in callus during fracture healing in the rat. *Calcif. Tissue Int.* 45, 34–325.

Bonadio, J. and Goldstein, S. A. (1993) Our understanding of inherited skeletal fragility and what this has taught us about bone structure and function, in *Molecular and Cellular Biology of Bone*, Noda, M., ed., Academic Press, Inc., San Diego, Calif. pp. 169–189.

Bonadio, J., Jepsen, K., Mansoura, M. K., Kuhn, J. L., Goldstein, S. A. Jaenisch, R. (1993) An adaptive response by murine skeletal tissues that significantly increases the mechanical properties of cortical bone: implications for the treatment of skeletal fragility. *J. Clin. Invest.* 92, 1697–1705.

Bonadio, J., Saunders, T. L., Tsai, E., Goldstein, S. A., Morris-Wiman, J., Brinkley, L., Dolan, D. F., Altschuler, R. A., Hawkins, J. E., Bateman, J. F., Mascara, T. and Jaenisch, R. (1990) Transgenic mouse model of the mild dominant form of osteogenesis imperfecta. *Proc. Natl. Acad. Sci. U.S.A.* 87, 7145–7149.

Bonnarens, F., and Einhorn, T. A. (1984) Production of a standard closed fracture in laboratory animal bone. *J. Orthop. Res.* 2, 97–101.

Burch, W. M., and Lebovitz, H. E. (1983) Parathyroid hormone stimulates growth of embryonic chick pelvic cartilage in vitro. *Calcif. Tissue Int.* 35, 526–532.

Byers, P. H., and Steiner, R. D. (1992) Osteogenesis imperfecta. *Annu. Rev. Med.* 43, 269–289.

Canalis, E., Centrella, M., Burch, W., et al. (1989) Insulin-like growth factor-1 mediates selective anabolic effects of parathyroid hormone in bone culture. *J. Clin. Invest.* 83, 60–65.

Carrington, J. L., Roberts, A. B., Flanders, K. C., Roche, N. S., and Reddi, A. H. (1988) Accumulation, localization, and compartmentation of transforming growth factor b during endochondral bone development. *J. Cell Biol.* 107, 1969–1975.

Centrella, M., McCarthy, T. L., and Canalis, E. (1988) Skeletal tissue and transforming growth factor-b. *FASEB J.* 22, 23066–3073.

Chen, T. L., Bates, R. L., Dudley, A., Hammonds, R. G., and Amento, E. P. (1991) Bone morphogenetic protein-2b stimulation of growth and osteogenic phenotypes in rat osteoblast-like cells: comparison with TGF-beta 1. *J. Bone Miner. Res.* 6, 1387–93.

Chen, Y., Faraco, J., Yin, W., Germiller, J., Francke, U., and Bonadio, J. (1993) Structure, chromosomal localization, and expression pattern of the murine Magp gene. *J. Biol. Chem.* 268, 27381–27389

Compston, J. E., Silver, A. C., Croucher, P. I., Brown, R. C., and Woodhead, J. S. (1989) Elevated serum intact parathyroid hormone levels in elderly patients with hip fracture. *Clin. Endo.* 31, 667–672.

Cunningham, N. S., Paralkar, V., and Reddi, A. H. (1992) Osteogenic and recombinant bone morphogenetic protein 2B are chemotactic for human monocytes and stimulate transforming growth factor b1 mRNA expression. *Proc. Natl. Acad. Sci. U.S.A.* 89, 11740–11744.

Davidson, B. L., Allen, E. D., Kozarsky, K. F., Wilson, J. M., and Roessler, B. J. (1993) A model system for in vivo gene transfer into the central nervous system using an adenoviral vector. *Nature Genetics* 3, 219–223.

Ejersted, C., Andreassen, T. T., Oxlund, H., Jorgensen, P. H., Bak, B., Haggblad, J., Torring, O., and Nilsson, M. H. L. (1993) Human parathyroid hormone (1-34) and (1-84) increase the mechanical strength and thickness of cortical bone in rats. *J. Bone Min. Res.* 8, 1097–1101.

Endo, H., Kiyoki, M., Kawashima, K., Naruchi, T., and Hashimoto, Y. (1980) Vitamin D3 metabolites and PTH synergistically stimulate bone formation of chick embryonic femur in vitro. *Nature* 286, 262–264

Gunasekaran, S., Bathhurst, I. C., Constantz, B. R., Quiaoit, J., Bar, P. J., Gospodarowicz, D. (1993). Mineralized Collagen As A Substitute for Autograft Bone That Can Deliver Bone Morphogenic Protein. The 19th Annual Meeting of the SOCIETY FOR BIOMATERIALS, April 28, p. 253

Gunasekaran, S., Quiaoit, J., Constantz, B. R. (1993). Role of Mineralized Collagen As An Osteoconductive Biomaterial. The 19th Annual Meeting of the SOCIETY FOR BIOMATERIALS, April 28, p. 161.

Gunasekaran, Subramanian, Ph.D., Constantz, Brent R., Ph.D., Quiaoit, James. Norian Corporation. Mountain View, Calif.; and Ross, John, Ph.D., Department of Chemistry, Stanford University, Stanford, Calif., Abstract V7.5, p. 426.

Gunness-Hey, M., and Hock, J. M. (1989) Loss of the anabolic effect of parathyroid hormone on bone after discontinuation of hormone in rats. *Bone* 10, 447–452.

Gunness-Hey, M., and Hock, J. M. (1984) Increased trabecular bone mass in rats treated with human synthetic parathyroid hormone. *Metab. Bone Dis.* 5, 177–180.

Hardy, J. R. W., Conlan, D., Hay, S., and Gregg, P. J. (1993) Serum ionized calcium and its relationship to parathyroid hormone after tibial fracture. *J. Bone Jt. Surg.* 75, 645–649.

Hefti, E., Trechsel, U., Bonjor, J-P., Fleisch, H., and Schenk, R. (1982) *Clin. Sci.* 62, 389–396

Hendy, G. H., Kronenberg, H. M., Potts, J. T., and Rich, A. (1981) Nucleotide sequence of cloned cDNAs encoding human preproparathyroid hormone. *Proc. Natl. Acad. Sci. U.S.A.* 78, 7365–7369.

Herrmann-Erlee, M. P. M., Heersche, J. N. M., Hekkelman, J. W., Gaillard, P. J., Tregear, G. W., Parsons, J. A., and Potts, J. T. (1976) Effects on bone in vitro of bovine parathyroid hormone and synthetic fragments representing residues 1-34, 2-34 and 3-34. *Endocrine Research Communications* 3, 21–35.

Hock, J. M., and Gera, I. (1992) Effects of continuous and intermittent administration and inhibition of resorption on the anabolic response of bone to parathyroid hormone. *J. Bone and Min. Res.* 7, 65–72.

Hock, J. M., and Fonseca, J. (1990) Anabolic effect of human synthetic parathyroid hormone (1-34) depends on growth hormone. Endocrinology 127, 1804.

Hock, J. M., Gera, I., Fonseca, J., and Raisz, L. J. (1988) Human parathyroid hormone-(1-34) increases bone mass in ovariectomized and orchidectomized rats. *Endocrinology* 122, 2899–2904.

Hori, M., Uzawa, T., Morita, K., Noda, T., Takahashi, H., and Inoue, J. (1988) Effect of human parathyroid hormone [PTH (1-34)] on experimental osteopenia of rats induced by ovariectomy. *J. Bone Min. Res.* 3, 193–199.

Horowitz, M. C., Einhorn, T. A., Philbrick, W., et al. (1989) Functional and molecular changes in colony stimulating factor secretion by osteoblasts. *Connective Tissue Res.* 20, 159–168.

Huggins, C. B., McCarroll, H. R., and Blocksom, B. H. (1936) Experiments on the theory of osteogenesis. The influence of local calcium deposits on ossification; the osteogenic stimulus of epithelium. *Arch. Surg.* 32, 915.

Izumi, T., Scully, S. P., Heydemann, A., and Bolander, M. E. (1992) Transforming growth factor b1 stimulates type II collagen expression in cultured periosteal-derived cells. *J. Bone Min. Res.* 7, 115–11.

Jepsen, K. J. (1994) Characterization of the hierarchical composite properties of cortical bone: a transgenic approach. Ph.D. Thesis (Bioengineering), University of Michigan.

Jepsen, K. J., Kuhn, J. L., Mansoura, M. K., Goldstein, S. A., Wu, H., Jaenisch, R., and Bonadio, J. Expression of a single functioning COL1A1 transgene rescues the skeletal phenotype of Mov13 transgenic mice. Submitted for publication.

Jingushi, S., Joyce, M. E., and Bolander, M. E. (1992) Genetic expression of extracellular matrix proteins correlates with histologic changes during fracture repair. *J. Bone Min. Res.* 7, 1045–1055.

Jingushi, S., Heydemann, A., Kana, S. K., Macey, L. R. and Bolander, M. E. Acidic fibroblast growth factor injection stimulates cartilage enlargement and inhibits cartilage gene expression in rat fracture healing. (1990) *J. Orthop. Res.* 8, 364–371.

Johnston, C. C., Norton, J., Khairi, M. R. A., Kernek, C., Edouard, C., Arlot, M., and Meunier, P. J. (1985) Heterogeneity of fracture syndromes in postmenopausal women. *J. Clin. Endo. Metab.* 61, 551–556.

Joyce, M. E., Jingushi, S., and Bolander, M. E. (1991) Role of growth factors in fracture healing. in Clinical and Experimental Approaches to Dermal and Epidermal Repair: Normal and Chronic Wounds. ed., Wiley-Liss, Inc. pp. 391–416.

Joyce, M. E., Roberts, A. B., Sporn, M. B., and Bolander, M. E. (1990) Transforming growth factor-b and the initiation of chondrogenesis and osteogenesis in the rat femur. *J. Cell Biol.* 110, 195–2207.

Juppner, H., Abou-Samra, A. B., Freeman, M., Kong, X. F., Schipani, E., Richards, J., Kolakowski, L. F., Hock, J., Potts, J. T., Kronenberg, H. M., Segre, G. V. (1991) A G-protein-linked receptor for parathyroid hormone and parathyroid hormone-related peptide. *Science* 254, 1024–1026.

Kawashima, K. (1980) Growth stimulative effect of parathyroid hormone, calcitonin and $N^6,O2'$-dibutyryl adenosine 3',5'-cyclic monophosphoric acid on chick embryonic cartilage cultivated in a chemically defined medium. Endocrinol. Jpn. 27, 349–356.

Klein-Nulend, J., Fall, P. M., and Raisz, L. G. (1990) Comparison of the effects of synthetic human parathyroid hormone-related peptide of malignancy and bovine PTH-(1-34) on bone formation and resorption in organ culture. *Endocrinology* 126, 223–227.

Kream, B. E., LaFrancis, D., Petersen, D. N., Woody, C., Clark, S., Rowe, D. W., and Lichtler, A. Parathyroid hormone represses al(I) collagen promoter activity in cultured calvariae from neonatal transgenic mice. (1993) *Mol. Endocrinology* 7, 399–408.

Kyte & Doolittle (1982) *J. Mol. Biol.* 157:105–132

Lee K., Deeds, J. D., Chiba, S., Un-no, M., Bond, A. T., and Segre, G. V. Parathyroid hormone induces sequential c-fos expression in bone cells in vivo: in situ localization of its receptor and c-fos mRNAs. *Endocrinology*.

Lewinson, D., and Silbermann, M. (1986) Parathyroid hormone stimulates proliferation of chondroprogenitor cells in vitro. *Calcif. Tissue Int.* 38, 155–162.

Ledley, J. (1987). *J. Pediatrics* 110, 1.

Linkhart, T. A., and Mohan, S. (1989) Parathyroid hormone stimulates release of insulin-like growth factor-1 (IGF-1) and IGF-II from neonatal mouse calvaria in organ culture. *Endocrinology* 125, 1484–1491.

Liu, C. C., Kalu, D. N., Salerno, E., Echon, R., Hollis, B. W., and Ray, M. (1991) Preexisting bone loss associated with ovariectomy in rats is reversed by parathyroid hormone. *J. Bone and Min. Res.* 6, 1071–1080.

Liu, C. C., and Kalu, D. N. (1990) Human parathyroid hormone (1-34) prevents bone loss and augments bone formation in sexually mature ovariectomized rats. *J. Bone Min. Res.* 5, 973–982.

Luyten, F. P., Cunningham, N. S., Ma, S., Muthukumaran, N., Hammonds, R. G., Nevins, W. B., Wood, W. I., and Reddi, A. H. (1989) Purification and partial amino acid sequence of osteogenic, a protein initiating bone differentiation. *J. Biol. Chem.* 264, 13377–13380.

Majmudar, G., Bole, D., Goldstein, S. A., Bonadio, J. (1991) Bone cell culture in a three-dimensional polymer bead stabilizes the differentiated phenotype and provides evidence that osteoblastic cells synthesize type III collagen and fibronectin. *J. Bone and Min. Res.* 6, 869–881.

Malluche, H. H., Matthews, C., Faugere, M-C., Fanti, P., Endres, D. B., and Friedler, R. M. (1986) 1,25-dihydroxyvitamin D maintains bone cell activity, and parathyroid hormone modulates bone cell number in dogs. *Endocrinology* 119, 1298–1304.

Meller, Y., Kestenbaum, R. S., Mozes, M., Mozes, G., Yagil, R., and Shany, S. (1984) Mineral and endocrine metabolism during fracture healing in dogs. *Clin. Orthop. Rel. Res.* 187, 289–295.

Mitlak, B. H., Williams, D. C., Bryant, H. U., Paul, D. C., and Neer, R. M. (1992) Intermittent administration of bovine PTH-(1-34) increases serum 1,25-dihydroxyvitamin D concentrations and spinal bone density in senile (23 month) rats. *J. Bone Min. Res.* 7, 479–484.

Nicolau, C., et al. (1983). *Proc. Natl. Acad. Sci. U.S.A.* 80, 1068.

O'Malley Jr., B. W. and Ledley, F. D., (1993) Somatic Gene Therapy in otolaryngology-Head and Neck Surgery. *Arch Otolaryngol Head Neck Surg.* 119, 1191–1197.

Ozkaynak, E., Rueger, D. C., Drier, E. A., Corbett, C., Ridge, R. J., Sampath, T. K., and Oppermann, H. (1990) OP-1 cDNA encodes an osteogenic protein in the TGF-b family. *EMBO J.* 9, 2085–2093.

Paralkar, V. M., Hammonds, R. G., and Reddi, A. H. Identification and characterization of cellular binding proteins (receptors) for recombinant human bone morphogenetic protein 2B, an initiator of bone differentiation cascade. (1991) *Proc. Natl. Acad. Sci. U.S.A.* 88, 3397–3401.

Parsons, J. A. and Reit, B. (1974) Chronic response of dogs to parathyroid hormone infusion. *Nature* 250, 254–257.

Podbesek, R., Edouard, C., Meunier, P. J., Parsons, J. A., Reeve, J., Stevenson, R. W., and Zanelli, J. M. (1983) Effects of two treatment regimes with synthetic human parathyroid hormone fragment on bone formation and the tissue balance of trabecular bone in greyhounds. *Endocrinology* 112, 1000–1006.

Prockop, D. J. (1990) Mutations that alter the primary structure of type I collagen. The perils of a system for generating large structures by the principle of nucleated growth. *J. Biol. Chem.* 265, 15349–15352.

Raisz, L. G., and Kream, B. E. (1983) Regulation of bone formation. *N. Engl. J. Med.* 309, 29–35.

Reeve, J., Meunier, P. J., Parsons, J. A., Bernat, M., Bijvoet, O. L., Courpron, P., Edouard, C., Klenerman, L., Neer, R. M., Renier, J. C., Slovik, D., Vismans, F. J. F. E., and Potts, J. T. (Jun. 7, 1980) Anabolic effect of human parathyroid hormone fragment on trabecular bone in involutional osteoporosis: a multicentre trial. *Br. Med. J.* 1340–1344.

Reeve, J., Hesp, R., Williams, et al. (May 15, 1976) Anabolic effect of low doses of a fragment of human parathyroid hormone on the skeleton in postmenopausal osteoporosis. *Lancet* 1035–1038.

Riond, J-L. (1993) Modulation of the anabolic effect of synthetic human parathyroid hormone fragment (1–34) in the bone of growing rats by variations in dosage regimen. *Clin. Sci.* 85, 223–228.

Rizzoli, R. E., Somerman, M., Murray, T. M., and Aurbach, G. D. (1983) Binding of radioiodinated parathyroid hormone to cloned bone cells. *Endocrinology* 113, 1832.

Roberts, A. B. and Sporn, M. B. The transforming growth factor-betas. in Handbook of Experimental Pharmacology: Peptide Growth Factors and Their Receptors. Vol. 95, M. B. Sporn and A. B. Roberts, eds., Springer-Verlag, Heidelberg, 1989.

Rosen, V., Wozney, J. M., Wang, E. A., Cordes, P., Celeste, A., McQuaid, D., and Kurtzberg, L. Purification and molecular cloning of a novel group of BMPs and localization of BMP mRNA in developing bone. (1989) *Connect. Tissue Res.* 20, 313–319.

Roessler, B. J., Allen, E. D., Wilson, J. M., Hartman, J. W., and Davidson, B. L., Adenoviral-mediated Gene Transfer to Rabbit Synovium In Vivo. (1993) *J. Clin. Invest.* 92, 1085–1092.

Sambrook, J., Fritsch, E. F., and Maniatis, T. *Molecular Cloning, A Laboratory Manual.* Cold Spring Harbor Laboratory Press, 1989, pp. 18.60.

Sampath, T. K., Nathanson, M. A., and Reddi, A. H. (1984) In vitro transformation of mesenchymal cells derived from embryonic muscle into cartilage in response to extracellular matrix components of bone. *Proc. Natl. Acad. Sci. U.S.A.* 81, 3419–3423.

Sampath, T. K. and Reddi, A. H. (1981). Dissociative extraction and reconstitution of extracellular matrix components involved in local bone differentiation. *Proc. Natl. Acad. Sci. U.S.A.* 78, 7599–7603.

Sandusky, G. E., Jr., Badylak, S. F., Morff, R. J., Johnson, W. D., Lantz, G. (1992) *Am. J. Path.,* 140, No. 2, 317.

Schluter, K-D., Hellstern, H., Wingender, E., and Mayer, H. (1989) The central part of parathyroid hormone stimulates thymidine incorporation of chondrocytes. *J. Biol. Chem.* 264, 11087–11092.

Schnieke, A., Harbers, K., and Jaenisch, R. (1983) Embryonic lethal mutation in mice induced by retrovirus insertion into the α1(I) collagen gene. *Nature* 304, 315–320.

Seeger, C., Ganem, D., Varmus, H. E. (1984). *Proc. Natl. Acad. Sci. U.S.A.* 81, 5849.

Seitz, P. A., Zhu, B-T., and Cooper, C. W. (1992) Effect of transforming growth factor b on parathyroid hormone receptor binding and cAMP formation in rat osteosarcoma cells. *J. Bone Min. Res.* 7, 541–546.

Selye, H. (1932) *Endocrinology* 16, 547

Shimahama, S., Rosenberg, M. A., Fagan, A. M., Wolff, J. A., Short, M. P., Breakefield, X. O., Friedmann, T., and Gage, F. H. (1989) Grafting genetically modified cells into the rat brain: characteristics of *E. coli* b-galactosidase as a reporter gene. *Molecular Brain Research* 5, 271–278.

Shimell, M. J., Ferguson, E. L., Childs, S. R., and O'Connor, M. B. (1991). The Drosophila dorsal-ventral patterning gene tolloid is related to human bone morphogenetic protein 1. *Cell* 67, 469–481.

Silve, C. M., Hradek, G. T., and Arnaud, C. D. (1982) Parathyroid hormone receptor in intact embryonic chicken bone: characterization and cellular localization. *J. Cell. Biol.* 94, 379.

Slovik, D. M., Rosenthal, D. I., Doppelt, S. H., Potts, J. T., Daly, M. A., Campbell, J. A., Neer, R. M. (1986) Restoration of spinal bone in osteoporotic men by treatment with human parathyroid hormone (1–34) and 1,25-dihydroxyvitamin D. *J. Bone Min. Res.* 1, 377–381.

Somjen, D., Schluuter, K-D., Wingener, E., Mayer, H., and Kaye, A. M. (1990) Stimulation of cell proliferation in skeletal tissues of the rat by defined parathyroid hormone fragments. *Biochem J.* 272, 781–785.

Spencer, E. M., Si, E. C. C., Liu, C. C., and Howard, G. A. (1989) Parathyroid hormone potentiates the effect of insulin-like growth factor-I on bone formation. *Acta Endocrinological (Copenh)* 121, 435–442.

Stevenson, R. W., and Parsons, J. A. (1983) Effects of parathyroid hormone and the synthetic 1-34 amino-terminal fragment in rats and dogs. *J. Endocr.* 97, 21–30.

Stratford-Perricaudet, L. D., Makeh, I., Perricaudet, M., and Briand, P. (1992) Widespread long-term gene transfer to mouse skeletal muscles and heart. *J. Clin. Invest.* 90, 626–630.

Tada, K., Yamamuro, T., Okumura, H., Kasai, R., and Takahashi, H. (1988) *Bone* 11, 163–169.

Tam, C. S., Heersche, J. N. M., Murray, T. M., and Parsons, J. A. (1982) Parathyroid hormone stimulates the bone apposition rate independently of its resorptive action: differential effects of intermittent and continuous administration. *Endocrinology* 110, 506–512.

Toriumi, D. M., Kotler, H. S., Luxenberg, D. P., Holtrop, M. E., and Wang, E. A. Mandibular reconstruction with a recombinant bone-inducing factor. (1991) *Arch. Otolaryngol. Head Neck Surg.* 117, 1101–1112.

Tregear, G. W., Van Rietschoten, J., Greene, E., Ketmann, H. T., Niall, H. D., Reit, B., Parsons, J. A., and Potts, J. T. (1973) Bovine parathyroid hormone: minimum chain length of synthetic peptide required for biologic activity. *Endocrinology* 93, 1349–1353.

Ulmer, J. B., Donnelly, J. J., Parker, S. E., et al. (1993) Heterologous protection against influenza by injection of DNA encoding a viral protein. *Science* 259, 1745–1749.

Urist, M. R., DeLange, R. J., and Finerman, G. A. M. Bone cell differentiation and growth factors. *Science* 220, 680–686 (1983).

Urist, M. R. Bone formation by autoinduction. *Science* 150, 893–899 (1965).

van der Plas, A. (1985) Direct effect of parathyroid hormone on the proliferation of osteoblast-like cells; a possible involvement of cyclic AMP. *Biochem. Biophys. Res. Comm.* 129, 918–925.

Vukicevic, S., Luyten, F. P., and Reddi, A. H. (1989) Stimulation of the expression of osteogenic and chondrogenic phenotypes in vitro by osteogenic. *Proc. Natl. Acad. Sci. U.S.A.* 86, 8793–8797.

Wang, E. A., Rosen, V., D'Alessandro, J. S., Bauduy, M., Cordes, P., Harada, T., Israel, D., Hewick, R. M., Kerns, K. M., LaPan, P., Luxenberg, D. P., McQuaid, D., Moutsatsos, I. K., Nove, J., and Wozney, J. M. (1990) Recombinant human bone morphogenetic protein induces bone formation. *Proc. Natl. Acad. Sci. U.S.A.* 87, 2220–2224.

Wilson, J. M., Grossman, M., Thompson, A. R. et al. (1992) Somatic gene transfer in the development of an animal model for primary hyperparathyroidism. *Endocrinology* 130, 2947–2954.

Wolff, J. A., Malone, R. W., Williams, P., Chong, W., Acsadi, G., Jani, A., and Felgner, P. L. (1990) Direct gene transfer into mouse muscle in vivo. *Science* 247, 1465–1468.

Wozney, J. M., Rosen, V., Celeste, A. J., Mitsock, L. M., Whitters, M. J., Kriz, R. W., Hewick, R. M., and Wang, E. A. (1988) Novel regulators of bone formation: molecular clones and activities. *Science* 242, 1528–1534.

Yasko, A. W., Lane, J. M., Fellinger, E. J., Rosen, V., Wozney, J. M., and Wang, E. A. (1992) The healing of segmental bone defects, induced by recombinant human bone morphogenetic protein (rhBMP-2). A radiographic, histological, and biomechanical study in rats. *J. Bone Joint Surg.* 5, 659–70.

Yasuda T, Banville Rabbani S A, Hendy G N, Goltzman. (1989) Rat parathyroid hormonelike peptide: Comparison with the human homologue and expression in malignant and normal tissue. *Mol. Endocrinol.* 3, 518–525.

What is claimed is:

1. A method for transferring a nucleic acid segment into bone progenitor cells located within a bone progenitor tissue site of an animal, comprising contacting said tissue site with a composition comprising a nucleic acid segment and a structural bone-compatible matrix so as to transfer said nucleic acid segment into said cells, wherein said nucleic acid segment expresses a transcriptional or translational product in said cells.

2. The method of claim 1, wherein the contacting process comprises bringing said nucleic acid segment into contact with said structural bone-compatible matrix to form a matrix-nucleic acid segment composition and bringing said matrix-nucleic acid segment composition into contact with said tissue site.

3. The method of claim 1, wherein said nucleic acid segment is a DNA molecule.

4. The method of claim 1, wherein said nucleic acid segment is an RNA molecule.

5. The method of claim 1, wherein said nucleic acid segment is an antisense nucleic acid molecule.

6. The method of claim 1, wherein said nucleic acid segment is a linear nucleic acid molecule, a plasmid or a recombinant insert within the genome of a recombinant virus.

7. The method of claim 1, wherein said nucleic acid segment encodes a polypeptide or protein that stimulates bone progenitor cells when expressed in said cells.

8. The method of claim 1, wherein said structural bone-compatible matrix is a collagenous, metal, hydroxyapatite, bioglass, aluminate, bioceramic, acrylic ester polymer, lactic acid polymer, glycolic acid polymer or lactic acid/glycolic acid polymer matrix.

9. The method of claim 8, wherein said structural bone-compatible matrix is a titanium matrix.

10. The method of claim 9, wherein said structural bone-compatible matrix is a titanium matrix coated with hydroxylapatite.

11. The method of claim 8, wherein said structural bone-compatible matrix is a collagen preparation.

12. A method of stimulating bone progenitor cells located within a bone progentor tissue site of an animal, comprising contacting said tissue site with a composition comprising an osteotropic gene and a structural bone-compatible matrix so as to promote expression of said gene in said cells.

13. The method of claim 12, wherein expression of said gene in said cells stimulates said cells to promote bone tissue growth.

14. The method of claim 12, wherein the contacting process comprises bringing said osteotropic gene into contact with said structural bone-compatible matrix to form a matrix-gene composition and bringing said matrix-gene composition into contact with said tissue site.

15. The method of claim 12, wherein said osteotropic gene is in the form of plasmid DNA, a DNA insert within the genome of a recombinant adenovirus, a DNA insert within the genome of a recombinant adeno-associated virus (AAV) or a DNA insert within the genome of a recombinant retrovirus.

16. The method of claim 12, wherein said osteotropic gene is a parathyroid hormone (PTH) gene, a bone morphogenetic protein (BMP) gene, a growth factor gene, a growth factor receptor gene, a cytokine gene or a chemotactic factor gene.

17. The method of claim 16, wherein said osteotropic gene is a transforming growth factor (TGF) gene, a fibroblast growth factor (FGF) gene, a granulocyte/macrophage colony stimulating factor (GMCSF) gene, an epidermal growth factor (EGF) gene, a platelet derived growth factor (PDGF) gene, an insulin-like growth factor (IGF) gene, or a leukemia inhibitory factor (LIF) gene.

18. The method of claim 15, wherein said osteotropic gene is a TGF-$\alpha$, TGF-$\beta$1 or TGF-$\beta$2 gene.

19. The method of claim 16, wherein said osteotropic gene is a PTH gene.

20. The method of claim 16, wherein said osteotropic gene is a BMP-2A, BMP-2B, BMP-3, BMP-4, BMP-5, BMP-6, BMP-7 or BMP-8 gene.

21. The method of claim 20, wherein said osteotropic gene is a BMP-2 or BMP-4 gene.

22. The method of claim 12, wherein said structural bone-compatible matrix is a collagenous, metal, hydroxylapatite, bioglass, aluminate, bioceramic, acrylic ester polymer, lactic acid polymer, glycolic acid polymer or lactic acid/glycolic acid polymer matrix.

23. The method of claim 22, wherein said structural bone-compatible matrix is a titanium matrix.

24. The method of claim 23, wherein said structural bone-compatible matrix is a titanium matrix coated with hydroxylapatite.

25. The method of claim 22, wherein said structural bone-compatible matrix is a collagen preparation.

26. The method of claim 13, wherein said matrix-gene composition is applied to a bone fracture site in said animal.

27. The method of claim 13, wherein said matrix-gene composition is implanted within a bone cavity site in said animal.

28. The method of claim 27, wherein said bone cavity site is the result of dental or periodontal surgery or the removal of an osteosarcoma.

29. A composition comprising a nucleic acid segment in association with a structural bone-compatible matrix.

30. The composition of claim 29, wherein said nucleic acid segment is a DNA molecule.

31. The composition of claim 29, wherein said nucleic acid segment is an RNA molecule.

32. The composition of claim 29, wherein said nucleic acid segment is an antisense nucleic acid molecule.

33. The composition of claim 29, wherein said nucleic acid segment is a linear nucleic acid molecule, a plasmid or a recombinant insert within the genome of a recombinant virus.

34. The composition of claim 29, wherein said nucleic acid segment encodes a polypeptide or protein that stimulates bone progenitor cells when expressed in said cells.

35. The composition of claim 29, wherein said structural bone-compatible matrix is a collagenous, titanium, hydroxylapatite, hydroxylapatite-coated titanium, bioglass, aluminate, bioceramic, acrylic ester polymer lactic acid polymer, glycolic acid polymer or lactic acid/glycolic acid polymer matrix.

36. The composition of claim 35, wherein said structural bone-compatible matrix is a collagen preparation.

37. A composition comprising an osteotropic gene in association with a structural bone-compatible matrix, said composition being capable of stimulating bone growth when administered to a bone progenitor tissue site of an animal.

38. The composition of claim 37, wherein said osteotropic gene is in the form of plasmid DNA, a DNA insert within the genome of a recombinant adenovirus, a DNA insert within the genome of a recombinant adeno-associated virus (AAV) or a DNA insert within the genome of a recombinant retrovirus.

39. The composition of claim 37, wherein said osteotropic gene is a PTH, BMP-2A, BMP-2B, BMP-3, BMP-4, BMP-5, BMP-6, BMP-7, BMP-8, TGF-$\alpha$, TGF-$\beta$1, TGF-$\beta$2, FGF, GMCSF, EGF, PDGF, IGF or a LIF gene.

40. The composition claim 39, wherein said osteotropic gene is a TGF-$\alpha$, TGF-$\beta$1, TGF-$\beta$2, PTH, BMP-2 or BMP-4 gene.

41. The composition of claim 37, wherein said structural bone-compatible matrix is a collagenous, metal, hydroxyapatite, bioglass, aluminate, bioceramic, acrylic ester polymer, lactic acid polymer, glycolic acid polymer or lactic acid/glycolic acid polymer matrix.

42. The composition of claim 41, wherein said structural bone-compatible matrix is a titanium matrix.

43. The composition of claim 42, wherein said structural bone-compatible matrix is a titanium matrix coated with hydroxylapatite.

44. The composition of claim 41, wherein said structural bone-compatible matrix is a collagen preparation.

45. An osteotropic device, comprising an osteotropic gene capable of expression in bone progenitor cells, the gene associated with an amount of a structural bone-compatible matrix effective to absorb said gene, wherein said device is capable of stimulating bone formation when implanted within a bone progenitor tissue site of an animal.

46. The device of claim 45, wherein said device is a titanium or a hydroxylapatite-coated titanium device.

47. The device of claim 45, wherein said device is shaped to join a bone fracture site in said animal.

48. The device of claim 45, wherein said device is shaped to fill a bone cavity site in said animal.

49. The device of claim 45, wherein said device is an artifical joint.

50. The method of claim 1, wherein said bone progenitor cells are stem cells, macrophages, fibroblasts, vascular cells, osteoblasts, chondroblasts or osteoclasts.

51. The method of claim 50, wherein said bone progenitor cells are fibroblasts.

52. The method of claim 2, wherein said nucleic acid segment is absorbed in said structural bone-compatible matrix.

53. The method of claim 2, wherein said nucleic acid segment is adsorbed to said structural bone-compatible matrix.

54. The method of claim 2, wherein said nucleic acid segment is impregnated within said structural bone-compatible matrix.

55. The method of claim 8, wherein said structural bone-compatible matrix is a lactic acid polymer, glycolic acid polymer or lactic acid/glycolic acid polymer matrix.

56. The method of claim 12, wherein said bone progenitor cells are stem cells, macrophages, fibroblasts, vascular cells, osteoblasts, chondroblasts or osteoclasts.

57. The method of claim 56, wherein said bone progenitor cells are fibroblasts.

58. The method of claim 14, wherein said nucleic acid segment is absorbed in said structural bone-compatible matrix.

59. The method of claim 14, wherein said nucleic acid segment is adsorbed to said structural bone-compatible matrix.

60. The method of claim 14, wherein said nucleic acid segment is impregnated within said structural bone-compatible matrix.

61. The method of claim 22, wherein said structural bone-compatible matrix is a lactic acid polymer, glycolic acid polymer or lactic acid/glycolic acid polymer matrix.

62. A method of delivering a nucleic acid segment to a fibroblast cell located within a repair tissue site of an animal, comprising contacting said tissue site with a composition comprising a nucleic acid segment and a structural bone-compatible matrix to effect uptake of the nucleic acid segment into the fibroblast cell and to promote expression of a transcriptional or translational product in said cell.

63. A method of delivering at least one selected nucleic acid segment to a fibroblast cell located within a repair tissue site of an animal, comprising the steps of:
 (a) preparing a matrix-nucleic acid composition comprising at least one nucleic acid segment and a structural bone-compatible matrix; and
 (b) contacting said repair tissue site with the matrix-nucleic acid composition to effect uptake of the nucleic acid segment by the fibroblast cell wherein said nucleic acid segment expresses a transcriptional or translational product in said cell.

64. The method of claim 63, wherein said nucleic acid segment is a linear nucleic acid molecule, a plasmid or a recombinant insert within the genome of a recombinant virus.

65. The method of claim 63, wherein said structural bone-compatible matrix is a collagenous, metal, hydroxylapatite, hydroxylapatite-coated metal, bioglass, aluminate, bioceramic, acrylic ester polymer, lactic acid polymer, glycolic acid polymer or lactic acid/glycolic acid polymer matrix.

66. The method of claim 65, wherein said structural bone-compatible matrix is a collagenous matrix.

67. The method of claim 65, wherein said structural bone-compatible matrix is a lactic acid polymer, glycolic acid polymer or lactic acid/glycolic acid polymer matrix.

68. The composition of claim 29, wherein said nucleic acid segment is absorbed in said structural bone-compatible matrix.

69. The composition of claim 29, wherein said nucleic acid segment is adsorbed to said structural bone-compatible matrix.

70. The composition of claim 29, wherein said nucleic acid segment is impregnated within said structural bone-compatible matrix.

71. The composition of claim 35, wherein said structural bone-compatible matrix is a lactic acid polymer, glycolic acid polymer or lactic acid/glycolic acid polymer matrix.

72. The composition of claim 37, wherein said osteotropic gene is absorbed in said structural bone-compatible matrix.

73. The composition of claim 37, wherein said osteotropic gene is adsorbed to said structural bone-compatible matrix.

74. The composition of claim 37, wherein said osteotropic gene is impregnated within said structural bone-compatible matrix.

75. The composition of claim 41, wherein said structural bone-compatible matrix is a lactic acid polymer, glycolic acid polymer or lactic acid/glycolic acid polymer matrix.

76. The method of claim 19, wherein said osteotropic gene is a PTH1-34 gene.

77. The composition of claim 40, wherein said osteotropic gene is a PTH1-34 gene.

\* \* \* \* \*

UNITED STATES PATENT AND TRADEMARK OFFICE
CERTIFICATE OF CORRECTION

PATENT NO. : 5,763,416
DATED : June 9, 1998
INVENTOR(S) : Bonadio et al.

It is certified that error appears in the above-identified patent and that said Letters Patent is hereby corrected as shown below:

column 1, line 5, before '1. Field of the Invention', insert the following -- This invention was made, in part, with Government support under Grant Number AR40679, awarded by the National Institute of Health. The U.S. Government has certain rights in this invention. --.

Signed and Sealed this

Tenth Day of August, 1999

*Attest:*

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,763,416

DATED : June 9, 1998

INVENTOR(S) : Bonadio et al.

It is certified that error appears in the above-identified patent and that said Letters Patent is hereby corrected as shown below:

In claim 8, column 65, line 15, delete "hydroxyapatite" and insert -- hydroxylapatite -- therefor.

In claim 37, column 66, line 41, delete "structural".

In claim 41, column 66, line 60, delete "hydroxyapatite" and insert -- hydroxylapatite -- therefor.

In claim 49, column 67, line 16, delete "artifical" and insert -- artificial -- therefor.

In claim 58, column 67, line 39, delete "nucleic acid segment" and insert -- osteotropic gene -- therefor.

In claim 59, column 67, line 42, delete "nucleic acid segment" and insert -- osteotropic gene -- therefor.

In claim 60, column 67, line 45, delete "nucleic acid segment" and insert -- osteotropic gene -- therefor.